(12) United States Patent
Rau et al.

(10) Patent No.: US 9,062,094 B2
(45) Date of Patent: Jun. 23, 2015

(54) DIPEPTIDE-BASED PRODRUG LINKERS FOR ALIPHATIC AMINE-CONTAINING DRUGS

(75) Inventors: Harald Rau, Dossenheim (DE); Torben Lessmann, Neustadt an der Weinstrasse (DE)

(73) Assignee: Ascendis Pharma AS, Hellerup (DK)

( * ) Notice: Subject to any disclaimer, the term of this patent is extended or adjusted under 35 U.S.C. 154(b) by 0 days.

(21) Appl. No.: 13/574,092

(22) PCT Filed: Jan. 21, 2011

(86) PCT No.: PCT/EP2011/050821
§ 371 (c)(1),
(2), (4) Date: Oct. 15, 2012

(87) PCT Pub. No.: WO2011/089216
PCT Pub. Date: Jul. 28, 2011

(65) Prior Publication Data
US 2013/0053301 A1 Feb. 28, 2013

(30) Foreign Application Priority Data
Jan. 22, 2010 (EP) .................................. 10151465

(51) Int. Cl.
| A61K 38/00 | (2006.01) |
| A61K 47/00 | (2006.01) |
| C07K 1/13 | (2006.01) |
| A61K 47/48 | (2006.01) |
| C07K 1/107 | (2006.01) |

(52) U.S. Cl.
CPC ............. *C07K 1/13* (2013.01); *A61K 47/48215* (2013.01); *A61K 47/48338* (2013.01); *C07K 1/1077* (2013.01)

(58) Field of Classification Search
CPC .................. A61K 39/39558; A61K 47/48384; A61K 38/00
See application file for complete search history.

(56) References Cited

U.S. PATENT DOCUMENTS

| 5,952,294 | A | 9/1999 | Lazo et al. |
| 6,613,879 | B1 | 9/2003 | Firestone et al. |
| 7,163,923 | B2 | 1/2007 | Sergeeva et al. |
| 7,879,588 | B2 | 2/2011 | Vetter et al. |
| 7,968,085 | B2 | 6/2011 | Hersel et al. |
| 2008/0241102 | A1 | 10/2008 | Hersel et al. |
| 2010/0291021 | A1 | 11/2010 | Vetter et al. |
| 2011/0009315 | A1 | 1/2011 | Hersel et al. |
| 2011/0053848 | A1 | 3/2011 | Cleemann et al. |
| 2011/0112021 | A1 | 5/2011 | Rau et al. |
| 2011/0172390 | A1 | 7/2011 | Vetter et al. |
| 2011/0223230 | A1 | 9/2011 | Hersel et al. |
| 2012/0058084 | A1 | 3/2012 | Rau et al. |
| 2012/0156259 | A1 | 6/2012 | Rau et al. |
| 2012/0156260 | A1 | 6/2012 | Rau et al. |
| 2012/0191039 | A1 | 7/2012 | Rau et al. |

FOREIGN PATENT DOCUMENTS

| WO | WO 99/30727 | 6/1999 |
| WO | WO 02/38590 | 5/2002 |
| WO | WO 02/083180 | 10/2002 |
| WO | WO 02/089789 | 11/2002 |
| WO | WO 2004/019993 | 3/2004 |
| WO | WO 2004/043493 | 5/2004 |
| WO | WO 2004/108070 | 12/2004 |
| WO | WO 2009/095479 | 8/2009 |
| WO | WO 2009/099763 | 8/2009 |
| WO | WO 2009123768 A2 * | 10/2009 |

OTHER PUBLICATIONS

Uehara et al., peptides, 1993, vol. 14, 175-178.*
Roberts et al., Advanced Drug Delivery Reviews, 2002, 54, 459-476.*
Santos et al., "Cyclization-activated prodrugs. Synthesis, reactivity and toxicity of dipeptide esters of paracetamol", Bioorganic & Medicinal Chemistry Letters, 2005, 1595-1598, 15, Elsevier.
Product list of JenKem Technology, USA (accessed and downloaded from www.jenkemusa.com on Jul. 28, 2009).
Suaifan et al., "Effects of steric bulk and stereochemistry on the rates of diketopiperazine formation from *N*- aminoacyl-2,2-dimethylthiazolidine-4-carboxamides (Dmt dipeptide amides)-a model for a new prodrug inker system", Tetrahedron, Nov. 27, 2006, 11245-11266, 62, 48, Elsevier, Amsterdam NL.
Brady et al., "Design and Synthesis of a Pro-Drug of Vinblastine Targeted at Treatment of Prostate Cancer with Enhanced Efficacy and Reduced Systemic Toxicity", J. Med. Chem., 2002, 4706-4715, 45, American Chemical Society.
Wipf et al., "Synthesis of Chemoreversible Prodrugs of *ara*-C with Variable Time-Release Profiles. Biological Evaluation of Their Apoptotic Activity", Bioorganic & Medicinal Chemistry, 1996, 1585-1596, 4, 10, Pergamon.
Gomes et al., "Cyclization-activated Prodrugs", Molecules, 2007, 2484-2506, 12, MDPI.
Hamel et al., "Cyclosporin A prodrugs: design, synthesis and biophysical properties", J. Pept. Res., 2004, 147-154, 63, Blackwell Munksgaard.
Greenwald et al., "A New Aliphatic Amino Prodrug System for the Delivery of Small Molecules and Proteins Utilizing Novel PEG Derivatives", J. Med. Chem., 2004, 726-734, 47, American Chemical Society.
Garman et al., "The preparation and properties of novel reversible polymer-protein conjugates", FEBS Letters, Nov. 1987, 361-365, 223, 2, Elsevier Science Publishers BV.

(Continued)

*Primary Examiner* — Marcela M Cordero Garcia
*Assistant Examiner* — Kaipeen Yang
(74) *Attorney, Agent, or Firm* — Frommer Lawrence & Haug LLP

(57) ABSTRACT

The present invention relates to a prodrug or a pharmaceutically acceptable salt thereof, comprising a drug linker conjugate D-L, wherein D being a biologically active moiety containing an aliphatic amine group is conjugated to one or more polymeric carriers via dipeptide-containing linkers L. Such carrier-linked prodrugs achieve drug releases with therapeutically useful half-lives. The invention also relates to pharmaceutical compositions comprising said prodrugs and their use as medicaments.

15 Claims, No Drawings

(56) References Cited

OTHER PUBLICATIONS

Lee et al., "Targeted Enzyme-Responsive Drug Carriers: Studies on the Delivery of a Combination of Drugs", Angew. Chem., 2004, 1707-1710, 16, Wiley-VCH Verlag GmbH & Co. KGaA, Weinheim.

Shabat et al., "Chemical Adaptor Systems", Chem. Eur. J., 2004, 2626-2634, 10, Wiley-VCH Verlag GmbH & Co. KGaA, Weinheim.

Antczak et al., "A New Acivicin Prodrug Designed for Tumor-Targeted Delivery", Bioorganic & Medicinal Chemistry, 2001, 2843-2848, 9, Elsevier Science Ltd.

Greenwald et al., "Drug Delivery Systems Based on Trimethyl Lock Lactonization: Poly(ethylene glycol) Prodrugs of Amino-Containing Compounds", J. Med. Chem., 2000, 475-487, 43, American Chemical Society.

Testa et al., Metabolic Hydrolysis and Prodrug Design, 2003, p. 4, Wiley VCH.

Cavallaro et al., "Polymeric Prodrug for Release of an Antitumoral Agent by Specific Enzymes", Bioconjugate Chem., 2001, 143-151, 12, American Chemical Society.

Testa et al., Metabolic Hydrolysis and Prodrug Design (Chapter 8: "The Hydrolysis of Carboxylic Acid Ester Prodrugs"), 419-534, Wiley-VCH, 2006.

Bhatt et al., "Synthesis and in Vivo Antitumor Activity of Poly(L-glutamic acid) Conjugates of 20 (S)-Camptothecin", J. Med. Chem., 2003, 190-193, 46, American Chemical Society.

Cheng et al., "Sythesis of Linear, β-Cyclodextrin-Based Polymers and Their Camptothecin Conjugates", Bioconjugate Chem, 2003, 1007-1017, 14, American Chemical Society.

Luo et al., "A Hyaluronic Acid-Taxol Antitumor Bioconjugate Targeted to Cancer Cells", Biomacromolecules, 208-218, 1, American Chemical Society, 2000.

Greenwald et al., "Drug Delivery Systems Employing 1,4- or 1,6-Elimination: Poly(ethylene glycol) Prodrugs of Amine-Containing Compounds", J. Med. Chem., 1999, 3657-3667, 42, American Chemical Society.

Testa et al., Metabolic Hydrolysis and Prodrug Design, 2003, p. 4, Wiley-VCH.

Peleg-Shulman et al., "Reversible PEGylation: A Novel Technology to Release Native Interferon α2 over a Prolonged Time Period", J. Med. Chem., 2004, 4897-4904, 47, American Chemical Society.

Caliceti et al., "Pharmacokinetic and biodistribution properties of poly(ethylene glycol)-protein conjugates", Advanced Drug Delivery Reviews, 2003, 1261-1277, 55, Elsevier B.V.

Duncan et al., "The Drawing Era of Polymer Therapeutics", Nature Reviews Drug Discovery, 2003, 347-360, 2, Nature Publishing Group.

Na et al., "Monitoring of peptide acylation inside degrading PLGA microspheres by capillary electrophoresis and MALD1-TOF mass spectrometry", Journal of Controlled Release, 2003, 291-299, 92, Elsevier B.V.

* cited by examiner

US 9,062,094 B2

DIPEPTIDE-BASED PRODRUG LINKERS FOR ALIPHATIC AMINE-CONTAINING DRUGS

The present application claims priority from PCT Patent Application No. PCT/EP2011/050821 filed on Jan. 21, 2011, which claims priority from European Patent Application No. EP 10 151 564.1 filed on Jan. 22, 2010, the disclosures of which are incorporated herein by reference in their entirety.

BACKGROUND OF THE INVENTION

1. Field of the Invention

The present invention is directed to carrier-linked prodrugs having temporary amide linkages between substituted dipeptide moieties and aliphatic amine groups of biologically active entities such as peptides, proteins, natural products or synthetic chemical compounds. Such carrier-linked prodrugs are characterized by slow release of unmodified biologically active entity.

It is noted that citation or identification of any document in this application is not an admission that such document is available as prior art to the present invention.

Typically, carriers employed for extended time-action engineering in drug delivery are either used in a non-covalent fashion, with the drug physicochemically formulated into a solvent-carrier mixture, or by permanent covalent attachment of a carrier reagent to one of the drug's functional groups.

Non-covalent drug encapsulation into polymeric carriers has been applied to depot formulations for long-acting release profiles. Typically, the drug is mixed with carrier material and processed in such fashion, that the drug becomes distributed inside the bulk carrier. For instance polymer-drug aggregates may be shaped as microparticles which are administered as an injectable suspension or the polymer-drug aggregates are formulated as gels which are administered in a single bolus injection. Known in the art are also liposomal formulations, where the carrier may be a polymeric or non-polymeric entity capable of solubilizing the drug. Drug release occurs when the carrier swells or physically deteriorates or chemical degradation allows diffusion of the drug to the exterior and subsequently into the biological environment. Such chemical degradation processes may be autohydrolytic or enzyme-catalyzed. An example for a marketed drug based on bolus administration of a drug-polymer gel is Lupron Depot. An example for a marketed drug based on suspended microparticles is Nutropin Depot. An example for a marketed drug based on a liposomal formulation is Doxil.

A disadvantage of the non-covalent approach is that in order to prevent uncontrolled, burst-type release of the drug, encapsulation of the drug has to be highly efficient by creating a sterically highly crowded environment. Restraining the diffusion of an unbound, water soluble drug molecule requires strong van der Waals contacts, frequently mediated through hydrophobic moieties. Many conformationally sensitive drugs, such as proteins or peptides, are rendered dysfunctional during the encapsulation process and/or during subsequent storage of the encapsulated drug. In addition, such amino-containing drugs readily undergo side reactions with carrier degradation products (see, for example, D. H. Lee et al., J. Contr. Rel., 2003, 92, 291-299). Furthermore, dependence of the release mechanism of the drug upon biodegradation may cause interpatient variability.

Alternatively, the drugs may be conjugated to a carrier through permanent covalent bonds. This approach is applied to various classes of molecules, from so-called small molecules, through natural products up to larger proteins.

Liraglutide is an example of a peptide drug that achieves an extended half-life by permanent covalent modification with a palmitoyl moiety. The fatty acid alkyl chain serves to provide albumin binding in vivo and the palmitoylated peptide forms an albumin complex that acts as a drug reservoir in the blood stream.

Albuferon is an example of a protein drug that achieves an extended half-life by permanent covalent modification with another protein that in itself has a long half-life. The corresponding fusion protein of albumin and interferon alpha, Albuferon, exhibits a significantly extended half-life as compared to interferon alpha.

Many small molecule medicinal agents, like alkaloids and anti-tumor agents, show low solubility in aqueous fluids. One way to solubilize these small molecule compounds is to conjugate the small molecule compounds to hydrophilic (water-soluble) polymers. A variety of water-soluble polymers, such as human serum albumin, dextran, lectins, poly(ethylene glycol) (PEG), poly(styrene-co-maleic anhydride), poly(N-hydroxypropylmethacrylamide), poly(divinyl ether-co-maleic anhydride), hyaluronic acid have been described for this purpose (R. Duncan, Nature Rev. Drug Disc., 2003, 2, 347-360).

Covalent modification of biological molecules with poly (ethylene glycol) has been extensively studied since the late 1970s. So-called PEGylated proteins have shown improved therapeutic efficacy by increasing solubility, reducing immunogenicity, and increasing circulation half-live in vivo due to reduced renal clearance and proteolysis by enzymes (see, for example, Caliceti P., Veronese F. M., Adv. Drug Deliv. Rev. 2003, 55, 1261-1277).

However, many biological molecules such as IFN alfa 2, saquinavir or somatostatin are inactive or show decreased biological activity when a carrier is covalently conjugated to the drug (T. Peleg-Shulman et al., J. Med. Chem., 2004, 47, 4897-4904).

In order to avoid shortcomings imposed by either the non-covalent polymer mixtures or the permanent covalent attachment, it may be preferable to employ a prodrug approach for chemical conjugation of the drug to the polymer carrier. In such polymeric prodrugs, the biologically active moieties (drugs, therapeutic, biological molecule, etc.) are typically linked to the polymeric carrier moiety by a temporary bond formed between the carrier moiety and a hydroxy, amino or carboxy group of the drug molecule.

Prodrugs are therapeutic agents that are almost inactive per se but are predictably transformed into active molecular entities (see B. Testa, J. M: Mayer in Hydrolysis in Drug and Prodrug Metabolism, Wiley-VCH, 2003, page 4). The carrier prodrug approach may be applied in such a fashion that the drug is released in vivo from the polymer in order to regain its biological activity. The reduced biological activity of the prodrug as compared to the released drug is of advantage if a slow or controlled release of the drug is desired. In this case, a relatively large amount of prodrug may be administered without concomitant side effects and the risk of overdosing. Release of the drug occurs over time, thereby reducing the necessity of repeated and frequent administration of the drug.

Prodrug activation may occur by enzymatic or non-enzymatic cleavage of the temporary bond between the carrier and the drug molecule, or a sequential combination of both, i.e. an enzymatic step followed by a non-enzymatic rearrangement. In an enzyme-free in-vitro environment such as an aqueous buffer solution, a temporary bond such as an ester or amide may undergo hydrolysis, but the corresponding rate of hydrolysis may be much too slow and thus outside the therapeutically useful range. In an in vivo environment, esterases or amidases are typically present and the esterases and amidases may cause significant catalytic acceleration of the kinetics of hydrolysis from twofold up to several orders of magnitude (see, for example, R. B. Greenwald et al. J. Med. Chem. 1999, 42 (18), 3857-3867).

Prodrugs fall in two classes, bioprecursors and carrier-linked prodrugs. Bioprecursors do not contain a carrier group and are activated by the metabolic creation of a functional group. In carrier-linked prodrugs the active substance is linked to a carrier moiety by a temporary linkage. The carrier may be biologically inert (for instance PEG) or may have targeting properties (for instance antibodies). This invention is concerned with polymeric carrier-linked or macromolecular prodrugs, where the carrier itself is a macromolecule such as a carrier protein or polysaccharide or poly(ethylene glycol).

Cleavage of a carrier prodrug generates a molecular entity (drug) of increased bioactivity and at least one side product, the carrier. After cleavage, the bioactive entity will reveal at least one previously conjugated and thereby protected functional group, and the presence of this group typically contributes to the drug's bioactivity.

In order to implement a prodrug strategy, at least one selected functional group in the drug molecule is employed for attachment of the carrier polymer. Preferred functional groups are hydroxyl or amino groups. Consequently, both the attachment chemistry and hydrolysis conditions depend on the type of functional group employed.

Numerous macromolecular prodrugs are described in the literature where the temporary linkage is a labile ester bond. In theses cases, the functional group provided by the bioactive entity is either a hydroxyl group or a carboxylic acid (e.g. Y. Luo, M R Ziebell, G D Prestwich, "A Hyaluronic Acid—Taxol Antitumor Bioconjugate Targeted to Cancer Cells", Biomacromolecules 2000, 1, 208-218, J Cheng et al, Synthesis of Linear, beta-Cyclodextrin Based Polymers and Their Camptothecin Conjugates, Bioconjugate Chem. 2003, 14, 1007-1017, R. Bhatt et al, Synthesis and in Vivo Antitumor Activity of Poly(L-glutamic acid) Conjugates of 20(S)-Camptothecin, J. Med. Chem. 2003, 46, 190-193; R. B. Greenwald, A. Pendri, C. D. Conover, H. Zhao, Y. H. Choe, A. Martinez, K. Shum, S. Guan, J. Med. Chem., 1999, 42, 3657-3667; B. Testa, J. M: Mayer in Hydrolysis in Drug and Prodrug Metabolism, Wiley-VCH, 2003, Chapter 8).

Especially for therapeutic biomacromolecules but also for certain small molecule drugs, it may be desirable to link the carrier to amino groups of the bioactive entity (i.e. N-terminus or lysine amino groups of proteins). This will be the case if masking the drug's bioactivity requires conjugation of a certain amino group of the bioactive entity, for instance an amino group located in an active center or a region or epitope involved in receptor binding. Also, during preparation of the prodrug, the amino groups may be more chemoselectively addressed and serve as a better handle for conjugating the carrier and the drug because of their greater nucleophilicity as compared to hydroxylic or phenolic groups. This is particularly true for proteins and peptides which may contain a great variety of different reactive functionalities, where non-selective conjugation reactions lead to undesired product mixtures which require extensive characterization or purification and may decrease reaction yield and therapeutic efficiency of the product.

Amide bonds are usually much more stable against hydrolysis than ester bonds, and the rate of clevage of the amide bond would be too slow for therapeutic utility in a carrier-linked prodrug. Therefore it is advantageous to add structural chemical components such as neighbouring groups in order to exert control over the cleavability of the prodrug amide bond. Such additional cleavage-controlling chemical structures that are provided neither by the carrier entity nor by the drug are termed "linkers". Prodrug linkers can have a strong effect on the rate of hydrolysis of a given temporary bond. Variation of the chemical nature of these linkers allows the engineering of the properties of the linker to a great extent.

Several examples have been published of the prodrug activation of amine-containing biologically active moieties by specific enzymes for targeted release. A prerequisite for enzymatic dependence is that the structure of the linker displays a structural motif that is recognized as a substrate by a corresponding endogenous enzyme. In these cases, the cleavage of the temporary bond occurs in a one-step process which is catalyzed by the enzyme. G. Cavallaro et al. (Bioconjugate Chem. 2001, 12, 143-151) describe the enzymatic release of an antitumoral agent by the protease plasmin. Cytarabin is coupled via the tripeptide sequence D-Val-Leu-Lys to the polymer alpha, beta-poly(N-hydroxyethyl)-DL-aspartamide (PHEA). Enzymatic release of cytarabin is effected by the protease plasmin which concentration is relatively high in various kinds of tumor mass.

Enzyme-catalyzed acceleration of prodrug cleavage is a desirable feature for organ or cellular targeting applications. Targeted release of the bioactive entity is effected, only if an enzyme, that selectively cleaves the linkage, is specifically present in the organ or cell-type chosen for treatment.

A major drawback of predominantly enzymatic cleavage is interpatient variability. Enzyme levels may differ significantly between individuals resulting in biological variation of prodrug activation by the enzymatic cleavage. The enyzme levels may also vary depending on the site of administration. For instance it is known that in the case of subcutaneous injection, certain areas of the body yield more predictable therapeutic effects than others. To reduce this unpredictable effect, non-enzymatic cleavage or intramolecular catalysis is of particular interest (see, for example, B. Testa, J. M: Mayer in Hydrolysis in Drug and Prodrug Metabolism, Wiley-VCH, 2003, page 5).

Furthermore, it is difficult to establish an in vivo-in vitro correlation of the pharmacokinetic properties for enzyme-dependent carrier-linked prodrugs. In the absence of a reliable in vivo-in vitro correlation optimization of a release profile becomes a cumbersome task.

Other carrier prodrugs employing temporary linkages to amino groups present in the drug molecule are based on a cascade mechanism. Cascade cleavage is enabled by linker compounds that are composed of a structural combination of a masking group and an activating group. The masking group is attached to the activating group by means of a first temporary linkage such as an ester or a carbamate. The activating group is attached to an amino-group of the drug molecule through a second temporary linkage, for instance a carbamate. The stability or susceptibility to hydrolysis of the second temporary linkage (e.g. carbamate) is dependent on the presence or absence of the masking group. In the presence of the masking group, the second temporary linkage is highly stable and unlikely to release the drug with therapeutically useful kinetics. In the absence of the masking group, this linkage becomes highly labile, causing rapid cleavage and drug release.

The cleavage of the first temporary linkage is the rate-limiting step in the cascade mechanism. This first step may induce a molecular rearrangement of the activating group such as a 1,6-elimination. The rearrangement renders the second temporary linkage so much more labile that its cleavage is induced. Ideally, the cleavage rate of the first temporary linkage is identical to the desired release rate for the drug molecule in a given therapeutic scenario. Furthermore, it is desirable that the cleavage of the second temporary linkage is substantially instantaneous after its lability has been induced by cleavage of the first temporary bond.

Examples of polymeric prodrugs based on 1,6-elimination have been described by R. B. Greenwald et al. J. Med. Chem., 1999, 42, 3657-3667 & PCT Patent Application WO-A-99/30727, F. M. H. DeGroot et al. (WO-A 02/83180 and WO-A 04/43493A1), and D. Shabat et al. (WO-A 04/19993).

Examples of polymeric amino-containing prodrugs based on trimethyl lock lactonization were described by R. B. Greenwald et al. J. Med. Chem. 2000, 43 (3), 457-487; PCT Patent Application No. WO-A-02/089789). In this prodrug system, substituted o-hydroxyphenyl-dimethylpropionic acid is linked to PEG by an ester, carbonate, or carbamate group as a first temporary linkage and to amino groups of drug molecules by means of an amide bond as second temporary linkage. The rate-determining step in drug release is the enzymatic cleavage of the first linkage. This step is followed by fast amide cleavage by lactonization, liberating an aromatic lactone side product.

The disadvantage in the abovementioned prodrug systems described by Greenwald, DeGroot and Shabat is the release of highly reactive and potentially toxic aromatic small molecule side products like quinone methides or aromatic lactones after cleavage of the temporary linkage. The potentially toxic entities are released in a 1:1 stoichiometry with the drug and can assume high in vivo concentrations.

A different group of cascade produgs with aromatic activating groups based on 1,6-elimination structurally separates the masking group and the carrier. This may be achieved by employing a permanent bond between the polymer carrier and the activating group. This stable bond does not participate in the cascade cleavage mechanism. If the carrier is not serving as a masking group and the activating group is coupled to the carrier by means of a stable bond, release of potentially toxic side products such as the activating group is avoided. The stable attachment of the activating group and the polymer also suppresses the release of drug-linker intermediates with undefined pharmacology.

Antczak et al. (Bioorg Med Chem 9 (2001) 2843-48) describe a reagent which forms the basis for a macromolecular cascade prodrug system for amine-containing drug molecules. In this approach an antibody serves as the carrier, a stable bond connects the antibody to an activating group, carrying an enzymatically cleavable masking group. Upon enzymatic removal of the ester-linked masking group, a second temporary bond cleaves and releases the drug compound.

D. Shabat et al. (Chem. Eur. J. 2004, 10, 2626-2634) describe a polymeric prodrug system based on a mandelic acid activating group. In this system the masking group is linked to the activating group by a carbamate bond. The activating group is conjugated permanently to a polyacrylamide polymer via an amide bond. After enzymatic activation of the masking group by a catalytic antibody, the masking group is cleaved by cyclization and the drug is released. The activating group is still connected to the polyacrylamide polymer after drug release.

M.-R. Lee et al. describe (Angew. Chem. 2004, 116, 1707-1710) a similar prodrug system based on a mandelic acid activating group and an enzymatically cleavable ester-linked masking group.

Nevertheless, in these linkers the 1,6-elimination step still generates a highly reactive aromatic intermediate. Even if the aromatic moiety remains permanently attached to the polymeric carrier, side reactions with potentially toxic products or immunogenic effects may be caused.

For these reasons, there is a need to provide novel linker technologies for forming polymeric prodrugs of amine containing active agents using aliphatic prodrug linkers that are not enzyme-dependent and do not generate reactive aromatic intermediates during cleavage.

A. J. Garman et al. (A. J. Garman, S. B. Kalindjan, FEBS Lett. 1987, 223 (2), 361-365, 1987) use PEG5000-maleic anhydride for the reversible modification of amino groups in tissue-type plasminogen activator and urokinase. Regeneration of functional enzyme from PEG-uPA conjugate upon incubation at pH 7.4 buffer by cleavage of the maleamic acid linkeage follows first order kinetics with a half-life of 6.1 h. A disadvantage of the maleamic acid linkage is the lack of stability of the conjugate at lower pH values. This limits the applicability of the maleamic acid linkage to active agents which are stable at basic (high) pH values, as purification of the active agent polymer conjugate has to be performed under basic (high pH) conditions to prevent premature prodrug cleavage.

More recently, R. B. Greenwald et al. (Greenwald et al. J. Med. Chem. 2004, 47, 726-734 and WO-A 2004/108070) described a PEG cascade prodrug system based on N,N-bis-(2-hydroxyethyl)glycine amide (bicine) linker. In this system two PEG carrier molecules are linked via temporary bonds to a bicine molecule coupled to an amino group of the drug molecule. The first two steps in prodrug activation is the enzymatic cleavage of the first temporary linkages connecting both PEG carrier molecules with the hydroxy groups of the bicine activating group. Different linkages between PEG and bicine are described resulting in different prodrug activation kinetics. The second step in prodrug activation is the cleavage of the second temporary linkage connecting the bicine activating group to the amino group of the drug molecule. The main disadvantage of this system is the connection of the polymer to the bicine linker via temporary bonds and the slow hydrolysis rate of this second temporary bicine amide linkage (t1/2>3 h in phosphate buffer) which results in the release of a bicine-modified prodrug intermediate that may show different pharmacokinetic, immunogenic, toxicity and pharmacodynamic properties as compared to the parent native drug molecule.

Dipeptides are frequently utilized for prodrug development for targeting or targeted transport as they are substrates for enzymes or biotransport systems. Less studied is the non-enzymatic route for dipeptide prodrug formation, namely the ability to undergo intramolecular cyclization to form the corresponding diketopiperazine (DKP) and release the active drug.

Such dipeptides may be attached to a drug via ester bonds as was described for dipeptide esters of the drug paracetamol (Santos, Gomes et al Bioorganic & Medicinal Chemistry Letters, 2005). In this case, the cyclization reaction consists of a nucleophilic attack of the N-terminal amine of the peptide on the ester carbon atom to form a tetrahedral intermediate. This is followed by a proton transfer from the amine to the leaving group oxyanion with simultaneous formation of a peptide bond to give the cyclic DKP product and free drug. The reaction has been described for ester prodrugs for example for cyclosporin A (Hamel, A R; Hubler, F; Carrupt, A; Wenger, R M; Mutter, M, J. Pept. Res., vol. 63, num. 2 (2004), p. 147-154). This method is applicable to hydroxyl-containing drugs in vitro but has been found to compete with enzymatic hydrolysis of the ester bond in vivo, as corresponding dipeptide esters released paracetamol at a much faster rate than in buffer (Gomes et al, Molecules 12 (2007) 2484-2506).

The problem of susceptibility of dipeptide-based prodrugs to peptidases may be addressed by incorporating at least one non-natural amino acid in the dipeptide motif. Corresponding prodrugs of cytarabine (Wipf et al, Bioorg. Med. Chem. 4 (1996) 1585-1596) and cyclosporine A (Hamel et al, J. Peptide Res. 63 (2004) 147-154) were synthesized and tested. Still, endogenous enzymes capable of cleaving ester bonds are not limited to peptidases, and the enzyme-dependence of such prodrug cleavage still gives rise to unpredictable in vivo performance.

Enzyme-dependence by design was engineered into DKP prodrugs as described in U.S. Pat. No. 7,163,923, where dipeptide ester prodrugs were formylated at the amino terminus of the dipeptide, and enzymatic deformylation was used as a trigger to set off diketopiperazine formation and subsequent cleavage of the ester-dipeptide bond followed by drug release. Similarly, vinblastine conjugates bearing an oligopeptide were described (Brady et al, J. Med. Chem. 45 (2002) 4706-4715). Here, an octapeptide was attached by an ester linkage to the 4-hydroxyl group of vinblastine and found to undergo ester bond cleavage by DKP formation after specific enzymatic removal of the N-terminal hexapeptide.

Recently the scope of the DKP formation reaction was extended to amide prodrugs. U.S. Pat. No. 5,952,294 details prodrug activation using diketopiperazine formation for dipeptidyl amide prodrugs of cytarabine. In this case, the temporary linkage was formed between the carbonyl of a dipeptide and the aromatic amino group of cytarabine. In another study, the utility of diketopiperazine activation was demonstrated for even more stable aliphatic amide prodrugs (G. A. R. Y. Suaifan et al., Tetrahedron 62 (2006) 11245-11266). Neither of these studies teaches how a slow-release effect can be achieved for such conjugates as there is no carrier or other half-life extending moiety or functionality present in the compounds disclosed.

WO-A 2009/99763 describes dipeptide prodrugs of bioactive peptides such as GLP-1 capable of releasing the peptide through diketopiperazine formation of the dipeptidic extension. In this case, the bioactive peptide moiety may carry an additional PEG chain on one of its amino acid side chain residues to achieve extended circulation of the bioactive peptide. A significant disadvantage of this approach is that the PEG chain has to be linked to the peptide without compromising its bioactivity, and it is well known that this is difficult to achieve for many peptide-based bioactives. Furthermore, as the PEGylated peptide is bioactive, it may be expected that the dipeptidic promoiety has an effect on the peptide's bioactivity and may negatively affect its receptor binding properties. As it is well known, that many peptides may interact with more than one receptor and that sequence extensions may affect the balance of such multiple receptor binding, unpredictable in vivo performance and even side effects may occur.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

It is further noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right to disclaim, and hereby disclose a disclaimer of, any previously described product, method of making the product, or process of using the product.

SUMMARY OF THE INVENTION

Therefore, an object of the present invention is to provide carrier-linked prodrug linkers suitable for drugs containing aliphatic amine groups from which free drug is released with therapeutically useful half-lives.

This object is achieved by a polymeric prodrug or pharmaceutically acceptable salt thereof comprising a drug linker conjugate D-L, wherein D is an aliphatic amine containing biologically active moiety; and L is a non-biologically active linker containing
i) a moiety $L^1$ represented by formula (I),

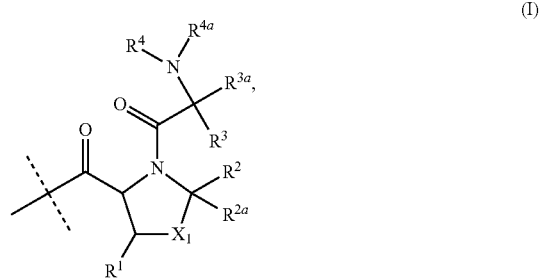

(I)

wherein the dashed line indicates the attachment of $L^1$ to an aliphatic amino group of D by forming an amide bond;

$X_1$ is selected from O, S or CH—$R^{1a}$, $R^1$ and $R^{1a}$ are independently selected from H, OH, $CH_3$ $R^2, R^{2a}, R^4$ and $R^{4a}$ are independently selected from H and $C_{1-4}$ alkyl, $R^3, R^{3a}$ are independently selected from H, $C_{1-4}$ alkyl, and $R^5$ $R^5$ is selected from

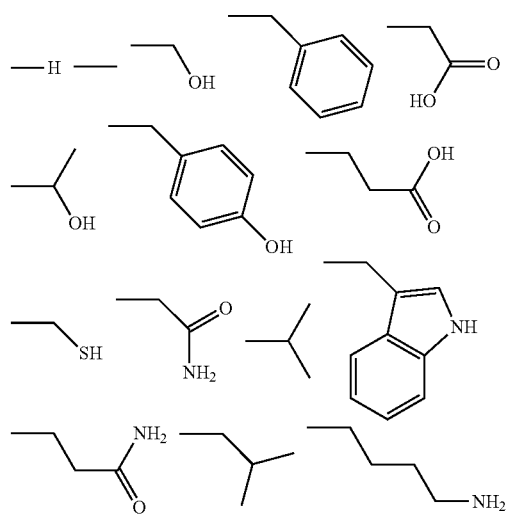

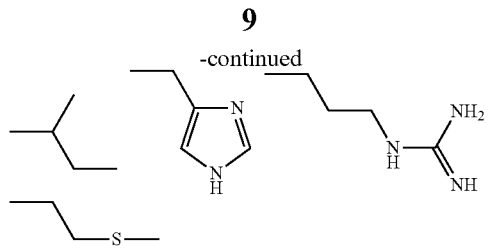

Preferably, one of the pair $R^3/R^{3a}$ is H and the other one is selected from $R^5$.

Preferably, one of $R^4/R^{4a}$ is H.

Optionally, one or more of the pairs $R^3/R^{3a}$, $R^4/R^{4a}$, $R^3/R^4$ may independently form one or more cyclic fragments selected from $C_{3-7}$ cycloalkyl, 4 to 7 membered heterocyclyl, or 9 to 11 membered heterobicyclyl.

Optionally, $R^3$, $R^{3a}$, $R^4$ and $R^{4a}$ are further substituted; Suitable substituents are alkyl (such as $C_{1-6}$ alkyl), alkenyl (such as $C_{2-6}$ alkenyl), alkynyl (such as $C_{2-6}$ alkynyl), aryl (such as phenyl), heteroalkyl, heteroalkenyl, heteroalkynyl, heteroaryl (such as aromatic 4 to 7 membered heterocycle) or halogen moieties.

ii) a moiety $L^2$, which is a chemical bond or a spacer, and $L^2$ is bound to a carrier group Z, wherein $L^1$ is substituted with one to four (preferably one) $L^2$ moieties, Z is PEG or a hydrogel, more preferably Z is a hydrogel, even more preferably Z is a PEG-based hydrogel;

optionally, L is further substituted.

Suitable substituents are alkyl (such as $C_{1-6}$ alkyl), alkenyl (such as $C_{2-6}$ alkenyl), alkynyl (such as $C_{2-6}$ alkynyl), aryl (such as phenyl), heteroalkyl, heteroalkenyl, heteroalkynyl, heteroaryl (such as aromatic 4 to 7 membered heterocycle) or halogen moieties.

The present invention addresses the disadvantages described above. The invention provides for carrier-linked prodrugs characterized by connecting a carrier via a dipeptide linker to a primary or secondary amino group of an aliphatic amine-containing drug molecule. The carrier is linked to the dipeptide linker via a permanent linkage and the bond between the dipeptide promoiety and the amine-containing drug molecule is a temporary amide linkage that exhibits extended autohydrolysis at a therapeutically useful rate at pH 7.4 and 37° C., i.e. under physiological conditions.

Due to the presence of a permanent bond between the carrier and the DKP linker, the prodrugs according to the present invention ensure release of unmodified native drug molecules from a stable conjugate comprising carrier and linker moiety.

It was now surprisingly found, that aliphatic amide bonds can undergo autohydrolysis at a rate that is useful for carrier-linked prodrug applications if cyclization-activation is used as a prodrug principle. In particular detail, it was surprisingly found that diketopiperazine formation can be used for carrier-linked amide prodrugs. Specifically, the linkers used in these carrier-linked amide prodrugs are designed such that they consist of a carrier permanently attached to a dipeptide motif in such a fashion that diketopiperazine-formation can still be employed as a self-activation principle. Suprisingly, in these linker structures, the presence of the carrier entity still allows for therapeutically useful autohydrolysis rates, an essential prerequisite for prodrug applications.

In the present application the following terms are used as described below.

"Prodrug": A prodrug is any compound that undergoes biotransformation before exhibiting its pharmacological effects. Prodrugs can thus be viewed as drugs containing specialized non-toxic protective groups used in a transient manner to alter or to eliminate undesirable properties in the parent molecule.

"Promoiety" refers to the part of the prodrug which is not the biologically active moiety. Promoiety thus refers to the linker and the carrier, if a carrier is present.

"Carrier-linked prodrug" or "carrier prodrug": A carrier-linked prodrug is a prodrug that contains a temporary linkage of a given active substance with a transient carrier group that produces improved physicochemical or pharmacokinetic properties and that can be easily removed in vivo, usually by a hydrolytic cleavage.

"Cascade prodrug": A cascade prodrug is a carrier prodrug for which the cleavage of the carrier group becomes effective only after unmasking an activating group.

"Polymeric cascade prodrug": A polymeric cascade prodrug is a carrier prodrug that contains a temporary linkage of a given active substance with a transient polymeric carrier group for which the cleavage of the carrier becomes effective only after unmasking an activating group.

"Bioprecursor prodrug": A bioprecursor prodrug is a prodrug that does not imply the linkage to a carrier group, but results from a molecular modification of the active principle itself. This modification generates a new compound, able to be transformed metabolically or chemically, the resulting compound being the active principle.

"Biotransformation": Biotransformation is the chemical conversion of substances by living organisms or enzyme preparations.

The previous definitions are based on IUPAC, as given under http://www.chem.qmul.ac.uk/iupac/medchem/ (accessed on 8 Mar. 2004)

"Linker": Cleavage-controlling chemical structures or groups present in carrier prodrugs that are not provided by either the carrier entity or by the drug.

"Sustained release" or "substained release rate" means that the administration intervals of the respective prodrug are expanded. Drugs with a daily dosage may for example be turned into a sustained release form with a week-long or even longer interval between two administrations.

A strong in vivo/in vitro correlation is observed, if the release kinetics exhibited by a hydrogel prodrug conjugate according to the present invention has a half-life in vivo that is not smaller than half the value exhibited by the same hydrogel prodrug conjugate in aqueous buffer of pH 7.4 at 37° C.

"Cis-amide conformation inducer" refers to a moiety that stabilizes the preceeding cis-amide bond. Suitable cis-amide conformation inducers are, for example, pseudoprolines.

"Aliphatic amine containing biologically active moiety D" means the part, e.g. the moiety or fragment, of the drug linker conjugate D-L, which results after cleavage in the drug D-H, the active agent, of known biological activity. In addition, the subterm "aliphatic amine containing" means that the respective moiety D and analogously the corresponding drug D-H contains at least one aliphatic fragment, and which at least one aliphatic fragment is substituted with at least one amino group.

"Non-biologically active linker" means a linker which does not show pharmacological effects.

"Biologically active moiety D" means the part of the drug linker conjugate, which results after cleavage in a drug D-H of known biological activity.

Suitable carriers are polymers and can either be directly conjugated to the linker or via a non-cleavable spacer. The term "prodrug according to the invention" refers to carrier-linked prodrugs of biologically active agents, wherein the carrier is PEG or a hydrogel, preferably a PEG-based hydrogel. The terms "PEG prodrug", "PEG-linked prodrug", "hydrogel prodrug" and "hydrogel-linked prodrug" refer to prodrugs of biologically active agents transiently linked to a PEG or to a hydrogel, respectively, and are used synonymously.

The term "polyethylene glycol based" or "PEG based" as understood herein means that the mass proportion of PEG chains or in the hydrogel is at least 10% by weight, preferably at least 25%, based on the total weight of the hydrogel. The remainder can be made up of other polymers.

Such other polymers are preferably selected from the group consisting of, for example, 2-methacryloyl-oxyethyl phosphoyl cholins, hydrogels, PEG-based hydrogels, poly (acrylic acids), poly(acrylates), poly(acrylamides), poly (alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly (cyanoacrylates), poly(dimethylacrylamides), poly(esters), poly(ethylenes), poly(ethyleneglycols), poly(ethylene oxides), poly(ethyl phosphates), poly(ethyloxazolines), poly (glycolic acids), poly(hydroxyethyl acrylates), poly(hydroxyethyloxazolines), poly(hydroxymethacrylates), poly (hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly (methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, mannans, pectins, rhamnogalacturonans, starches, hydroxyalkyl starches, hydroxyethyl starches and other carbohydrate-based polymers, xylans, and copolymers thereof.

Suitable carriers can either be directly conjugated to the linker or via a non-cleavable spacer. The term "polymer prodrug" refers to carrier-linked prodrugs of a biologically active agent, wherein the carrier is a polymer.

The term polymer describes a molecule comprised of repeating structural units connected by chemical bonds in a linear, circular, branched, crosslinked or dendrimeric way or a combination thereof, which can be of synthetic or biological origin or a combination of both. Typically, a polymer has a molecular weight of at least 1 kDa.

More preferably, Z is a biodegradable polyethylene glycol based water-insoluble hydrogel.

The term "water-insoluble" refers to a swellable three-dimensionally crosslinked molecular network forming the hydrogel. The hydrogel if suspended in a large surplus of water or aqueous buffer of physiological osmolality may take up a substantial amount of water, e.g. up to 10-fold on a weight per weight basis, and is therefore swellable but after removing excess water still retains the physical stability of a gel and a shape. Such shape may be of any geometry and it is understood that such an individual hydrogel object is to be considered as a single molecule consisting of components wherein each component is connected to each other component through chemical bonds.

The term "PEG" or "pegylation residue" is used herein exemplary for suitable water-soluble polymers characterized by repeating units. Suitable polymers may be selected from the group consisting of polyalkyloxy polymers, hyaluronic acid and derivatives thereof, polyvinyl alcohols, polyoxazolines, polyanhydrides, poly(ortho esters), polycarbonates, polyurethanes, polyacrylic acids, polyacrylamides, polyacrylates, polymethacrylates, polyorganophosphazenes, polysiloxanes, polyvinylpyrrolidone, polycyanoacrylates, and polyesters. Preferred are polyalkyloxy polymers, especially polyethylene glycol polymers containing at least 10% by weight ethylene oxide units, more preferably at least 25% by weight, even more preferably at least 50% by weight A "hydrogel" may be defined as a three-dimensional, hydrophilic or amphiphilic polymeric network capable of taking up large quantities of water. The networks are composed of homopolymers or copolymers, are insoluble due to the presence of covalent chemical or physical (ionic, hydrophobic interactions, entanglements) crosslinks. The crosslinks provide the network structure and physical integrity. Hydrogels exhibit a thermodynamic compatibility with water which allows them to swell in aqueous media. The chains of the network are connected in such a fashion that pores exist and that a substantial fraction of these pores are of dimensions between 1 nm and 1000 nm.

"Free form" of a drug refers to the drug in its unmodified, pharmacologically active form, such as after being released from a polymer conjugate.

The terms "drug", "biologically active molecule", "biologically active moiety", "biologically active agent", "active agent", and the like mean any substance which can affect any physical or biochemical properties of a biological organism, including but not limited to viruses, bacteria, fungi, plants, animals, and humans. In particular, as used herein, biologically active molecules include any substance intended for diagnosis, cure, mitigation, treatment, or prevention of disease in humans or other animals, or to otherwise enhance physical or mental well-being of humans or animals.

The terms "spacer" or "spacer moieties" refer to any moiety suitable for connecting two moieties, such as $C_{1-50}$ alkyl, $C_{2-50}$ alkenyl or $C_{2-50}$ alkinyl, which fragment is optionally interrupted by one or more groups selected from —NH—, —N($C_{1-4}$ alkyl)-, —O—, —S—, —C(O)—, —C(O)NH—, —C(O)N($C_{1-4}$ alkyl)-, —O—C(O)—, —S(O)—, —S(O)$_2$—, 4 to 7 membered heterocyclyl, phenyl or naphthyl.

"Functional groups" mean groups of atoms within molecules that exhibit a specific chemical activity. Examples are amides, amines, alcohols, carbonyls, carboxylic acids, thiols.

"Protective groups" refers to a moiety which temporarily protects a functional group of a molecule during synthesis to obtain chemoselectivity in subsequent chemical reactions. Protective groups for alcohols are, for example, benzyl and trityl, protective groups for amines are, for example, tert-butyloxycarbonyl, 9-fluorenylmethyloxycarbonyl and benzyl and for thiols examples of protective groups are 2,4,6-trimethoxybenzyl, phenylthiomethyl, acetamidomethyl, p-methoxybenzyloxycarbonyl, tert-butylthio, triphenylmethyl, 3-nitro-2-pyridylthio, 4-methyltrityl.

"Protected functional groups" means a functional group protected by a protective group.

"Acylating agent" means a moiety of the structure R—(C═O)—, providing the acyl group in an acylation reaction, optionally connected to a leaving group, such as acid chloride, N-hydroxy succinimide, pentafluorphenol and para-nitrophenol.

"Alkyl" means a straight-chain or branched carbon chain (unsubstituted alkyl). Optionally, each hydrogen of an alkyl carbon may be replaced by a substituent.

"Heteroalkyl" refers to analogs of alkyls in which one or more than one methylene group is replaced by a heteroatom, such as nitrogen, oxygen, sulfur, phosphorus, or boron. If the methylene group is replaced by nitrogen, phosphorous or boron, these heteroatoms may be further substituted. Suitable substituents are alkyl, alkenyl, alkynyl, aryl, heteroalkyl, heteroalkenyl, heteroalkynyl, heteroaryl or halogen moieties (such as those described above). The terms heteroalkenyl and heteroalkynyl are defined accordingly.

"$C_{1-4}$ alkyl" means an alkyl chain having 1 to 4 carbon atoms (unsubstituted $C_{1-4}$ alkyl), e.g. if present at the end of a molecule: methyl, ethyl, n-propyl, isopropyl, n-butyl, isobutyl, sec-butyl tert-butyl, or e.g. —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, when two moieties of a molecule are linked by the alkyl group. Optionally, each hydrogen of a $C_{1-4}$ alkyl carbon may be replaced by a substituent. Accordingly, "$C_{1-50}$ alkyl" means an alkyl chain having 1 to 50 carbon atoms. The term $C_{1-6}$ is defined accordingly.

"$C_{2-50}$ alkenyl" means a branched or unbranched alkenyl chain having 2 to 50 carbon atoms (unsubstituted $C_{2-50}$ alkenyl), e.g. if present at the end of a molecule: —$CH=CH_2$, —$CH=CH$—$CH_3$, —$CH_2$—$CH=CH_2$, —$CH=CH$—$CH_2$—$CH_3$, —$CH=CH$—$CH=CH_2$, or e.g. —$CH=CH$—, when two moieties of a molecule are linked by the alkenyl group. Optionally, each hydrogen of a $C_{2-50}$ alkenyl carbon may be replaced by a substituent as further specified. Accordingly, the term "alkenyl" relates to a carbon chain with at least one carbon carbon double bond. Optionally, one or more triple bonds may occur. The term $C_{2-6}$ alkenyl is defined accordingly.

"$C_{2-50}$ alkynyl" means a branched or unbranched alkynyl chain having 2 to 50 carbon atoms (unsubstituted $C_{2-50}$ alkynyl), e.g. if present at the end of a molecule: —$C\equiv CH$, —$CH_2$—$C\equiv CH$, $CH_2$—$CH_2$—$C\equiv CH$, $CH_2$—$C\equiv C$—$CH_3$, or e.g. —$C\equiv C$— when two moieties of a molecule are linked by the alkynyl group. Optionally, each hydrogen of a $C_{2-50}$ alkynyl carbon may be replaced by a substituent as further specified. Accordingly, the term "alkynyl" relates to a carbon chain with at lest one carbon carbon triple bond. Optionally, one or more double bonds may occur. The term $C_{2-6}$ alkynyl is defined accordingly.

"$C_{3-7}$ cycloalkyl" or "$C_{3-7}$ cycloalkyl ring" means a cyclic alkyl chain having 3 to 7 carbon atoms, which may have carbon-carbon double bonds being at least partially saturated (unsubstituted $C_{3-7}$ cycloalkyl), e.g. cyclopropyl, cyclobutyl, cyclopentyl, cyclohexyl, cyclohexenyl, cycloheptyl. Optionally, each hydrogen of a cycloalkyl carbon may be replaced by a substituent. The term "$C_{3-7}$ cycloalkyl" or "$C_{3-7}$ cycloalkyl ring" also includes bridged bicycles like norbonane (norbonanyl) or norbonene (norbonenyl). Accordingly, "$C_{3-5}$ cycloalkyl" means a cycloalkyl having 3 to 5 carbon atoms.

"Halogen" means fluoro, chloro, bromo or iodo. It is generally preferred that halogen is fluoro or chloro.

"4 to 7 membered heterocyclyl" or "4 to 7 membered heterocycle" means a ring with 4, 5, 6 or 7 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom (unsubstituted 4 to 7 membered heterocyclyl).

Examples for a 4 to 7 membered heterocycles are azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine or homopiperazine. Optionally, each hydrogen of a 4 to 7 membered heterocyclyl may be replaced by a substituent.

"9 to 11 membered heterobicyclyl" or "9 to 11 membered heterobicycle" means a heterocyclic system of two rings with 9 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom (unsubstituted 9 to 11 membered heterobicyclyl).

Examples for a 9 to 11 membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine or pteridine. The term 9 to 11 membered heterobicycle also includes spiro structures of two rings like 1,4-dioxa-8-azaspiro[4.5]decane or bridged heterocycles like 8-aza-bicyclo[3.2.1]octane. Optionally, each hydrogen of a 9 to 11 membered heterobicyclyl may be replaced by a substituent.

In case the prodrugs according to the present invention contain one or more acidic or basic groups, the invention also comprises their corresponding pharmaceutically or toxicologically acceptable salts, in particular their pharmaceutically utilizable salts. Thus, the prodrugs which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Prodrugs which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the prodrugs simultaneously contain acidic and basic groups in the molecule, the invention also includes, in addition to the salt forms mentioned, inner salts or betaines (zwitterions). The respective salts of the prodrugs of the present invention can be obtained by customary methods which are known to the person skilled in the art like, for example by contacting these with an organic or inorganic acid or base in a solvent or dispersant, or by anion exchange or cation exchange with other salts. The present invention also includes all salts of the prodrugs which, owing to low physiological compatibility, are not directly suitable for use in pharmaceuticals but which can be used, for example, as intermediates for chemical reactions or for the preparation of pharmaceutically acceptable salts.

The term "pharmaceutically acceptable" means approved by a regulatory agency, such as the EMEA (Europe) and/or the FDA (US) and/or any other national regulatory agency for use in animals, preferably in humans.

"Pharmaceutical composition" or "composition" means a composition containing one or more active ingredients, for example a drug or a prodrug, and one or more inert ingredients, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a prodrug of the present invention and a pharmaceutically acceptable excipient.

"Stable" and "stability" means that within the indicated storage time the polymer conjugates remain conjugated and do not hydrolyze to a substantial extent and exhibit an acceptable impurity profile relating to the biologically active agent. To be considered stable, the composition contains less than 10%, preferably less than 5% of the drug in its free form.

"Therapeutically effective amount" means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician. Within the scope of this invention, therapeutically effective amount relates to dosages that aim to achieve therapeutic effect for an extended period of time, i.e. for 12 hours, or 24 hours, or three days or longer, for instance one week or two weeks.

"Excipients" refers to compounds administered together with the therapeutic agent, for example, buffering agents, isotonicity modifiers, preservatives, stabilizers, anti-adsorption agents, oxidation protection agents, or other auxiliary agents. However, in some cases, one excipient may have dual or triple functions.

"Dry composition" means that the prodrug composition is provided in a dry form in a container. Suitable methods for drying are spray-drying and lyophilization (freeze-drying). Such dry composition of prodrug has a residual water content of a maximum of 10%, preferably less than 5% and more preferably less than 2% (determined according to Karl Fischer). The preferred method of drying is lyophilization.

"Lyophilized composition" means that the prodrug composition was first frozen and subsequently subjected to water reduction by means of reduced pressure. This terminology does not exclude additional drying steps which occur in the manufacturing process prior to filling the composition into the final container.

"Lyophilization" (freeze-drying) is a dehydration process, characterized by freezing a composition and then reducing the surrounding pressure and, optionally, adding heat to allow the frozen water in the composition to sublime directly from the solid phase to gas. Typically, the sublimed water is collected by desublimation.

"Reconstitution" means the addition of a liquid to bring back the original form of a composition.

"Reconstitution solution" refers to the liquid used to reconstitute the dry composition of a prodrug prior to administration to a patient in need thereof.

"Container" means any container in which the prodrug composition is comprised and can be stored until reconstitution.

"Buffer" or "buffering agent" refers to chemical compounds that maintain the pH in a desired range. Physiologically tolerated buffers are, for example, sodium phosphate, succinate, histidine, bicarbonate, citrate and acetate, sulphate, nitrate, chloride, pyruvate. Antacids such as $Mg(OH)_2$ or $ZnCO_3$ may be also used. Buffering capacity may be adjusted to match the conditions most sensitive to pH stability.

A "lyoprotectant" is a molecule which, when combined with a protein of interest, significantly prevents or reduces chemical and/or physical instability of the protein upon drying in general and especially during lyophilization and subsequent storage. Exemplary lyoprotectants include sugars, such as sucrose or trehalose; amino acids such as monosodium glutamate or histidine; methylamines such as betaine; lyotropic salts such as magnesium sulfate; polyols such as trihydric or higher sugar alcohols, e.g. glycerin, erythritol, glycerol, arabitol, xylitol, sorbitol, and mannitol; ethylene glycol; propylene glycol; polyethylene glycol; pluronics; hydroxyalkyl starches, e.g. hydroxyethyl starch (HES), and combinations thereof.

"Surfactant" refers to wetting agents that lower the surface tension of a liquid.

"Isotonicity modifiers" refer to compounds which minimize pain that can result from cell damage due to osmotic pressure differences at the injection depot.

The term "stabilizers" refers to compounds used to stabilize the polymer prodrug. Stabilisation is achieved by strengthening of the protein-stabilising forces, by destabilisation of the denatured state, or by direct binding of excipients to the protein.

"Anti-adsorption agents" refers to mainly ionic or nonionic surfactants or other proteins or soluble polymers used to coat or adsorb competitively to the inner surface of the composition's container. Chosen concentration and type of excipient depends on the effect to be avoided but typically a monolayer of surfactant is formed at the interface just above the CMC value.

"Oxidation protection agents" refers to antioxidants such as ascorbic acid, ectoine, glutathione, methionine, monothioglycerol, morin, polyethylenimine (PEI), propyl gallate, vitamin E, chelating agents such aus citric acid, EDTA, hexaphosphate, thioglycolic acid.

"Antimicrobial" refers to a chemical substance that kills or inhibits the growth of microorganisms, such as bacteria, fungi, yeasts, protozoans and/or destroys viruses.

"PEG based" as understood herein means that the mass proportion of PEG chains in the hydrogel is at least 10% by weight, preferably at least 25%, based on the total weight of the hydrogel. The remainder can be made up of other spacers and/or oligomers or polymers, such as oligo- or polylysines.

The term "hydrolytically degradable" or "biodegradable" refers within the context of the present invention to linkages which are non-enzymatically hydrolytically degradable under physiological conditions (aqueous buffer at pH 7.4, 37° C.) with half-lives ranging from one hour to three months, include, but are not limited to, aconityls, acetals, carboxylic anhydrides, esters, imines, hydrazones, maleamic acid amides, ortho esters, phosphamides, phosphoesters, phosphosilyl esters, silyl esters, sulfonic esters, aromatic carbamates, combinations thereof, and the like. Preferred biodegradable linkages are esters, carbonates, phosphoesters and sulfonic acid esters and most preferred are esters or carbonates. It is understood that for in vitro studies accelerated conditions like, for example, pH 9, 37° C., aqueous buffer, may be used for practical purposes.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

In the present invention, the hydrolytic lability required for a temporary linkage may be introduced into the prodrug amide bond by selecting the structural properties of the linker for cyclization activation. In cyclization-activated amide bond cleavage, the cleavage products are a free amine as part of the biologically active moiety and a cyclized residue. The linker structures of the present invention are designed such that highly stable rings are formed as cleavage products and the hydrolysis of the prodrug amide bond facilitates hydrolysis in a time range useful for drug delivery under physiological conditions. Preferred cyclic cleavage products are diketopiperazine rings. Prerequisite for such cyclization activation is the presence of an amine-containing nucleophile in the linker structure and another amide bond which is not the temporary amide prodrug bond but a permanent amide bond. Preferably, such linker structures contain a cis-amide conformation inducer. Alternatively, the cleavage might occur through intramolecular catalysis caused by neighbouring group effects.

In case of diketopiperazine-activated prodrug cleavage, the amine-containing nucleophile serves to attack the prodrug amide carbonyl group and consequently induces transamidation, and the permanent amide bond serves to form a stabilized six-membered ring structure.

The formation of the stabilized six-membered ring structure is facilitated through a cis-amide conformation inducing pseudoproline. Pseudoprolines are artificially created dipeptides, which contain an oxazolidine or thiazolidine ring. In peptide synthesis, pseudoprolines are used to increase solvation and solubility. Due to the preference for a cis-amide bond with the preceding residue of C2-substituted pseudoprolines, their incorporation results in a kink conformation of the peptide backbone which decreases aggregation, self-association and β-structure formation.

Preferred linker structures are composed of a dipeptide promoiety conjugated through a permanent linkage to a polymer carrier. Corresponding prodrugs are composed of a dipeptide containing a permanent linkage to a polymer carrier and a temporary amide bond to an aliphatic amino-group-containing drug.

Preferably, linkers of the present invention have a hydrolysis rate between 1 h and 2 years at pH 7.4 and 37° C. and hydrolysis rates in buffer and plasma are essentially identical, i.e. the hydrolysis rates exhibit a strong in vivo/in vitro correlation.

Preferably, D-H is a small molecule bioactive agent or a biopolymer.

Preferably, D-H is a biopolymer selected from the group of biopolymers consisting of proteins, polypeptides, oligonucleotides, and peptide nucleic acids.

"Oligonucleotides" means either DNA, RNA, single-stranded or double-stranded, siRNA, miRNA, aptamers, and any chemical modifications thereof with preferably 2 to 1000 nucleotides. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping and change of stereochemistry.

Preferably, D-H is a polypeptide selected from the group of polypeptides consisting of ACTH, adenosine deaminase, agalsidase, alfa-1 antitrypsin (AAT), alfa-1 proteinase inhibitor (API), alteplase, amylins (amylin, symlin), anistreplase, ancrod serine protease, antibodies (monoclonal or polyclonal, and fragments or fusions), antithrombin III, antitrypsins, aprotinin, asparaginases, atosiban, biphalin, bivalirudin, bone-morphogenic proteins, bovine pancreatic trypsin inhibitor (BPTI), cadherin fragments, calcitonin (salmon), collagenase, complement C1 esterase inhibitor, conotoxins, cytokine receptor fragments, DNase, dynorphine A, endorphins, enfuvirtide, enkephalins, erythropoietins, exendins, factor VII, factor VIIa, factor VIII, factor VIIIa, factor IX, fibrinolysin, fibroblast growth factor (FGF), growth hormone releasing peptide 2 (GHRP2), fusion proteins, follicle-stimulating hormones, gramicidin, ghrelin, desacyl-ghrelin, granulocyte colony stimulating factor (G-CSF), galactosidase, glucagon, glucagon-like peptides, glucocerebrosidase, granulocyte macrophage colony stimulating factor (GM-CSF), human heat shock proteins (HSP), phospholipase-activating protein (PLAP), gonadotropin chorionic (hCG), hemoglobins, hepatitis B vaccines, hirudin, human serine protease inhibitor, hyaluronidases, idurnonidase, immune globulins, influenza vaccines, interleukins (1 alfa, 1 beta, 2, 3, 4, 6, 10, 11, 12, 13, 21), IL-1 receptor antagonist (rhIL-1ra), insulins, insulin like growth factors, insulin-like growth factor binding protein (rhIGFBP), interferons (alfa 2a, alfa 2b, alfa 2c, beta 1a, beta 1b, gamma 1a, gamma 1b), intracellular adhesion molecule, keratinocyte growth factor (KGF), P-selectin glycoprotein ligand (PSGL), transforming growth factors, lactase, leptin, leuprolide, levothyroxine, luteinizing hormone, lyme vaccine, natriuretic peptides (ANP, BNP, CNP and fragments), neuropeptide Y, pancrelipase, pancreatic polypeptide, papain, parathyroid hormone, PDGF, pepsin, peptide YY, platelet activating factor acetylhydrolase (PAF-AH), prolactin, protein C, thymalfasin, octreotide, secretin, sermorelin, soluble tumor necrosis factor receptor (TNFR), superoxide dismutase (SOD), somatropins (growth hormone), somatoprim, somatostatin, streptokinase, sucrase, terlipressin, tetanus toxin fragment, tilactase, thrombins, thymosin, thyroid stimulating hormone, thyrotropin, tumor necrosis factor (TNF), TNF receptor-IgG Fc, tissue plasminogen activator (tPA), TSH, urodilatin, urate oxidase, urokinase, vaccines, vascular endothelial growth factor (VEGF), vasoactive intestinal peptide, vasopressin, ziconotide, lectin and ricin.

Preferably, D-H is a protein prepared by recombinant DNA technologies.

Preferably, D-H is a protein selected from the group of proteins consisting of antibodies, antibody fragments, single chain antigen binding proteins, catalytic antibodies and fusion proteins.

More preferably, D-H is a protein selected from the group of proteins consisting of antibody fragments, single chain antigen binding proteins, catalytic antibodies and fusion proteins.

Preferably, D-H is a small molecule bioactive agent selected from the group of agents consisting of central nervous system-active agents, anti-infective, anti-allergic, immunomodulating, anti-obesity, anticoagulants, antidiabetic, anti-neoplastic, antibacterial, anti-fungal, analgesic, contraceptive, anti-inflammatory, steroidal, vasodilating, vasoconstricting, and cardiovascular agents with at least one primary or secondary amino group.

Preferably, D-H is a small molecule bioactive agent selected from the group of agents containing at least one aliphatic primary amine group: (−)-Draflazine, (−)-Indocarbazostatin B, (+)-23,24-Dihydrodiscodermolide, (+)-Discodermolide, (+)—R-Pramipexole, (R)-(+)-Amlodipine, (R)-(+)-Terazosin, (R)-Ganciclovir cyclic phosphonate, (R)-Sulfinosine, (R)-Zacopride, (S)-(+)-Ketoprofen trometamol, (S)-Norfluoxetine, (S)-Oxiracetam, (S)-Sulfinosine, (S)-Zacopride hydrochloride, [111In-DTPA-Pro1,Tyr4]bombesin, [90Y]-DOTAGA-substance P, [99Tc]Demobesin 3, [99Tc]Demobesin 4, [Ala11,D-Leu15]Orexin B, [Arg(Me)$_9$]MS-10, [D11G,K26R,Y40YR]-Plectasin, [D11G,M13K,K26R,Y40YR]-Plectasin, [D9N,M13L,Q14R]-Plectasin, [D9S,Q14K,V36L]-Plectasin, [D-Tyr1,Arg(Me)9]MS-10, [D-Tyr1,AzaGly7,Arg(Me)9] MS-10, [D-Tyr1]MS-10, [Gln30]-Pancreatic polypeptide(2-36), [Glut10,Nle17,Nle30]-Pancreatic polypeptide(2-36), [Glu10]-Pancreatic polypeptide(2-36), [L17K,K30R]GLP-2 (1-33), [Leu13]-Motilin, [N5R,M13Y,N17R]-Plectasin, [Nle17,Nle30]-Pancreatic polypeptide(2-36), [psi[CH2NH]Tpg4]Vancomycin aglycon, [Ser12]-Humanin, [Trp19]MS-10, [Tyr24]-Humanin, 111In-Pentetreotide, 13-Deoxyadriamycin hydrochloride, 13-Deoxydoxorubicin hydrochloride, 17-Amino-17-demethoxygeldanamycin, 17-Aminogeldanamycin, 19-O-Methylgeldanamycin, 1-Methyl-D-tryptophan, 21-Aminoepothilone B, 2-Aminoaristeromycin, 2-Aminoneplanocin A, 3-Chloroprocainamide, 3-Deazaadenosine, 3-MATIDA, 447-480 Human alpha-fetoprotein, 4-Aminopyridine, 4-Aminosalicylic acid, 4-Chlorophenylthio-DADMe-immucillin-A, 4'-epi-Adriamycin, 4'-epi-Doxorubicin, 5,4'-Diepiarbekacin, 5-Aminosalicylic acid, 5-Aza-2'-deoxycytidine, 5-azacitidine, 5'-Homoneplanocin A, 6'-Homoneplanocin A, 8(R)-Fluoroidarubicin hydrochloride, 99mTc-c(RGDfK*)2HYNIC, 9-Aminocamptothecin, A-42867 pseudoaglycone, Abacavir succinate, Abacavir sulfate, Abanoquil mesilate, Abarelix, Acadesine, Acetyldinaline, Acetylsalicylic acid lysine salt, Aciclovir, Acriflavine, Actinomycin D, Acycloguanosine, Acyclovir, Acyclovir elaidate, Acyclovir oleate, Acyline, AD Peptide, Adamantamine hydrochloride, Adamplatin-IV, Adefovir, Adefovir dipivoxil, Ademetionine tosylate sulfate, Adenallene, Adenophostin A, Adenophostin B, Adenosine, Aerothricin 1, Aerothricin 16, Aerothricin 41, Aerothricin 45, Aerothricin 5, Aerothricin 50, Aerothricin 55, Afamelanotide, Afloqualone, Ageliferin diacetate, Ageliferin dihydrochloride, Aica-riboside, ALA hexyl ester, ALA Me ester, Aladapcin, Alamifovir, Alatrofloxacin mesilate, Albolabrin, Alendronate sodium, Alendronic acid sodium salt, Alestramustine, Alfuzosin hydrochloride, Aliskiren fumarate, Alloferon-1, Alogliptin benzoate, alpha-Difluoromethylornithine hydrochloride, alpha-Human atrial natriuretic polypeptide, alpha-Methylnorepinephrine, alpha-Methyltryptophan, Altemicidin, Alvespimycin hydrochloride, Amantadine hydrochloride, Ambasilide, Ambazone, Ambroxol nitrate, Amdoxovir, Ameltolide, Amelubant, Amezinium methylsulfate, Amfenac sodium, Amidox, Amifostine hydrate, Amikacin, Amiloride hydrochloride, Aminocandin, Aminocaproic acid, Aminoglutethimide, Aminoguanidine, Aminolevulinic acid hexyl ester, Aminolevulinic acid hydrochloride, Aminolevulinic acid methyl ester, Aminoquinuride, Aminosidine, Amisulpride, Amlexanox, Amlodipine, Amlodipine besylate, Amoxanox, Amoxicillin, Amoxicillin trihydrate, Amoxycillin trihydrate, Amphotericin, Amphotericin B, Ampicillin sodium, Amprenavir, Ampydin, Amrinone, Amrubicin hydrochloride, Amselamine hydrobromide, Amthamine, Anakinra, Anamorelin hydrochloride, Anatibant mesilate, Anginex, Angiopeptin acetate, Angiotensin II (human), Anisperimus, Antagonist-G, Antide, Antide-1, Antide-2, Antide-3, Antiflammin-1, Antiflammin-10, Antiflammin-2, Antiflammin-3, Antiflammin-4, Antiflammin-5, Antiflammin-6, Antiflammin-7, Antiflammin-8, Antiflammin-9, Antileukinate, Antocin II, Apadenoson, Apcitide technetium (99mTc), Aphidicolin glycinate, Apixaban, Aplonidine hydrochloride, Apoptozole 1, Apoptozole 1, Apoptozole 2, Apoptozole 3, Apraclonidine hydrochloride, Apricitabine, Arbekacin, Arbekacin sulfate, Arborcandin A, Arborcandin B, Arborcandin C, Arborcandin D, Arborcandin E, Arborcandin F, Arenicin, Arenicin-1, Arenicin-2, Argatroban monohydrate, Argimesna, Arginine butyrate, Argiopine, Argiotoxin-636, Argipidine, Arotinolol hydrochloride, Arterolane maleate, Asp(B14)-relaxin, Aspoxicillin, Astromicin sulfate, Atenolol, Atosiban, Atreleuton, Atrial natriuretic factor (99-126), Avizafone, Avorelin, Azacitidine, Azacytidine, Azalanstat, Azaromycin SC, Azelnidipine, Azetirelin, Azodicarbonamide, Azoxybacilin, Aztreonam, Aztreonam L-lysine, Aztreonam lysinate, Azumamide A, Baclofen, Bactobolin, Balapiravir hydrochloride, Balhimycin, Baogongteng A, Barusiban, Batracylin, Batroxostatin, Belactin A, Belactosin A, Belactosin C, Benanomicin B, Benexate cyclodextrin, Benzocaine, Besifloxacin hydrochloride, Binodenoson, Bivalirudin, Bleomycin A2 sulfate, Boceprevir, Body protection compound 15, Bogorol A, Boholmycin, Brain natriuretic peptide, Brasilicardin A, Bremelanotide, Brivanib alaninate, Brivaracetam, Brodimoprim, Bromfenac sodium, Bromhexine hydrochloride, Brostallicin hydrochloride, B-Type natriuretic peptide, Bunazosin hydrochloride, Buserelin acetate, Butabindide, Butamidine, Buteranol, Cabin 1, Caerulein diethylamine, Calcium folinate, Calcium-like peptide 1, Calcium-like peptide 2, Cambrescidin 800, Cambrescidin 816, Cambrescidin 830, Cambrescidin 844, Camostat mesilate, Camostat mesylate, Canfosfamide hydrochloride, Capadenoson, Capeserod hydrochloride, Capimorelin, Capravirine, Caprazamycin A, Caprazamycin B, Caprazamycin C, Caprazamycin E, Caprazamycin F, Capromorelin, Capsavanil, Carafiban maleate, Carbachol, Carbamazepine, Carbetocin, Carbovir, Carboxyamidotriazole, Cariporide mesilate, Carisbamate, Carnosine zinc complex (1:1), Carperitide, Carpipramine, Carumonam sodium, Caspofungin acetate, Cavtratin, Cecropin A(1-11) D(12-37), Cecropin D, Cefaclor, Cefalexin monohydrate, Cefcamate pivoxil hydrochloride, Cefcanel daloxate hydrochloride, Cefcapene pivoxil hydrochloride, Cefdaloxime, Cefdaloxime Pentexil Tosilate, Cefdinir, Cefditoren pivoxil, Cefepime, Cefetamet pivoxil, Cefetecol, Cefixime, Cefluprenam, Cefmatilen hydrochloride hydrate, Cefinenoxime hydrochloride, Cefminox sodium, Cefodizime, Cefodizime sodium, Cefoselis sulfate, Cefotaxime sodium, Cefotetan disodium, Cefotiam cilexetil, Cefotiam cilexetil hydrochloride, Cefotiam hexetil, Cefotiam hexetil hydrochloride, Cefotiam hydrochloride, Cefoxitin, Cefozopran, Cefozopran hydrochloride, Cefpirome, Cefpodoxime proxetil, Cefprenam, Cefprozil, Cefprozil monohydrate, Cefquinome, Cefsulodin sodium, Ceftaroline, Ceftazidime, Cefteram pivoxil, Ceftibuten, Ceftizoxime alapivoxil, Ceftobiprole, Ceftobiprole medocaril, Ceftrazonal bopentil, Ceftrazonal sodium, Ceftriaxone sodium, Cefuroxime, Cefuroxime axetil, Cefuroxime pivoxetil, Centanamycin, Cephalexin monohydrate, Ceranapril, Ceronapril, Cerulein, Ceruletide diethylamine, Cetefloxacin, Cetrorelix acetate, Chlorofusin, Chloroorienticin A, Chloroorienticin B, Chlorotetain, Cibrostatin 1, Ciclopiroxolamine, Cidofovir, Cilastatin sodium, Cilastatino, Cilengitide, Cimaterol, Cinitapride hygrogen tartrate, Cinnamycin, Cipamfylline, Circinamide, Cisapride hydrate, Cispentacin, Citicoline, Citrullimycine A, Cladribine, Clavanin A(K), Clavanin E(3-23), Clitocine, Clofarabine, Clopidogrel sulfate, Colivelin, Conantokin-R, Contulakin G, Cortagine, Coumamidine gamma1, Coumamidine gamma2, Cromoglycate lisetil hydrochloride, cyclic-Cidofovir, Cycloplatam, Cycloserine, Cyclotheonamide A, Cyclothialidine, Cycloviolin A, Cycloviolin B, Cycloviolin C, Cycloviolin D, Cygalovir, Cypemycin, Cysmethynil, Cystamidin A, Cystamine, Cystazosin, Cystocin, Cytallene, Cytarabine, Cytarabine ocfosfate, Cytaramycin, Cytochlor, Cytomodulin, Dabigatran, Dabigatran etexilate, DACH-Pt (II)-bis-ascorbate, Dacopafant, Dactimicin, Dactinomycin, Dactylocycline A, Dactylocycline B, DADMe-Immucillin-G, Dalargin, D-allo-Ileu3 PYY(3-36), Danegaptide hydrochloride, Daniquidone, Dapropterin dihydrochloride, Dapsone, Darbufelone mesilate, Darifenacin hydrobromide, Darinaparsin, Darunavir, Daunomycin, Daunorubicin, Davasaicin, Davunetide, D-Cycloserine, Debrisoquin sulfate, Debrisoquine sulfate, Decahydromoenomycin A, Decaplanin, Decitabine, Declopramide, Deferoxamine, Degarelix acetate, Dekafin 1, Dekafin 10, Delafloxacin, delta-Aminolevulinic acid hydrochloride, Deltibant, Deltorphin E, Denagliptin hydrochloride, Denibulin hydrochloride, Denufosol tetrasodium, Deoxymethylspergualin, Deoxynegamycin, Deoxyspergualin hydrochloride, Deoxyvariolin B, Desacetylvinblastinehydrazide/folate conjugate, Desferrioxamine, des-F-sitagliptin, Desglugastrin tromethamine, Deslorelin, Desmopressin acetate, Desulfated hirudin (54-65), Desulfated hirugen, Detiviciclovir diacetate, Dexamfetamine sulfate, Dexamphetamine sulfate, Dexelvucitabine, Dexibuprofen lysine, Dexketoprofen D,L-lysine, Dexketoprofen imidazole salt, Dexketoprofen lysine, Dexketoprofen trometamol, Dexormaplatin, Dextroamphetamine sulfate, Dextronatrin, Dezinamide, Dezocitidine, Diadenosine tetraphosphate, Diaveridine, Dichlorobenzoprim, Dicloguamine maleate, Didemnin X, Didemnin Y, Dideoxycytidine, Difurazone, Dilevalol, Dilevalol hydrochloride, Dirucotide, Disagregin, Discodermolide, Disermolide, Disitertide, Disodium pamidronate, Disopyramide phosphate, di-Val-L-dC, Docosyl cidofovir, Dolastatin 14, Dolastatin C, Donitriptan hydrochloride, Donitriptan mesilate, Doripenem, Dovitinib Lactate, Doxazosin mesylate, Doxorubicin hydrochloride, Doxycycline hyclate, Doxycycline hydrochloride ethanol hydrate, D-Penicillamine, Draflazine, Droxidopa, DTPA-adenosylcobalamin, d-trans-Tetraplatin, Dumorelin, Duramycin, Dyofin-1, Dyofin-2, Dyofin-9, Ebrotidine, Ecenofloxacin hydrochloride, Echistatin, Edotreotide yttrium, Efegatran sulfate hydrate, Eflornithine hydrochloride, Eglumegad hydrate, Eglumetad hydrate, Eicosyl cidofovir, Elacytarabine, Elaidic acid-Cytarabine, Elastatinal B, Elastatinal C, Elpetrigine, Eltrombopag olamine, Elvucitabine, Emoxyl, Emtricitabine, Enalkiren, Endothelin, Endothelin 1, Enfuvirtide, Enigmol, Eniporide mesilate, Entecavir, Enteric neural peptide, Entinostat, Epidoxorubicin, Epinastine hydrochloride, Epiprim, Epirubicin hydrochloride, Epithalon, Epofolate, Epostatin, Epsilon aminocaproic acid, Eptaplatin, Eptifibatide, Eremomycin, Eribulin mesilate, Eribulin mesylate, Erucamide, Esafloxacin hydrochloride, Eslicarbazepine acetate, Etaquine, Ethanolamine, Ethanolamine oleate, Ethiofos (former USAN), Ethyl aminobenzoate, Ethylthio-DADMe-immucillin-A, Ethynylcytidine, Etiracetam levoisomer, Etravirine, Etriciguat, Eurocin, Exalamide, Examorelin, Exatecan mesilate, Exenatide, Exenatide LAR, Exendin-4, Ezatiostat hydrochloride, Famciclovir, Famotidine, Famotidine bismuth citrate, Fampridine, Favipiravir, Feglymycin, Feglymycine, Felbamate, Felbinac lysine salt, Fenleuton, Fidarestat, Fidexaban, Filaminast, Filarizone, Fingolimod hydrochloride, Fish amunine, Flucytosine, Fludarabine phosphate, Fluorobenzyltriamterene, Fluorocytosine, Fluorominoxidil, Fluoroneplanocin A, Flupirtine maleate, Fluvirucin B2, Fluvoxamine maleate, Folinic acid, Folinic acid calcium salt, Fortimicin A, Fosamprenavir calcium, Fosamprenavir sodium, Fosaprepitant dimeglumine, Fosfomycin trometamol, Fosfomycin tromethamine, Fosteabine sodium hydrate, Fradafiban, Freselestat, Frog neuromedin U, Frovatriptan, Fudosteine, Furamidine, G1 peptide, Gabadur, Gabapentin, Gabexate mesilate, Galarubicin hydrochloride, Gallinacin 1, Gallinacin 1alpha, Gallinacin 2, Galmic, Galnon, Galparan, Gammaphos, Ganciclovir, Ganciclovir elaidic acid, Ganciclovir monophosphate, Ganciclovir sodium, Ganirelix, Ganirelix acetate, Garomefrine hydrochloride, Gemcitabine, Gemcitabine elaidate, Gemifloxacin mesilate, Gibbosin, Gilatide, Giracodazole, Girodazole, Girolline, Glaspimod, Glucagon-like peptide I (7-37), Glucosamine sulfate, Gludopa, Glufanide, Glutathione monoethyl ester, Glutathione monoisopropyl ester, Glycine-proline-Melphalan, Glycopin, Glycothiohexide alpha, Golotimod, Goralatide, Goserelin, Growth factor antagonist-116, Growth hormone releasing peptide 2, Growth Inhibitory Peptide, Guanabenz acetate, Guanadrel sulfate, Guanethidine monosulfate, Guanfacine hydrochloride, Gusperimus hydrochloride, Gusperimus trihydrochloride, Habekacin, Habekacin sulfate, Halovir A, Halovir B, Halovir C, Halovir D, Halovir E, Hayumicin B, Hayumicin C1, Hayumicin C2, Hayumicin D, Helvecardin A, Helvecardin B, Hepavir B, Heptaminol AMP amidate, Heptaplatin, Hexa-D-Arginine, Hexadecyl cidofovir, Hexadecyloxypropyl-cidofovir, Hexaminolevulinate, Hexyl aminolevulinate, Hirudin desulfated, Hirulog-1, Histamine dihydrochloride, Histaprodifen, Histrelin, Histrelin acetate, Human adrenomedullin, Human adrenomedullin (22-52), Human angiotensin II, Human corticotropin-releasing hormone, Human lactoferrin (1-11), Human proislet peptide, Human Secretin, Hydrostatin A, Hydroxyakalone, Hydroxycarbamide, Hydroxyurea, Hypeptin, Ibutamoren mesilate, Icatibant acetate, Iclaprim, Icofungipen, Idarubicin hydrochloride, Ilatreotide, Ilonidap, Imetit, Imidafenacin, Imidazenil, Imiquimod, Immunosine, Impentamine, Incyclinide, Indanocine, Indantadol hydrochloride, Indium In 111 pentetreotide, Indolicidin-11, Indolicidin-4, Indolicidin-8, Indomethacin trometamol, Indomethacin tromethamine, Indoxam, Inogatran, Insulin chain B (9-23) peptide, Intrifiban, Iobenguane[1311], Iodorubidazone (p), Iotriside, Irsogladine maleate, Isatoribine, Iseganan hydrochloride, Isepamicin sulfate, Isobatzelline A, Isobatzelline B, Isobatzelline C, Isobatzelline D, Isobutyramide, Isodoxorubicin, Isopropamide iodide <Rec INN; BAN; JAN; Ispinesib mesylate, Istaroxime, Iturelix, Janthinomycin A, Janthinomycin B, Janthinomycin C, Jaspine B, K9-Retrocyclin-1, Kahalalide F, Kaitocephalin, Kanamycin, Kanamycin A, kappa-Conotoxin P VIIA, Karnamicin B1, Kassinatuerin-1, Katanosin A, Katanosin B, Katanosin B, Ketoprofen lysine, Ketorolac trometamol, Ketorolac tromethamine, Kistamicin A, L-4-Oxalysine, Labetalol hydrochloride, Labradimil, Ladakamycin (formerly), Lagatide, Lamifiban, Lamivudine, Lamotrigine, Lanicemine 2(S)-hydroxysuccinate, Lanicemine hydrochloride, Lanomycin, Lanreotide acetate, Lanthiopeptin, Larazotide acetate, Lazabemide hydrochloride, L-DOPA 3-O-glucoside, L-DOPA 4-O-glucoside, L-Dopa methyl ester hydrochloride, L-Dopamide, Lecirelin, Leconotide, Lenalidomide, Lenampicillin hydrochloride, Leucettamine A, Leucovorin calcium, Leuprolide acetate, Leuprorelin acetate, Leurubicin, Leustroducsin A, Leustroducsin B, Leustroducsin C, Leustroducsin H, Levetiracetam, Levodopa, Levodopa 3-O-glucoside, Levodopa 4-O-glucoside, Levodopa methyl ester hydrochloride, Levofolinate calcium, Levoleucovorin calcium, Levonadifloxacin arginine salt, L-Histidinol, L-Homothiocitrulline, Liblomycin, Linagliptin, Lingual antimicrobial peptide, Linifanib, Lintopride, Liraglutide, Lirexapride, Lirimilast, Lisdexamfetamine mesilate, Lisinopril, L-Lysine-d-amphetamine dimesylate, Lobaplatin, Lobophorin A, Lobradimil, Lobucavir, Lobucavir, Lodenosine, Loloatin B, Lomeguatrib, Lometrexol, Lonafarnib, Loracarbef hydrate, Loviride, Loxoribine, L-Simexonyl homocysteine, L-Thiocitrulline, Lymphostin, Lysine acetylsalicylate, Lysobactin, Mabuterol hydrochloride, Magainin II, Makaluvamine A, Makaluvamine A, Makaluvamine B, Makaluvamine C, Managlinat dialanetil, Matristatin A2, Maxadilan, Melagatran, Melanotan, Melanotan I, Melanotan II, Melevodopa hydrochloride, Memantine hydrochloride, Memno-peptide A, Meprobamate, Meriolin-3, Mersacidin, Mesalamine, Mesalazine, Metaraminol, Metazosin, Meterelin, Metformin hydrochloride, Methotrexate, Methyl aminolevulinate, Methyl bestatin, Methyldopa, Methylthio-DADMe-immucillin-A, Metirosine, Metoclopramide hydrochloride, Metyrosine, Mexiletine hydrochloride, Micafungin sodium, Micronomicin sulfate, Midalcipran hydrochloride, Midaxifylline, Mideplanin, Midoriamin, Milacamide tartrate, Milacemide-[2H], Milnacipran hydrochloride, Minamestane, Minocycline hydrochloride, Minoxidil, Mirabegron, Miriplatin hydrate, Mitomycin, Mitomycin C, Mivazerol, Mivobulin isethionate, Mizoribine, Mocetinostat dihydrobromide, Modafinil, Modafinil sulfone, Moenomycin A chloride bismuth salt, Mofegiline, Mofegiline hydrochloride, Monamidocin, Monodansyl cadaverine, Monoethanolamine oleate, Montirelin tetrahydrate, Mosapride citrate, Moxilubant, Moxilubant maleate, Mozenavir mesilate, m-Phenylene ethynylene, mu-Conotoxin IIIA, Multiple sclerosis vaccine, muO-Conotoxin MrVIB, Muraminomicin A, Muraminomicin B, Muraminomicin C, Muraminomicin D, Muraminomicin E1, Muraminomicin E2, Muraminomicin F, Muraminomicin G, Muraminomicin H, Muraminomicin I, Muraminomicin Z1, Muraminomicin Z2, Muraminomicin Z3, Muraminomicin Z4, Muramyl dipeptide C, Mureidomycin A, Mureidomycin B, Mureidomycin C, Mureidomycin D, Muroctasin, Mycestericin E, Myriocin, Nafamostat mesilate, Nafamostat mesylate, Nafarelin acetate, Naglivan, Nagrestipen, Namitecan, Naproxen piperazine (2:1), Napsagatran, Neboglamine, Nebostinel, Nebracetam fumarate, Nelarabine, Neldazosin, Nelzarabine, Nemifitide ditriflutate, Nemonoxacin, Neoacridine, Neomycin B-arginine conjugate, Neomycin B-hexaarginine conjugate, Neomycin-acridine, Nepafenac, Nepicastat hydrochloride, Neramexane hydrochloride, Neridronate, Neridronic acid, Nesiritide, Netamiftide trifluoroacetate, Netilmicin sulfate, Neuromedin U-25, Neuropeptide S, Neutrophil-activating factor, Niacinamide, Nicotinamide, Niduline, Nisin, Nitrovin, Nocathiacin I, Nocathiacin II, Nocathiacin III, Nocathiacin IV, NO-Gabapentin, Nolatrexed dihydrochloride, NO-Mesalamine, Noraristeromycin, Nuvanil, O6-Benzylguanine, Ocimumoside A, Octacosamicin A, Octacosamicin B, Octreother, Octreotide acetate, Octreotide LAR, Oglufanide disodium, Olamufloxacin, Olamufloxacin mesilate, Olcegepant, Olradipine hydrochloride, Omaciclovir, Ombrabulin, Ombrabulin hydrochloride, omega-Conotoxin CVID, omega-Conotoxin MVIIA, Omiganan pentahydrochloride, Onnamide A, Opiorphin, Orbofiban acetate, Orienticin A, Orienticin B, Orienticin C, Orienticin D, Oritavancin, Oseltamivir carboxylate, Oseltamivir phosphate, Otamixaban, Otenabant hydrochloride, Ovothiol A, Oxaliplatin, Oxalysine-L, Oxazofurin, Oxcarbazepine, Oxiglutatione sodium, Oxiracetam, Oxolide, Oxynor, Oxyphenarsine, Oystrisin, Ozarelix, Pachastrissamine, Pachymedusa dacnicolor Tryptophyllin-1, Paecilaminol, Pafuramidine maleate, Palau'amine, Paldimycin B, Pamidronate sodium, p-Aminoclonidine hydrochloride, Pancopride, Papuamide A, Papuamide B, Papuamide C, Papuamide D, Parasin I, Parathyroid hormone (human recombinant), Paromomycin, Pasireotide, Paulomycin, Paulomycin A, Paulomycin A2, Paulomycin B, Paulomycin C, Paulomycin D, Paulomycin E, Paulomycin F, Pazufloxacin, Pazufloxacin mesilate, PEG-vancomycin, Pelagiomicin C, Peldesine, Pelitrexol, Pemetrexed disodium, Penciclovir, Penicillamine, Penicillin G procaine, Pentafuside, Pentamidine gluconate, Pentamidine isethionate, Pentamidine lactate, Peplomycin, Peptide Leucine Arginine, Peramivir, Perphenazine 4-aminobutyrate, Pexiganan acetate, Phakellistatin 5, Phe-Arg-beta-naphthylamide, Phentermine, Phortress, Phospholine, Pibutidine hydrochloride, Piceasin, Picumeterol fumarate, Pidorubicin, Pimagedine, Pimeloylanilide o-aminoanilide, Piproxen, Piracetam, Pirarubicin, Piscidin 1, Piscidin 2, Piscidin 3, Pivampicillin, Pixantrone maleate, Pluraflavin A, Pluraflavin B, Plusbacin A1, Plusbacin A2, Plusbacin A3, Plusbacin A4, Plusbacin B1, Plusbacin B2, Plusbacin B3, Plusbacin B4, PMEO-5-Me-DAPy, Pneumocandin A0, Pneumocandin B0, Pneumocandin B0 2-phosphate, Pneumocandin D0, Polaprezinc, Polydiscamide A, Polymer bound human leukocyte elastase inhibitor, Poststatin, PPI17-24, Pradefovir mesylate, Pradimicin C, Pradimicin E, Pradimicin FA-2, Pralatrexate, Pralmorelin, Pramipexole hydrochloride, Pramlintide acetate, Pranedipine tartrate, Prazosin hydrochloride, Prefolic A, Pregabalin, Preladenant, Prezatide copper acetate, Primaquine phosphate, Prinomide tromethamine, Probestin, Procainamide hydrochloride, Procaine hydrochloride, Procaine Penicillin, Pro-diazepam, Propeptin, Propeptin T, Prostatin, Protegrin IB-367, Prucalopride, Prucalopride hydrochloride, Prucalopride succinate, Pseudomycin A', Pseudomycin B', Pyloricidin B, Pymadin, Pyrazinamide, Pyrazinoylguanidine, Pyridazomycin, Pyriferone, Pyrimethamine, Pyrodach-2, Quinelorane hydrochloride, R-(+)-Aminoindane, R9K-Retrocyclin, Ragaglitazar L-arginine salt, Ralfinamide, Ramoplanin A'1, Ramoplanin A'2, Ramoplanin A'3, Ramorelix, Rat adrenomedullin, Ravidomycin N-Oxide, Razaxaban hydrochloride, Reblastatin, Receptor mediated permeabilizer, Recombinant human parathyroid hormone (1-84), Recombinant Jerdostatin, Regadenoson, Relaxin-3/INSL5 chimeric peptide, Relcovaptan, Remacemide hydrochloride, Remofovir mesylate, Resiquimod, Restricticin, Retaspimycin hydrochloride, Retigabine hydrochloride, Rhodopeptin C1, Rhodopeptin C2, Rhodopeptin C3, Rhodopeptin C4, Rhodostreptomycin A, Rhodostreptomycin B, Ribamidine hydrochloride, Ribavirin, Ribavirin eicosenate cis, Ribavirin eicosenate trans, Ribavirin elaidate, Ribavirin oleate, Rilmazafone hydrochloride dihydrate, Riluzole, Rimacalib hydrochloride, Rimeporide hydrochloride, Riociguat, Ritipenem acoxil, r-Jerdostatin, Robalzotan hydrochloride, Robalzotan tartrate hydrate, Rociclovir, Romurtide, Rotigaptide, Roxifiban acetate, Ruboxyl, Rufinamide, Rumycin 1, Rumycin 2, S(−)-Norketamine, Sabarubicin hydrochloride, Sabiporide mesilate, Safinamide mesilate, Safingol, Sagamacin, Sampatrilat, Sampirtine, Saprisartan, Sapropterin dihydrochloride, Saquinavir, Saquinavir mesilate, Sardomozide, Sardomozide hydrochloride, Satoribine, Satraplatin, Saussureamine C, Saxagliptin, Secobatzelline A, Secobatzelline B, Seglitide, Selanc, Selank, Seletracetam, Semapimod hydrochloride, Semparatide, Senicapoc, Sepimostat mesilate, Seproxetine, Seraspenide, Sermorelin, Sevelamer carbonate, Sevelamer hydrochloride, Shepherdin, Shiga vaccine, Siamycin I, Siamycin II, Sibrafiban, Sifuvirtide, Silodosin, Silver sulfadiazine, Sipatrigine, Sitafloxacin hydrate, Sitagliptin phosphate monohydrate, S-Nitrosoglutathione, Sofigatran, Sonedenoson, Sotirimod, Sparfloxacin, Sperabillin A, Sperabillin B, Sperabillin C, Sperabillin D, Sphingofungin F, Spifloxacin hydrate, Spinorphin, Spisulosine, Spisulosine 285, Squalamine lactate, Stearyl-norleucine-VIP, Streptomycin, Stressin1-A, Styloguanidine, Substance P(8-11), Sulcephalosporin, Sulfinosine, Sulfircin, Sulfostin, Sulphazocine, Sulphostin, Sultamicillin tosylate, Sunflower trypsin inhibitor-1, Surfen, Synadenol, Synguanol, Synthetic human secretin, Synthetic neutrophil inhibitor peptide, Synthetic porcine secretin, Tabilautide, Tabimorelin, Tacedinaline, Tacrine hydrochloride, Tafenoquine succinate, Tageflar, Talabostat, Talaglumetad hydrochloride, Talampanel, Talipexole dihydrochloride, Tallimustine hydrochloride, Talopterin, Talotrexin, Taltirelin, Tanespimycin, Tanogitran, Targinine, Targinine hydrochloride, Taribavirin hydrochloride, Technetium (99mTc) apcitide, Technetium (99mTc) depreotide, Technetium Tc 99m depreotide, Teicoplanin-A2-1, Teicoplanin-A2-2, Teicoplanin-A2-3, Teicoplanin-A2-3, Teicoplanin-A2-5, Telavancin hydrochloride, Telinavir, Temozolomide, Temurtide, Tenidap, Tenidap sodium, Tenofovir, Tenofovir DF, Tenofovir disoproxil fumarate, Terazosin hydrochloride, Teriparatide, Terlipressin, Tertomotide, Tetracosyl cidofovir, Tetracycline hydrochloride, Tetrafibricin, Tetrahydrobiopterin, Texenomycin A, Textilinin-1, Tezacitabine, TGP, Thanatin, Theprubicin, Thermozymocidin, Thioacet, Thiothio, Thr10-Contulakin G, Thrazarine, Thymalfasin, Thymic humoral factor gamma-2, Thymoctonan, Thymopentin, Thymosin alpha 1, Tiamdipine, Tifuvirtide, Tigecycline, Tigilcycline, Tilarginine hydrochloride, Timirdine diethanesulfonate, Timodepressin, Timogen, Tipifarnib, Tiplimotide, TNF-alpha protease enzyme inhibitor, Tobramycin, Tocamide hydrochloride, Tokaramide A, Tomopenem, Topostatin, Torcitabine, Tosufloxacin, Tosufloxacin tosilate, Tranexamic acid, Trantinterol hydrochloride, Tranylcypromine sulfate, Trelanserin, Tresperimus triflutate, Tribavirin, Trichomycin A, Triciribine, Triciribine phosphate, Triciribine-5'-monophosphate, Trientine hydrochloride, Trimazosin hydrochloride, Trimetrexate glucuronate, Trimexautide, Trimidox, Triplatin tetranitrate, Triproamylin acetate, Trovafloxacin, Trovafloxacin hydrate, Trovafloxacin hydrochloride mesylate, Trovafloxacin mesilate, Trovafloxacin mesylate, Troxacitabine, Trybizine hydrochloride, Tubastrine ((+)-enantiomer), Tuftsin, Tumor necrosis factor-alpha protease inhibitor, Tyroservaltide, Tyroservatide, Tyrphostin 47, Tyrphostin AG-213, Ubenimex, Ubenimex methyl ester, Ubestatin, Ubidine, Uroguanylin, Valaciclovir, Valacyclovir, ValboroPro, Valganciclovir hydrochloride, Valnemulin, Valomaciclovir stearate, Valonomycin A, Valonomycin B, Valopicitabine, Valpromide, Valrocemide, Vamicamide, Vancomycin hydrochloride, Vancoresmycin, Vapitadine hydrochloride, Varespladib, Varespladib methyl, Varespladib mofetil, Vasonatrin peptide, Velnacrine maleate, Venorphin, Vesiculin, Vigabatrin, Vilazodone hydrochloride, Vindesine, Viramidine hydrochloride, Viranamycin-B, Virgisin-1, Virgisin-2, Vitamin B3, W Peptide, Xemilofiban, Xenoxin-1, Xenoxin-2, Xenoxin-3, Xylocydine, Yttrium-90 edotreotide, Zalcitabine, Zanamivir, Ziconotide, Zileuton, Zofenoprilat arginine, Zoniporide hydrochloride, Zorubicin hydrochloride, Preferably, D-H is a small molecule bioactive agent selected from the group of agents containing at least one aliphatic secondary amine group: (−)-2-(2-Bromohexadecanoyl)paclitaxel, (−)-3-O-Acetylspectaline hydrochloride, (−)-3-O-tert-Boc-spectaline hydrochloride, (−)-Bemoradan, (−)-Bupivacaine hydrochloride, (−)-Calicheamicinone, (−)-Cicloprolol, (−)-Conophylline, (−)-Draflazine, (−)-Efaroxan, (−)-Halofenate, (−)-Indocarbazostatin B, (−)-Nebivolol, (−)-Norchloro-[18F]fluoro-homoepibatidine, (−)-Salbutamol hydrochloride, (−)-Salmeterol, (−)-Ternatin, (+)-(S)-Hydroxychloroquine, (+)-Azacalanolide A, (+)-Efaroxan, (+)-Indocarbazostatin, (+)-Isamoltan, (+)-Pemedolac, (+)-R-Pramipexole, (+)-Scyphostatin, (+)-SNAP-7180, (+)-Sotalol, (+)-threo-Methylphenidate hydrochloride, (R)-(+)-Amlodipine, (R)-Albuterol hydrochloride, (R)-Bicalutamide, (R)-Clevidipine, (R)-Ganciclovir cyclic phosphonate, (R)-Nigulpidine hydrochloride, (R)-NSP-307, (R)-Teludipine, (R)-Thionisoxetine, (R)-Tulobuterol, (R)-Zacopride, (R,R)-Formoterol tartrate, (S)-Acetorphan, (S)-Clevidipine, (S)—N-Desmethyltrimebutine, (S)-Noremopamil, (S)-Rivoglitazone, (S)-Sotalol, (S)-Zacopride hydrochloride, [111In-DTPA-Pro1,Tyr4]bombesin, [90Y]-DOTAGA-substance P, [99Tc]Demobesin 3, [99Tc]Demobesin 4, [Ala11, D-Leu15]Orexin B, [Arg(Me)$_9$]MS-10, [D11G,K26R, Y40YR]-Plectasin, [D11G,M13K,K26R,Y40YR]-Plectasin, [D9N,M13L,Q14R]-Plectasin, [D9S,Q14K,V36L]-Plectasin, [D-Tyr1,Arg(Me)$_9$]MS-10, [D-Tyr1,AzaGly7,Arg(Me)$_9$]MS-10, [D-Tyr1]MS-10, [Gln30]-Pancreatic polypeptide(2-36), [Glut0,Nle17,Nle30]-Pancreatic polypeptide (2-36), [Glu10]-Pancreatic polypeptide (2-36), [L17K,K30R]GLP-2 (1-33), [Leu13]-Motilin, [N5R,M13Y, N17R]-Plectasin, [Nle17,Nle30]-Pancreatic polypeptide (2-36), [N-MeIle4]-cyclosporin, [psi [CH2NH]Tpg4]Vancomycin aglycon, [Ser12]-Humanin, [Trp19]MS-10, [Tyr24]-Humanin, 111In-Pentetreotide, 12'-Methylthiovinblastine dihydrochloride, 14beta-Hydroxydocetaxel, 14beta-Hydroxydocetaxel-1,14-acetonide, 14beta-Hydroxytaxotere, 15bbeta-Methoxyardeemin, 16-Aza-epothilone B, 16-Methyloxazolomycin, 17-Amino-17-demethoxygeldanamycin, 17-Aminogeldanamycin, 18-Hydroxycoronaridine, 18-Methoxycoronaridine, 19-O-Methylgeldanamycin, 1-Deoxynojirimycin, 2,7-Dibromocryptolepine, 2-Bromo-7-nitrocryptolepine, 2'-Palmitoylpaclitaxel, 3-Bromomethcathinone, 3-Chloroprocainamide, 3-Fluorothalidomide, 3-Indole, 4,5-Dianilinophthalimide, 4,6-diene-Cer, 447-480 Human alpha-fetoprotein, 4-Chlorophenylthio-DADMe-immucillin-A, 4'-Ethynylstavudine, 4-Hydroxyatomoxetine, 5,4'-Diepiarbekacin, 5-Fluorodeoxyuridine, 5-Iodofredericamycin A, 5-Methylurapidil, 5-Phenylthioacyclouridine, 6,7-Dichloroisatin 3-oxime, 6alpha-7-Epipaclitaxel, 6-Mercaptopurine, 7-Bromo-2-chlorocryptolepine, 7-Deoxytaxol, 7-Oxostaurosporine, 9,9-Dihydrotaxol, 99mTc-c(RGDfK*) 2HYNIC, 9-Nitropaullone, A-42867 pseudoaglycone, Abacavir succinate, Abacavir sulfate, Abafungin, Abarelix, Abecarnil, Abitesartan, Acamprosate calcium, Acarbose, Acebutolol hydrochloride, Aceclofenac, Acemannan, Aceneuramic acid sodium salt, Acetamidoxolutamide, Acetaminophen, Acetazolamide, Acetohexamide, Acetorphan, Acetylcysteine, Acetyldinaline, Aciclovir, Acitazanolast, Acomustine, Acotiamide hydrochloride hydrate, Acreozast, Actarit, Actinomycin D, Actinoplanone B, Aculeacin Agamma, Acycloguanosine, Acyclovir, Acyclovir elaidate, Acyclovir oleate, Acyline, AD Peptide, Adamantyl globotriaosylceramide, Adaphostin, Adaprolol maleate, Adaprolol oxalate, Adatanserin hydrochloride, Adecypenol, Adelmidrol, Adenopeptin, Aderbasib, Adjudin, Adosopine, Adozelesin, Adrafinil, Adrogolide hydrochloride, Aerothricin 1, Aerothricin 16, Aerothricin 41, Aerothricin 45, Aerothricin 5, Aerothricin 50, Aerothricin 55, Aeruginosamide, Afamelanotide, Afeletecan hydrochloride, Afobazol, Afobazole, Agelasphin 517, Agelasphin 564, Ageliferin diacetate, Ageliferin dihydrochloride, Aglaiastatin C, Agomelatine, Alacepril, Aladapcin, Aladotril, Alatriopril, Alatrofloxacin mesilate, Albendazole, Albifylline, Albolabrin, Albuterol nitrate, Albuterol sulfate, Alchemix, Alfuzosin hydrochloride, Alinidine, Alisamycin, Aliskiren fumarate, Alizapride, Alkasar- 18, Allantoxamic acid, Alloferon-1, Allopurinol, Alminoprofen, Almitrine bismesylate, Almitrine dimesylate, Almorexant, Almotriptan, Alniditan, Aloracetam, Alosetron hydrochloride, Alosetron maleate, Aloxistatin, alpha-C-Galactosylceramide, alpha-Galactosylceramide, alpha-Galactosylceramide-BODIPY, alpha-Human atrial natriuretic polypeptide, alpha-Lactosylceramide, alpha-Methylepinephrine, alpha-Methyltryptophan, alpha-Nornicotine, alpha-Sialosylcholesterol sodium salt, Alprafenone hydrochloride, Alprenolol hydrochloride, Alprenoxime hydrochloride, Alsterpaullone, Altemicidin, Altromycin A, Altromycin C, Alvespimycin hydrochloride, Alvimopan hydrate, Amacetam hydrochloride, Amamistatin A, Amamistatin B, Ambazone, Ambroxol nitrate, Ameltolide, Amesergide, Amethocaine hydrochloride, Amfebutamone hydrochloride, Amibegron hydrochloride, Amifostine hydrate, Amiglumide, Amikacin, Amiloride hydrochloride, Amineptine, Aminocandin, Aminochinol, Aminoglutethimide, Aminoguanidine, Aminoquinol, Aminoquinuride, Amisulpride, Amitivir, Amlodipine, Amlodipine besylate, Amobarbital, Amocarzine, Amodiaquine, Amosulalol hydrochloride, Amoxapine, Amoxicillin, Amoxicillin trihydrate, Amoxycillin trihydrate, Ampicillin sodium, Ampiroxicam, Amprenavir, Amrinone, Amsacrine, Amsilarotene, Amsulosin hydrochloride, Amtolmetin guacil, Amylobarbitone, Anabasine hydrochloride, Anagrelide hydrochloride, Anakinra, Anamorelin hydrochloride, Anandamide, Anatibant mesilate, Andolast, Androxolutamide, Anginex, Angiopeptin acetate, Angiotensin II (human), Anidulafungin, Anisperimus, Ansamycin, Antagonist-G, Antide, Antide-1, Antide-2, Antide-3, Antiflammin-1, Antiflammin-10, Antiflammin-2, Antiflammin-3, Antiflammin-4, Antiflammin-5, Antiflammin-6, Antiflammin-7, Antiflammin-8, Antiflammin-9, Antileukinate, Antimycin All, Antimycin A12, Antimycin A13, Antimycin A14, Antimycin A15, Antimycin A16, Antocin II, Apadenoson, Apadoline, Apalcillin sodium, Apaxifylline, Apcitide technetium (99mTc), Apicularen A, Apicularen B, Apilimod, Apilimod mesylate, Apiodionene, Aplaviroc hydrochloride, Aplidine, Aplindore fumarate, Aplonidine hydrochloride, Apoptozole 1, Apoptozole 2, Apraclonidine hydrochloride, Apremilast, Aprepitant, Aprikalim, Aprosulate sodium, Aptiganel, Aranidipine, Aranorosin, Aranorosinol A, Aranorosinol B, Aranose, Aranoza, Araprofen, Arbaclofen placarbil sodium, Arbekacin, Arbekacin sulfate, Arborcandin A, Arborcandin B, Arborcandin C, Arborcandin D, Arborcandin E, Arborcandin F, Arbutamine hydrochloride, Archazolid A, Archazolid B, Archazolide A, Arcyriacyanin A, Ardeemin, Arenicin, Arenicin-1, Arenicin-2, Arformoterol tartrate, Argatroban monohydrate, Argimesna, Arginine butyrate, Argiopine, Argiotoxin-636, Argipidine, Argyrin A, Argyrin B, Arhalofenate, Aripiprazole, Arisostatin A, Arofylline, Arotinolol hydrochloride, Arterolane maleate, Artilide fumarate, Ascosalipyrrolidinone A, Ascosalipyrrolidinone B, Asobamast, Asp(B14)-relaxin, Asperlicin B, Asperlicin C, Asperlicin D, Asperlicin E, Aspoxicillin, Astemizole, Ataciguat, Atalaphillidine, Atalaphillinine, Ataquimast, Ataquimast hydrochloride, Atazanavir sulfate, Atenolol, Atevirdine mesylate, Atipamezole, Atizoram, Atomoxetine hydrochloride, Atorvastatin, Atorvastatin calcium, Atosiban, Atrial natriuretic factor (99-126), Aureobasidin A, Auristatin E, Auristatin PE, Avasimibe, Avicin D, Avicin G, Avitriptan, Avizafone, Avorelin, Avosentan, Avrainvillamide, Axitinib, Axitirome, AZ-36041, Azaromycin SC, Azasetron, Azasetron hydrochloride, Azathioprine, Azatoxin, Azelnidipine, Azepinostatin, Azetirelin, Azidothymidine, Azidothymidine phosphonate, Azilsartan, Azilsartan medoxomil, Aztreonam, Aztreonam L-lysine, Aztreonam lysinate, Azumamide A, Azumamide E, Bactobolin, Bafetinib, Balaglitazone, Balamapimod, Balanol, Balaperidone, Balhimycin, Balicatib, Balofloxacin, Balofloxacin dihydrate, Balsalazide disodium, Bamaquimast, Bambuterol, Bamirastine hydrate, Banoxantrone, Baogongteng A, Barixibat, Barnidipine hydrochloride, Barusiban, Basifungin, Batimastat, Batoprazine, Batroxostatin, Batzelline A, Batzelline B, Batzelline C, Beauveriolide I, Beauveriolide III, Becampanel, Becatecarin, Bederocin, Bedoradrine sulfate, Befol, Befunolol hydrochloride, Begacestat, Belactin A, Belactin B, Belactosin A, Belactosin C, Belaperidone, Belinostat, Belotecan hydrochloride, Bemoradan, Benadrostin, Benafentrine dimaleate, Benanomicin A, Benanomicin B, Benatoprazole, Benazepril hydrochloride, Bendrofluazide, Bendroflumethiazide, Benexate cyclodextrin, Benidipine hydrochloride, Benperidol, Benzimidavir, Benzylpenicillin sodium, Berlafenone hydrochloride, Besonprodil, beta-CCM, beta-Methyl-6-chloromelatonin, Betamipron, beta-Sialosylcholesterol sodium salt, beta-Tethymustine, Betaxolol hydrochloride, Bevantol hydrochloride, Bevantolol hydrochloride, Bezafibrate, Bicalutamide, Biemnidin, Bifemelane hydrochloride, Bifeprunox mesilate, Bimatoprost, Binodenoson, Binospirone mesylate, Biotinylated idraparinux, Bioxalomycin alpha 1, Bipranol hydrochloride, Bis(7)-cognitin, Bis(7)-tacrine, Bisantrene hydrochloride, Bisnafide mesilate, Bisnafide mesylate, Bisoprolol fumarate, Bitolterol mesylate, Bivalirudin, Bizelesin, Bleomycin A2 sulfate, Boc-Belactosin A, Boceprevir, Boc-Lysinated betulonic acid, Body protection compound 15, Bogorol A, Bohemine, Boholmycin, Bopindolol, Bortezomib, Bosentan, Bosutinib, Bradyzide, Brain natriuretic peptide, Brasilicardin A, Brecanavir, Bremelanotide, Brimonidine tartrate, Brinazarone, Brinzolamide, Brivanib, Brivanib alaninate, Brivudine, Bromantan, Bromantane, Bromazepam, Bromocriptine mesilate, Bromotopsentin, Bromovinyldeoxyuridine, Brostallicin hydrochloride, Brovavir, B-Type natriuretic peptide, Bucillamine, Bucladesine sodium, Buflomedil pyridoxalphosphate, Bulaquine, Bumetanide, Bupivacaine hydrochloride, Bupropion hydrochloride, Buserelin acetate, Butabindide, Buteranol, Butobarbitone, Butoctamide hemisuccinate, Butofilolol, Butyl flufenamate, Butyzamide, Cabazitaxel, Cabergoline, Cabin 1, Cadralazine, Cadrofloxacin hydrochloride, Caerulein diethylamine, Calcium folinate, Calcium-like peptide 1, Calcium-like peptide 2, Caldaret hydrate, Caldiamide sodium, Calicheamicin gamma1 aglycone, Calindol Dihydrochloride, Calothrixin A, Cambrescidin 800, Cambrescidin 816, Cambrescidin 830, Cambrescidin 844, Camostat mesilate, Camostat mesylate, Camprofen, Canadensol, Candesartan, Candesartan cilexetil, Candesartan hexetil, Candoxatril, Candoxatrilat, Canertinib dihydrochloride, Canfosfamide hydrochloride, Cangrelor tetrasodium, Capecitabine, Capimorelin, Caprazamycin A, Caprazamycin B, Caprazamycin C, Caprazamycin E, Caprazamycin F, Capridine beta, Caprolactin A, Caprolactin B, Capromorelin, Capsavanil, Capsazepine, Carabersat, Caracasanamide, Caracasandiamide, Carafiban maleate, Carbazomadurin A, Carbazomadurin B, Carbazomycin G, Carbazomycin H, Carbetocin, Carbidopa, Carbovir, Carfilzomib, Cariprazine hydrochloride, Carmethizole, Carmofur, Carmoterol hydrochloride, Carmoxirole hydrochloride, Carmustine, Carnosine zinc complex (1:1), Carperitide, Carprofen, Carquinostatin A, Carsatrin, Carteolol hydrochloride, Carteramine A, Carumonam sodium, Carvedilol, Carvotroline hydrochloride, Carzelesin, Caspofungin acetate, Catramilast, Cavtratin, Cebaracetam, Cecropin A(1-11) D(12-37), Cecropin D, Cediranib, Cefaclor, Cefalexin monohydrate, Cefazolin sodium, Cefbuperazone sodium, Cefcamate pivoxil hydrochloride, Cefcanel, Cefcanel daloxate hydrochloride, Cefcapene pivoxil hydrochloride, Cefdaloxime, Cefdaloxime Pentexil Tosilate, Cefdinir, Cefditoren pivoxil, Cefepime, Cefetamet pivoxil, Cefetecol, Cefixime, Cefluprenam, Cefmatilen hydrochloride hydrate, Cefinenoxime hydrochloride, Cefminox sodium, Cefodizime, Cefodizime sodium, Cefonicid sodium, Cefoperazone sodium, Cefoselis sulfate, Cefotaxime sodium, Cefotetan disodium, Cefotiam cilexetil, Cefotiam cilexetil hydrochloride, Cefotiam hexetil, Cefotiam hexetil hydrochloride, Cefotiam hydrochloride, Cefoxitin, Cefozopran, Cefozopran hydrochloride, Cefpimizole sodium, Cefpiramide sodium, Cefpirome, Cefpodoxime proxetil, Cefprenam, Cefprozil, Cefprozil monohydrate, Cefquinome, Cefsulodin sodium, Ceftaroline, Ceftaroline fosamil acetate, Ceftazidime, Cefteram pivoxil, Ceftibuten, Ceftizoxime alapivoxil, Ceftizoxime sodium, Ceftobiprole, Ceftobiprole medocaril, Ceftrazonal bopentil, Ceftrazonal sodium, Ceftriaxone sodium, Cefuroxime, Cefuroxime axetil, Cefuroxime pivoxetil, Celiprolol hydrochloride, Cemadotin hydrochloride, Centanamycin, Cephalexin monohydrate, Cephazolin sodium, Ceratamine A, Ceratamine B, Cerebrocrast, Cerebroside A, Cerebroside B, Cerebroside C, Cerebroside D, Cerulein, Ceruletide diethylamine, Cethromycin, Cetrorelix acetate, Cevipabulin, Chackol, Chaetocin, Chetocin, Chinoin-169, Chloptosin, Chlorazicomycin, Chlordiazepoxide hydrochloride, Chlorofusin, Chlorooorienticin A, Chlorooorienticin B, Chloropeptin II, Chlorotetain, Chlorothiazide, Chlorpropamide, Chlorpropham, Chlortalidone, Chlortenoxicam, Chlorthalidone, Chondramide A, Chondramide B, Chondramide C, Chondramide D, Cibenzoline succinate, Ciclosporin, Cifenline succinate, Cilastatin sodium, Cilastatino, Cilazapril, Cilengitide, Cilnidipine, Cilostazol, Ciluprevir, Cimadronate sodium, Cimaterol, Cimetidine, Cimetidine bismuth citrate, Cimetidine bismuth L-tartrate, Cimetidine nitrate, Cinacalcet hydrochloride, Cinaldipine, Cinalukast, Cinitapride hygrogen tartrate, Cinnabaramide A, Cinnamycin, Cinnoxicam, Cipamfylline, Cipemastat, Cipralisant, Ciprofloxacin hydrochloride, Ciprofloxacin silver salt, Ciprokiren, Ciproxifan, Circinamide, Cisapride hydrate, Citropeptin, Citrullimycine A, Clamikalant, Clausenamine A, Clavanin A(K), Clavanin E(3-23), Clazosentan, Clazosentan sodium, Clevidipine butyrate, Clevudine, Clindamycin hydrochloride, Clitocine, Clobenpropit, Clonazepam, Clonidine, Clonidine hydrochloride (hydrochloride), Clopamide, Clopenphendioxan, Clopidogrel sulfate, Cloranolol hydrochloride, Clorazepate dipotassium, Clospiramine hydrochloride, Cloturin, Clozapine, Coenzyme PQQ, Colabomycin A, Coleneuramide, Colivelin, Coluracetam, Complestatin, Conagenin, Conantokin-R, Coniosetin, Conivaptan hydrochloride, Conophylline, Contulakin G, Cortagine, Coumamidine gamma1, Coumamidine gamma2, Covidarabine, Creatine phosphate, Crilvastatin, Crisnatol mesilate, Cronidipine, Cryptophycin 52, Cyclamenol, Cyclo[His-Pro], Cyclocreatine, Cyclolinopeptide A, Cyclolinopeptide B, Cyclomarin A, Cyclopenthiazide, Cyclophosphamide, Cycloserine, Cyclosporin, Cyclosporin A, Cyclosporin J, Cyclosporine, Cyclosporine A, Cyclotheonamide A, Cyclothialidine, Cycloviolin A, Cycloviolin B, Cycloviolin C, Cycloviolin D, Cygalovir, Cymserine, Cypemycin, Cystamidin A, Cystemustine, Cystocin, Cytoblastin, Cytochalasin B, Cytomodulin, Cytotrienin A, Cytotrienin I, Cytotrienin II, Cytotrienin III, Cytotrienin IV, Cytoxazone, Dabelotine mesilate, Dabigatran, Dabigatran etexilate, Dabuzalgron hydrochloride, Dacinostat, Dactimicin, Dactinomycin, Dactylocycline A, DADMe-Immucillin-G, DADMe-Immucillin-H, Daglutril, Dalargin, Dalbavancin, Dalcetrapib, Dalcotidine, Dalfopristin mesilate, D-allo-Ileu3 PYY(3-36), DANA, Danegaptide hydrochloride, Danusertib, Dapivirine, Daporinad, Dapropterin dihydrochloride, Darbufelone, Darglitazone, Darinaparsin, Darunavir, Dasantafil, Dasatinib, Davasaicin, Davunetide, Daxalipram, D-Cycloserine, Debromoshermilamine, Decahydromoenomycin A, Decaplanin, Decatromicin A, Decatromicin B, Declopramide, Deferobiotin, Deferoxamine, Degarelix acetate, Degrasyn, Dehydrodidemnin B, Dehydrodolastatin-13, Dekafin 1, Dekafin 10, Delaminomycin A, Delaminomycin B, Delaminomycin C, Delapril hydrochloride, Delavirdine mesilate, Delfaprazine hydrochloride, Delimotecan sodium, Deltibant, Deltorphin E, Delucemine hydrochloride, Demethylallosamidin, Demethylasterriquinone B-1, Demetomidine, Demexiptiline hydrochloride, Denibulin hydrochloride, Denopamine, Denufosol tetrasodium, Deoxycoformycin, Deoxymethylspergualin, Deoxymulundocandin, Deoxynegamycin, Deoxynojirimycin, Deoxyspergualin hydrochloride, Depsipeptide, Deriglidole, Desacetylvinblastinehydrazide, Desacetylvinblastinehydrazide/folate conjugate, Desbutyl benflumetol, Desbutylhalofantrine hydrochloride, Desferri-danoxamine, Desferri-nordanoxamine, Desferrioxamine, Desferri-salmycin A, Desferri-salmycin B, Desferri-salmycin C, Desferri-salmycin D, Desglugastrin tromethamine, Desipramine hydrochloride, Desloratadine, Deslorelin, Desmin-370, Desmopressin acetate, Desulfated hirudin (54-65), Desulfated hirugen, Detomidine hydrochloride, Devazepide, Dexecadotril, Dexefaroxan, Dexfenfluramine hydrochloride, Dexketoprofen imidazole salt, Dexketoprofen meglumine, Dexlansoprazole, Dexloxiglumide, Dexmedetomidine hydrochloride, Dexmethylphenidate hydrochloride, Dexniguldipine hydrochloride, Dexpemedolac, Dexrazoxane hydrochloride, Dexsotalol, Dextronatrin, Dexylosylbenanomycin A, d-Fenfluramine hydrochloride, D-Fluviabactin, DHA-paclitaxel, Diaplasinin, Diazepinomicin, Diazoxide, Dichlorobenzoprim, Diclofenac potassium, Diclofenac sodium, Diclofenac zinc salt, Didanosine, Didemnin X, Didemnin Y, Dideoxyinosine, Diethyl-lactam, Diethylnorspermine, Difurazone, Diheteropeptin, Dihydrexidine, Dihydro-alpha-ergokryptine mesylate, Dihydroavenanthramide D, Dihydroeponemycin, Dihydroergotamine mesylate, Dilevalol, Dilevalol hydrochloride, Dimelamol, Dimethynur, Dimiracetam, di-mPEG5-Atazanavir, Dinapsoline, Dinoxyline, Dioxolane T, Dioxolane thymine nucleoside, Diperamycin, Dipivefrine hydrochloride, Dipranol hydrochloride, Diquafosol tetrasodium, Dirithromycin, Dirlotapide, Dirucotide, Disagregin, Disalazine, Discodermide, Discodermide acetate, Discorhabdin D, Discorhabdin P, Discorhabdin S, Discorhabdin T, Discorhabdin U, Disitertide, Dithiosteine, d-Methamphetamine hydrochloride, Dobutamine hydrochloride, Dobutamine phosphate, Docarpamine, Docetaxel, Docetaxol, Dofetilide, Dolasetron, Dolasetron mesilate, Dolastatin 10, Dolastatin 13, Dolastatin 14, Dolastatin 15, Dolastatin C, Dolastatin D, Domitroban calcium hydrate, Domperidone, Donitriptan hydrochloride, Donitriptan mesilate, Dopexamine, Dopexamine hydrochloride, Doramapimod, Doripenem, Dormitroban, Dorrigocin A, Dorrigocin B, Dorzolamide hydrochloride, Dovitinib Lactate, Doxifluridine, DoxoTam 12, d-Pseudoephedrine hydrochloride, Draflazine, Dronedarone hydrochloride, Droperidol, Droxinavir, d-threo-Methylphenidate hydrochloride, DTPA-adenosylcobalamin, Duloxetine hydrochloride, Dumorelin, Duocarmycin A, Duocarmycin B1, Duocarmycin B2, Duocarmycin C1, Duocarmycin C2, Duocarmycin SA, Duramycin, Dutasteride, Dynemicin A, Dynemicin C, Dyofin-1, Dyofin-2, Dyofin-9, Ebalzotan, Ebanicline, Ebrotidine, Ecadotril, Echistatin, Ecomustine, Ecteinascidin 1560, Ecteinascidin 722, Ecteinascidin 729, Ecteinascidin 736, Ecteinascidin 743, Ecteinascidin 745, Ecteinascidin 770, Ecteinascidin 875, Edaglitazone, Edonentan hydrate, Edotecarin, Edotreotide yttrium, Edoxaban tosilate, Efaproxiral sodium, Efaroxan, Efavirenz, Efegatran sulfate hydrate, Efepristin, Eflucimibe, Eflumast, Efonidipine hydrochloride ethanol, Eformoterol fumarate, Elacridar, Elagolix sodium, Elarofiban, Elastatinal B, Elastatinal C, Elbanizine, Eldacimibe, Elesclomol, Eletriptan, Elgodipine hydrochloride, Elinafide mesilate, Elinogrel potassium, Elliptinium acetate, Elliptoside A, Elliptoside E, Elnadipine, Elopiprazole, Eltrombopag olamine, Embusartan, Emicerfont, Emivirine, Emonapride, Emricasan, Enalapril maleate, Enalapril nitrate, Enalaprilat, Enalkiren, Enazadrem, Endothelin, Endothelin 1, Enfuvirtide, Eniluracil, Enkastin (D), Enkastin AD, Enkastin AE, Enkastin ID, Enkastin IE, Enkastin VD, Enkastin VE, Enocitabine, Enoxacin, Enoximone, Entecavir, Enteric neural peptide, Entinostat, Enzastaurin hydrochloride, Eperezolid, Eperezolid N-oxide, Epervudine, Epibatidine, Epidepride-(125I), Epiderstatin, Epipachysamine E, Epithalon, Epocarbazolin A, Epocarbazolin B, Epofolate, Epolactaene, Eponemycin, Epostatin, Epoxomicin, Epristeride, Eprobemide, Eprotirome, Eptastigmine tartrate, Eptifibatide, Erbulozole, Erdosteine, Eremomycin, Ergotamine tartrate, Eribaxaban, Eritoran tetrasodium, Erlosamide, Erlotinib hydrochloride, Ersentilide, Ersentilide hydrochloride, Ertapenem sodium, Erythromycin salnacedin, Erythromycin stinoprate, Esculeogenin A, Esculeoside A, Eserine salicylate, Esmolol hydrochloride, Esperamicin A1, Esperatrucin, Etacizin, Etamsylate, Etaquine, Ethacizin, Ethamsylate, Ethimizol, Ethiofos, Ethosuximide, Ethoxy-idazoxan, Ethyl loflazepate, Ethylthio-DADMe-immucillin-A, Etidocaine hydrochloride, Etodolac, Etodolic acid, Etravirine, Eugenodilol, Eurocin, Eurystatin A, Eurystatin B, Examorelin, Exenatide, Exenatide LAR, Exendin-4, Ezatiostat hydrochloride, Ezlopitant, Fabesetron, Fabesetron hydrochloride, Fadolmidine hydrochloride, Falnidamol, Famotidine bismuth citrate, Fanapanel, Farglitazar, Fasidotril, Fasobegron hydrochloride, Fasoracetam, Fasudil hydrochloride, Feglymycin, Feglymycine, Felodipine, Fenoldopam mesilate, Fenoterol hydrobromide, Fenoximone, Fepradinol, Ferrochloroquine, Ferroquine, Ferulinolol, Fidarestat, Fiduxosin hydrochloride, Filarizone, Fimasartan, Fimbrigal P, Finafloxacin hydrochloride, Finasteride, Fipamezole hydrochloride, Fish amunine, Flecamide acetate, Flibanserin, Flindokalner, Flomoxef sodium, Flopristin, Flopristine, Florbetaben, Flovagatran sodium, Floxuridine, Flucytosine, Flufenoxine, Flumezapine, Fluodipine, Fluorocytosine, Fluorofur, Fluoroindolocarbazole A, Fluoroindolocarbazole B, Fluoroindolocarbazole C, Fluorouracil, Fluoxetine hydrochloride, Fluparoxan, Flupirtine maleate, Fluspirilene, Flutamide, Fluvirucin B2, Foetidine 1, Foetidine 2, Folinic acid, Folinic acid calcium salt, Fomepizole, Fondaparin sodium, Fondaparinux sodium, Fonsartan potassium, Forasartan, Foretinib, Formobactin, Formoterol fumarate, Forodesine hydrochloride, Fosalvudine tidoxil, Fosamprenavir calcium, Fosamprenavir sodium, Fosaprepitant, Fosaprepitant dimeglumine, Fosopamine, Fosphenyloin sodium, Fostamatinib, Fostamatinib disodium, Fotemustine, Fozivudine tidoxil, Fradafiban, Franidipine hydrochloride, Freselestat, Frog neuromedin U, Frovatriptan, Frusemide, Ftorafur, Furaldipine, Furavir, Furnidipine, Furosemide, G1 peptide, Gabadur, Gabapentin enacarbil, Gabexate mesilate, Gaboxadol, Gadobenate dimeglumine, Gadobenic acid dimeglumine salt, Gadocoletic acid trisodium salt, Gadodenterate, Gadodiamide, Gadodiamide injection, Gadolinium DTPA, Gadolinium DTPA-BMA, Gadomelitol, Gadopentetate dimeglumine, Gadoterate meglumine, Gadoversetamide, Galactomycin I, Galactomycin II, Galdansetron, Gallinacin 1, Gallinacin 1alpha, Gallinacin 2, Galmic, Galnon, Galocitabine, Galparan, Gammaphos, Ganciclovir, Ganciclovir elaidic acid, Ganciclovir monophosphate, Ganefromycin alpha, Ganefromycin beta, Ganglioside GM1, Ganirelix, Ganirelix acetate, Ganstigmine hydrochloride, Gantofiban, Garenoxacin mesilate, Garomefrine hydrochloride, Gastrazole, Gastrophenzine, Gatifloxacin, Gavestinel sodium, Gedocarnil, Gefitinib, Gefitinib hydrochloride, Gemopatrilat, Gibbosin, Gidazepam, Gilatide, Gilvusmycin, Giracodazole, Giripladib, Girodazole, Girolline, Givinostat, Glaspimod, Glibenclamide, Gliclazide, Glidobactin PF-1, Glimepiride, Glipizide, Gliquidone, Glucagon-like peptide I (7-37), Glucarolactam potassium, Glucolanomycin, Gludopa, Glufanide, Glufosfamide, Glutapyrone, Glutathione monoethyl ester, Glutathione monoisopropyl ester, Glutethimide, Glyburide, Glycine-proline-Melphalan, Glycopin, Glycopril, Glycothiohexide alpha, Gold talaporfin sodium, Golotimod, Gomisin A glycinosuccinate sodium salt, Goralatide, Goserelin, Gosogliptin hydrochloride, Granisetron hydrochloride, Grepafloxacin hydrochloride, Growth factor antagonist-116, Growth hormone releasing peptide 2, Growth Inhibitory Peptide, Guanabenz acetate, Guanadrel sulfate, Guanethidine monosulfate, Guanfacine hydrochloride, Gusperimus hydrochloride, Gusperimus trihydrochloride, Gypsetin, Habekacin, Habekacin sulfate, Halimide, Halofuginone hydrobromide, Halovir A, Halovir B, Halovir C, Halovir D, Halovir E, Harkoseride, Helvecardin A, Helvecardin B, Heptaminol AMP amidate, Heptylstigmine tartrate, Herquline B, Hesperadin, Hexa-D-Arginine, Himastatin, Hirudin desulfated, Hirulog-1, Hispidospermidin, Histamine dihydrochloride, Histaprodifen, Histrelin, Histrelin acetate, Homoepibatidine, Homoindanomycin, Hormaomycin, Human adrenomedullin, Human adrenomedullin (22-52), Human angiotensin II, Human corticotropin-releasing hormone, Human lactoferrin (1-11), Human proislet peptide, Human Secretin, Hyaluronan, Hyaluronate sodium, Hydralazine hydrochloride, Hydrochlorothiazide, Hydroflumethiazide, Hydrostatin A, Hydroxyakalone, Hydroxycarbamide, Hydroxychloroquine sulfate, Hydroxymycotrienin A, Hydroxymycotrienin B, Hydroxyurea, Hymenistatin 1, Hypeptin, Ibipinabant, Ibodutant, Ibopamine, Ibrolipim, Ibutamoren mesilate, Ibutilide fumarate, Icatibant acetate, Icopezil maleate, Idazoxan hydrochloride, Idrabiotaparinux sodium, Idrapril, Ifetroban, Ifosfamide, Iganidipine hydrochloride, Iguratimod, Ilaprazole, Ilatreotide, Ilepatril, Ilomastat, Imatinib mesylate, Imetit, Imexon, Imidacrine, Imidapril, Imidapril hydrochloride, Imidazoacridinone, Imidazole 24b, Imipemide, Imipenem, Imirestat, Imisopasem manganese, Immepip, Immepyr, Immethridine, Immucillin-H, Immunosine, Imoproxifan, Impentamine, Implitapide, Improgan, Incadronate, Incadronic acid sodium salt, Indacaterol, Indanomycin, Indantadol hydrochloride, Indapamide, Indeloxazine hydrochloride, Indibulin, Indinavir sulfate, Indisetron hydrochloride, Indisulam, Indium In 111 pentetreotide, Indole-3-propionic acid, Indolicidin-11, Indolicidin-4, Indolicidin-8, Indolmycin, Indomethacin phenethylamide, Indomethacin-Simvastatin, Indoramin hydrochloride, Inogatran, Inosine pranobex, Inosiplex, Insulin chain B (9-23) peptide, Intaxel (from Himalayan Yew), Integramycin, Intoplicine, Intrifiban, Iobenguane[131I], Iobitridol, Iodixanol, Iodoproxyfan, Iodorubidazone (p), Iofetamine hydrochloride 1-123, Iofratol, Iohexyl, Iolopride (123I), Iomeprol, Iopamidol, Iopentol, Iopromide, Iotriside, Iotrol, Iotrolan, Ioversol, Ioxilan, Ioxipride, Ipazilide fumarate, Iptakalim hydrochloride, Irbesartan, Irciniastatin A, Irciniastatin B, Iroxanadine, Irtemazole, Isaglidole, Isaglitazone, Isalsteine, Isatoribine, Isavuconazonium chloride hydrochloride, Iseganan hydrochloride, Isepamicin sulfate, Isocarboxazid, Isofagomine tartrate, Isoniazid, Isoquine, Isosegoline A, Isovanihuperzine A, Ispronicline, Isradipine, Itasetron, Itopride, Itopride hydrochloride, Itriglumide, Iturelix, Ixabepilone, Janthinomycin A, Janthinomycin B, Janthinomycin C, Jaspamide, Jasplakinolide, K9-Retrocyclin-1, Kahalalide F, Kaitocephalin, Kanglemycin A, kappa-Conotoxin P VIIA, Kassinatuerin-1, Katanosin A, Katanosin B, Ketamine hydrochloride, Ketanserin, Kifunensine, Kinetin, Kistamicin A, Kopsinine, Korupensamine A, Korupensamine B, Korupensamine C, Kosinostatin, Kurasoin B, Kynostatin-227, Kynostatin-272, Labedipinedilol A, Labedipinedilol B, Labetalol hydrochloride, Labradimil, Lacidipine, Lacosamide, Lactosylphenyl trolox, Ladasten, Ladostigil tartrate, Laflunimus, Lafutidine, Lagatide, Lamectacin, Lamifiban, Landiolol, Lanepitant, Lanreotide acetate, Lansoprazole, Lanthiopeptin, Lapatinib ditosylate, Larazotide acetate, Laromustine, Larotaxel dihydrate, Lasinavir, Latamoxef sodium, Latrunculin S, Lavanduquinocin, Lazabemide hydrochloride, Lecimibide, Lecirelin, Leconotide, Ledazerol, Leflunomide, Lefradafiban, Leinamycin, Leminoprazole, Lemuteporfin, Lemuteporphin, Lenalidomide, Lenampicillin hydrochloride, Lenapenem hydrochloride, Lenapenem hydrochloride hydrate, Lercanidipine hydrochloride, Lerisetron, Lestaurtinib, Leteprinim potassium, Letrazuril, Leualacin, Leucovorin calcium, Leuprolide acetate, Leuprorelin acetate, Leurubicin, Levalbuterol hydrochloride, Levobetaxolol hydrochloride, Levobunolol hydrochloride, Levobupivacaine hydrochloride, Levofolinate calcium, Levoleucovorin calcium, Levonadifloxacin arginine salt, Levonebivolol, Levosalbutamol hydrochloride, Levosimendan, Levosulpiride, L-Fluviabactin, L-Fluvibactin, L-Fluvibactine, L-Histidinol, L-Homothiocitrulline, Liarozole, Liarozole hydrochloride, Liblomycin, Licostinel, Lidamidine hydrochloride, Lidanserin, Lidocaine hydrochloride, Lifarizine, Lifarizine hydrochloride, Lignocaine, Limazocic, Linaprazan, Linarotene, Linazolast, Linetastine, Linezolid, Linezolid oxide, Lingual antimicrobial peptide, Linifanib, Linopristin, Linopristine, Linotroban, Lintitript, Lintopride, Lipohexin, Lipoxazolidinone A, Lipoxazolidinone B, Lipoxazolidinone C, Liraglutide, Lirexapride, Lirimilast, Lisdexamfetamine mesilate, Lisinopril, Lisuride maleate, Lisuride TTS, Litoxetine, Lixivaptan, L-Lysine-d-amphetamine dimesylate, 1-Nebivolol, Lobatamide C, Lobatamide F, Lobeglitazone sulfate, Lobenzarit sodium, Lobophorin A, Lobophorin B, Lobradimil, Lobucavir, Lodamin, Lodenafil, Lofexidine hydrochloride, Loloatin B, Lomefloxacin hydrochloride, Lomeguatrib, Lometrexol, Lopinavir, Loprinone hydrochloride, Loracarbef hydrate, Lorazepam, Lorcaserin, Lorglumide, Lornoxicam, Losartan, Lotrafiban, Loviride, Loxiglumide, Loxistatin, Loxoribine, L-Simexonyl homocysteine, L-Thiocitrulline, L-threitol ceramide, L-threo-C6-pyridinium-ceramide-bromide, Lubazodone hydrochloride, Lufironil, Lumiracoxib, Lurosetron, Luzindole, Lycopersicin, Lymphostin, Lysinated-betulonic acid, Lysobactin, Lysuride maleate, Mabuterol hydrochloride, Macitentan, Magainin II, Makaluvamine C, Makaluvamine D, Makaluvamine E, Makaluvamine F, Makaluvone, Managlinat dialanetil, Manidipine hydrochloride, Manifaxine hydrochloride, Manitimus, Mannopeptimycin alpha, Mannopeptimycin beta, Mannopeptimycin delta, Mannopeptimycin epsilon, Mannopeptimycin gamma, Manumycin A, Manumycin B, Manumycin C, Manumycin E, Manumycin F, Manumycin G, Manzamine A, Manzamine B, Manzamine C, Manzamine D, Manzamine E, Manzamine F, Maprotiline hydrochloride, Maraviroc, Maribavir, Marimastat, Maropitant, Masilukast, Masitinib mesylate, Masnidipine hydrochloride, MASTPROM, Matlystatin A, Matlystatin B, Matlystatin D, Matlystatin E, Matlystatin F, Matristatin A1, Matristatin A2, Matristatin B1, Matristatin D1, Matristatin E1, Matristatin F1, Maxadilan, Mazokalim, Mebrofenin, Mecamylamine hydrochloride, Meclinertant, Meclofenamate sodium, Medetomidine, Mefenamic acid, Mefloquine hydrochloride, Megovalicin A, Megovalicin B, Megovalicin C, Megovalicin D, Megovalicin G, Megovalicin H, Melagatran, Melanotan, Melanotan I, Melanotan II, Meldonium, Melogliptin, Meloxicam, Meluadrine, Meluadrine tartrate, Memno-peptide A, Memoquin, Mephenyloin, Mephobarbital, Mepindolol sulfate, Mepindolol transdermal patch, Mepirodipine hydrochloride, Mepivacaine hydrochloride, Mercaptopurine, Merimepodib, Meriolin-3, Meropenem, Mersacidin, Mesopram, Metaglidasen, Me-Talnetant, Metanicotine, Metaproterenol sulfate, Meterelin, Metergoline, Metesind glucuronate, Metformin hydrochloride, Methamphetamine hydrochloride, Methanobactin, Methicillin sodium, Methimepip, Methoctramine, Methoin, Methotrexate, Methoxatin, Methyclothiazide, Methyl bestatin, Methyl-histaprodifen, Methylhomoindanomycin, Methylphenidate hydrochloride, Methylphenobarbital, Methylphenobarbitone, Methylthio-DADMe-immucillin-A, Methypranolol, Methysergide maleate, Meticillin sodium, Metipranolol, Metoclopramide hydrochloride, Metolazone, Metoprolol fumarate, Metoprolol succinate, Metoprolol tartrate, Mezacopride, Mibefradil, Mibefradil hydrochloride, Micafungin sodium, Michellamine B, Microcin 25, Microcin J25, Microcolin A, Microcolin B, Micronomicin sulfate, Midafotel, Midaxifylline, Mideplanin, Midesteine, Midostaurin, Milacemide-[2H], Milataxel, Milbemycin alpha-9, Milfasartan, Milrinone, Milrinone lactate, Mimopezil, Minalrestat, Minaprine hydrochloride, Minopafant, Mipragoside, Mirabegron, Mirisetron, Mirodenafil hydrochloride, Mitiromycin, Mitomycin, Mitomycin C, Mitoxantrone hydrochloride, Mitozantrone hydrochloride, Mivazerol, Mivobulin isethionate, Mivotilate, Mixanpril, Mizolastine, Mobazol, Mocetinostat dihydrobromide, Moclobemide, Modecamide, Modipafant, Moenomycin A chloride bismuth salt, Moexipril hydrochloride, Moexiprilat, Monamidocin, Monodansyl cadaverine, Mono-L-aspartyl chlorin e6, Monophosphoryl lipid A, Montirelin tetrahydrate, Moracizine hydrochloride, Moranolin, Moricizine hydrochloride, Morniflumate, Mosapramine hydrochloride, Mosapride citrate, Motesanib diphosphate, Motretinide, Moxalactam disodium, Moxifetin hydrogen maleate, Moxifloxacin hydrochloride, Moxonidine hydrochloride hydrate, Mozavaptan hydrochloride, mu-Conotoxin IIIA, Multiple sclerosis vaccine, muO-Conotoxin MrVIB, Muraminomicin A, Muraminomicin B, Muraminomicin C, Muraminomicin D, Muraminomicin E1, Muraminomicin E2, Muraminomicin F, Muraminomicin G, Muraminomicin H, Muraminomicin I, Muraminomicin Z1, Muraminomicin Z2, Muraminomicin Z3, Muraminomicin Z4, Muramyl dipeptide C, Mureidomycin A, Mureidomycin B, Mureidomycin C, Mureidomycin D, Mureidomycin E, Mureidomycin F, Mureidomycins, Muroctasin, Mycalamide A, Mycalamide B, Myxovirescin A1, Myxovirescin B, N1,N8-Bisnorcymserine, N1-Phenethylnorcymserine, N4-Hexadecyl-dC-AZT, Naamidine A, N-Acetylcolchinol, N-Acetylcysteine, N-Acetylesperamycin A1, N-Acetylesperamycin A1b, N-Acetylesperamycin A2, N-Acetyl-L-cysteine, Nadolol, Nafadotride, Nafamostat mesilate, Nafamostat mesylate, Nafarelin acetate, Naglivan, Nagrestipen, Nagstatin, Naltrindole, Naluzotan hydrochloride, Naminidil, Naproxen piperazine (2:1), Napsagatran, Napsamycin A, Napsamycin B, Napsamycin C, Napsamycin D, Naratriptan hydrochloride, Nardeterol, Nateglinide, Navelbine, Navuridine, Naxifylline, Nazasetron, Nazasetron hydrochloride, N-demethylated sildenafil, N-Desmethylmilameline, Nebivolol, Neboglamine, Nebostinel, Necrostatin-1, Nefiracetam, Neihumicin, Nelfinavir mesilate, Nemifitide ditriflutate, Nemonapride, Neo-acridine, Neomycin B-arginine conjugate, Neomycin B-hexaarginine conjugate, Neomycin-acridine, Nepadutant, Nepaprazole, Nepicastat hydrochloride, Neratinib, Nerfilin I, Nesbuvir, Nesiritide, Netamiftide trifluoroacetate, Netilmicin sulfate, Netivudine, Netoglitazone, Neu5Ac2en, Neuromedin U-25, Neuropeptide S, Neutrophil-activating factor, Nevirapine, Ngercheumicin A, Ngercheumicin B, Ngercheumicin C, Ngercheumicin D, Ngercheumicin E, Nibentan, Nicardipine hydrochloride, Nicavir, Nicorandil, Nicotredole, Niduline, Nifedipine, Nifekalant hydrochloride, Nifurzide, Niguldipine hydrochloride, Nilotinib hydrochloride monohydrate, Nilutamide, Nilvadipine, Nimesulide, Nimodipine, Nipradilol, Nipradolol, Nisin, Nisoldipine, Nitazoxanide, Nitracrine dihydrochloride hydrate, Nitrazepam, Nitrendipine, Nitrofenac, Nitroparacetamol, Nitroso-nifedipine, Nitrosopine, Nitrovin, Nivadipine, Nizatidine, Noberastine, Noberastine citrate, Nocathiacin I, Nocathiacin II, Nocathiacin III, Nocathiacin IV, NO-ciprofloxacin, N-Octyl-beta-valienamine, NO-ibuprofen, Nolatrexed dihydrochloride, Nolomirole hydrochloride, NO-Nifedipine, Nooglutil, Nooglutyl, NO-Paracetamol, Norastemizole, Nordazepam, Norfloxacin, Nornicotine, Norsegoline, Nortopixantrone, Nortopixantrone hydrochloride, Nortopsentin A, Nortopsentin B, Nortopsentin C, Nortopsentin D, Nortriptyline hydrochloride, Nostocyclopeptide M1, N-Retinoyl-D-glucosamine, N-tert butyl isoquine, Nubiotic 2, Nutlin-3, Nutlin-3A, Nutlin-3-enantiomer A, Nuvanil, O6-Benzylguanine, Obatoclax mesylate, Oberadilol, Oberadilol monoethyl maleate, Octacosamicin A, Octacosamicin B, Octreother, Octreotide acetate, Octreotide LAR, Odanacatib, O-Demethylmurrayafoline A, Oglufanide disodium, Olanexidine hydrochloride, Olanzapine, Olanzapine pamoate, Olaparib, Olcegepant, Olmesartan, Olmesartan medoxomil, Olprinone hydrochloride, Olradipine hydrochloride, Omaciclovir, Omapatrilat, Ombrabulin, Ombrabulin hydrochloride, omega-Conotoxin CVID, omega-Conotoxin MVIIA, Omeprazole, Omiganan pentahydrochloride, Onnamide A, Ontazolast, Opaviraline, OPC-17083, Opiorphin, Orbifloxacin, Orbofiban acetate, Orciprenaline sulphate, Orienticin A, Orienticin B, Orienticin C, Orienticin D, Oritavancin, Orlipastat, Orlistat, Ortataxel, Oseltamivir carboxylate, Oseltamivir phosphate, Osemozotan hydrochloride, Osutidine, Otamixaban, Otastat potassium, Otenabant hydrochloride, Oteracil potassium, Ovalicin A, Ovothiol B, Oxamflatin, Oxatomide, Oxazepam, Oxeclosporin, Oxiglutatione sodium, Oximidine III, Oxonic acid, Oxprenolol hydrochloride, Oxymetazoline hydrochloride, Oxymethacyl, Oxymorphazole dihydrochloride, Oxynor, Oxypertine, Oystrisin, Ozarelix, Ozenoxacin, Pachymedusa dacnicolor Tryptophyllin-1, Pachysamine E, Paclitaxel, Paclitaxel ceribate, Pactimibe, Padeliporfin potassium, Pafenolol, Palau'amine, Paldimycin B, Palinavir, Palindore fumarate, Palmidrol, Palmitoylethanolamide, Palosuran sulfate, Pamapimod, p-Aminoclonidine hydrochloride, Pancopride, Pancratistatin disodium phosphate, Pancratistatin-3,4-cyclic phosphate sodium salt, Panobinostat, Pantethine, Pantoprazole, Papuamide A, Papuamide B, Papuamide C, Papuamide D, Paracetamol, Paraherquamide E, Paraherquamide F, Paraherquamide G, Parasin I, Parathyroid hormone (human recombinant), Parcetasal, Pardoprunox hydrochloride, Parodilol hemifumarate, Parogrelil hydrochloride, Paroxetine, Paroxetine ascorbate, Paroxetine camsilate, Paroxetine hydrochloride, Paroxetine mesilate, Pasireotide, Pazelliptine trihydrochloride, Pazelliptine trihydrochloride monohydrate, Pazopanib hydrochloride, PEG40000-Paclitaxel, PEG5000-Paclitaxel, PEG-vancomycin, Peldesine, Pelitinib, Pelitrexol, Pemetrexed disodium, Pemirolast, Pemirolast potassium, Pemoline, Penbutolol sulfate, Penciclovir, Penicillin G procaine, Penicillin G sodium, Pentafuside, Pentobarbital sodium, Pentobarbitone sodium, Pentostatin, Peplomycin, Pepticinnamin E, Peptide Leucine Arginine, Peramivir, Perfosfamide, Pergolide mesylate, Perindopril, Perzinfotel, Pexiganan acetate, PG-camptothecin, Phakellistatin 5, Phakellistatin 7, Phakellistatin 8, Phakellistatin 9, Phe-Arg-beta-naphthylamide, Phendioxan, Phenelfamycin F, Phenelzine sulfate, Phenobarbital, Phenobarbitone, Phenochalasin A, Phenochalasin B, Phenoxazole, Phenserine tartrate, Phentolamine mesilate, Phenylisohydantoin, Phenylpseudohydantoin, Phenyloin sodium, Phevalin, Phomopsichalasin, Phortress, Phosphazid, Phosphenyloin sodium, Photofrin II, Physostigmine salicylate, Piboserod hydrochloride, Pibrozelesin hydrochloride, Pibutidine hydrochloride, Piceasin, Piclamilast, Picotamide, Picumeterol fumarate, Pidobenzone, Pidolacetamol, Pidolate magnesium, Pidotimod, Pifatidine, Pikamilone, Piketoprofen, Pilsicamide hydrochloride, Pimagedine, Pimavanserin tartrate, Pimeloylanilide o-aminoanilide, Pimobendan, Pimozide, Pinacidil, Pindolol, Pioglitazone, Pioglitazone hydrochloride, Pipalamycin, Piperacillin sodium, Piperafizine A, Piperafizine B, Piproxen, Piragliatin, Pirbuterol hydrochloride, Pirenzepine hydrochloride, Piroxicam, Piroxicam cinnamate, Piroxicam pivalate, Piscidin 1, Piscidin 2, Piscidin 3, Pittsburgh Compound B, Pivagabine, Pivampicillin, Pixantrone maleate, Platencin, Platensimycin, Plerixafor hydrochloride, Plevitrexed, Plinabulin, Plitidepsin, Plusbacin A1, Plusbacin A2, Plusbacin A3, Plusbacin A4, Plusbacin B1, Plusbacin B2, Plusbacin B3, Plusbacin B4, Pneumocandin A0, Pneumocandin B0, Pneumocandin B0 2-phosphate, Pneumocandin D0, Polaprezinc, Polydiscamide A, Polyglutamate camptothecin, Polymer bound human leukocyte elastase inhibitor, Polythiazide, Porfimer sodium, Poststatin, Pozanicline hydrochloride, PPI17-24, Pradimicin A, Pradimicin B, Pradimicin C, Pradimicin D, Pradimicin E, Pradimicin FA-1, Pradimicin FA-2, Pradimicin FL, Pradimicin FS ((+)-enantiomer), Pradimicin L, Pradimicin S, Pradimicin T1, Pradimicin T2, Pradofloxacin, Pralatrexate, Pralmorelin, Pralnacasan, Pramipexole hydrochloride, Pramipide, Pramiracetam hydrochloride, Pramlintide acetate, Pranazepide, Pranedipine tartrate, Pranidipine, Pranlukast hydrate, Pratosartan, Prefolic A, Premafloxacin, Premafloxacin hydrochloride, Premafloxacin magnesium, Prezatide copper acetate, Primaquine phosphate, Primidone, Prinomastat, Prinomide tromethamine, Prisotinol, Pristinamycin IA, Pristinamycin IB, Pristinamycin IIA, Pristinamycin IIB, Proamipide, Probestin, Procainamide hydrochloride, Procaine Penicillin, Procaterol hydrochloride hemihydrate, Procysteine, Pro-diazepam, Proglumide, Propacetamol hydrochloride, Propafenone hydrochloride, Propeptin, Propeptin T, Propranolol hydrochloride, Prostatin, Protaxel, Protegrin IB-367, Proterguride, Protriptyline hydrochloride, Proxodolol, Prucalopride, Prucalopride hydrochloride, Prucalopride succinate, Pruvanserin hydrochloride, Pseudoephedrine hydrochloride, Pseudomycin A', Pseudomycin B', Psymberin, Ptidepsin, Pumaprazole, Pumosetrag hydrochloride, Purvalanol A, Pyloricidin B, Pymeprazole, Pyrazinoylguanidine, Pyrazoloacridine, Pyridinostatin, Pyridone-6, Pyriferone, Pyrindamycin A, Pyrindamycin B, Pyroxamide, Pyrrocidine A, Pyrrocidine B, Pyrroloquinoline quinone, Pyrrolosporin A, Pyrrophenone, Quarfloxin, Quinagolide hydrochloride, Quinalbarbitone sodium, Quinapril hydrochloride, Quinethazone, Quinotolast sodium, Quinoxapeptin C, Quinupristin mesilate, R9K-Retrocyclin, Rabeximod, rac-Debromoflustramine E, rac-Deoxypseudophrynaminol, Racecadotril, rac-Ptilocaulin nitrate, rac-threo-Methylphenidate hydrochloride, Radequinil, Radezolid, Radolmidine hydrochloride, Rafabegron, Ragaglitazar L-arginine salt, Ralfinamide, Raltegravir potassium, Raltitrexed, Raluridine, Ramatroban, Ramelteon, Ramipril, Ramoplanin A'1, Ramoplanin A'2, Ramoplanin A'3, Ramorelix, Ramosetron hydrochloride, Ranbezolid hydrochloride, Ranimustine, Ranirestat, Ranitidine bismuth citrate, Ranitidine Bismutrex, Ranitidine hydrochloride, Ranitidine nitrate, Ranitidine zinc chloride complex, Ranitidine zinc citrate, Ranolazine, Rasagiline mesilate, Rat adrenomedullin, Razaxaban hydrochloride, Razupenem, Rebamipide, Rebamipide bismuth citrate tetramethyledamine, Rebamipide bismuth L-tartrate tetramethyledamine, Rebimastat, Reblastatin, Reboxetine mesilate, Receptor mediated permeabilizer, Recombinant human parathyroid hormone (1-84), Recombinant Jerdostatin, Regadenoson, Reglitazar, Relacatib, Relaxin-3/INSL5 chimeric peptide, Remacemide hydrochloride, Remikiren mesilate, Reminertant, Remoxipride, Remoxipride hydrochloride monohydrate, Repaglinide, Reparixin, Repertaxin, Repinotan, Repinotan hydrochloride, Repirinast, Reproterol hydrochloride, Resatorvid, Resequinil, Reserpine, Retaspimycin hydrochloride, Retigabine hydrochloride, Retosiban, Revaprazan hydrochloride, Reversine, Revizinone, Rhodopeptin C1, Rhodopeptin C2, Rhodopeptin C3, Rhodopeptin C4, Rhodostreptomycin A, Rhodostreptomycin B, Ricasetron, Rifabutin, Rifalazil, Rifamexil, Rifampicin, Rifampin, Rifapentine, Rifaximin, Rilmazafone hydrochloride dihydrate, Rilmenidine dihydrogen phosphate, Rilpivirine, Rimonabant, Rimoterol hydrobromide, Ripisartan, Risotilide, Rispenzepine hydrochloride, Ritonavir, Ritonavir-oxymethylphosphate, Rivanicline, Rivaroxaban, Rivoglitazone, Rizatriptan benzoate, Rizatriptan sulfate, r-Jerdostatin, Robenacoxib, Robotnikinin, Rocepafant, Roflumilast, Rolapitant hydrochloride, Rolipram, Rolofylline, Romergoline, Romidepsin, Romurtide, Ropinirole hydrochloride, Ropivacaine hydrochloride, Rosabulin, Roscovitine, Rosiglitazone maleate, Rosonabant, Rotigaptide, Roxatidine acetate hydrochloride, Roxatidine bismuth citrate, Roxifiban acetate, Roxindole mesilate, Ruboxistaurin hydrochloride, Ruboxistaurin mesilate hydrate, Rumycin 1, Rumycin 2, Rupintrivir, Ruprintrivir, Sabiporide mesilate, Safinamide mesilate, Safironil, Sagamacin, Sagandipine, Salazodine, Salazopyridazin, Salazosulfapyridine, Salbostatin, Salbutamol nitrate, Salbutamol sulfate, Salcaprozic acid sodium salt, Salicylihalamide A, Salicylihalamide B, Salinamide A, Salinosporamide A, Saliphenylhalamide, Salmaterol, Salmeterol, Salmeterol xinafoate, Salmisteine, Salubrinal, Samixogrel, Sampatrilat, Sampidine, Sanglifehrin A, Sanglifehrin B, Sanglifehrin C, Sanglifehrin D, Sanilvudine, Sapacitabine, Saprisartan, Sapropterin dihydrochloride, Saquinavir, Saquinavir mesilate, Sardomozide, Sardomozide hydrochloride, Saredutant, Sarizotan hydrochloride, Satoribine, Saussureamine C, Saviprazole, Sazetidine-A, Schizandrin glycinosuccinate sodium salt, Scyphostatin, SecinH-3, Secobarbital sodium, Secobatzelline A, Secobatzelline B, Seglitide, Segoline A, Segoline B, Selanc, Selank, Selodenoson, Semagacestat, Semapimod hydrochloride, Semaxanib, Semaxinib, Semoxind, Semparatide, Sepimostat mesilate, Seraspenide, Sermorelin, Sertindole, Sertraline, Sertraline hydrochloride, Setamycin, Setastine hydrochloride, Setazindol, Setipafant, Sezolamide hydrochloride, Shepherdin, Shermilamine D, Shiga vaccine, Shishijimicin A, Shishijimicin B, Shishijimicin C, Sialosylcholesterol-alpha sodium salt, Sialosylcholesterol-beta sodium salt, Siamycin I, Siamycin II, Sibanomicin, Sibenadet hydrochloride, Sibrafiban, Sifuvirtide, Sildenafil citrate, Sildenafil mesilate, Sildenafil nitrate, Sildenafil N-oxide, Silodosin, Siltenzepine, Simendan, Simotaxel, Sinorphan, Sitamaquine hydrochloride, Sivelestat sodium hydrate, Sivifene, SNAP-7292, SNAP-7493, S-Nitrosoglutathione, Soblidotin, Socorromycin, Sofigatran, Sofinicline, Solabegron hydrochloride, Solimastat, Solpecainol hydrochloride, Somocystinamide A, Sorafenib, Sorafenib tosylate, Soraprazan, Sorbicillactone A, Soretolide, Sorivudine, Sotalol hydrochloride, Sotrastaurin, Sparfloxacin, Sparoxomycin A1, Sparoxomycin A2, Sperabillin A, Sperabillin B, Sperabillin C, Sperabillin D, Spermidine/lysine-3/CTS6, Spermine dialdehyde, Spermine/lysine-4/CTS8, Spinorphin, Spiralizone B, Spirapril, Spiriprostil, Spiroglumide, Spiroquinazoline, Spiruchostatin A, Spiruchostatin B, Sprodiamide, Squalamine lactate, Stampidine, Stavudine, Stearyl-norleucine-VIP, Sterenin C, Streptomycin, Stressin1-A, Styloguanidine, Suberanilohydroxamic acid, Suberoylanilide hydroxamic acid, Substance P(8-11), Sufotidine bismuth citrate, Sufugolix, Sulazuril, Sulcephalosporin, Sulfasalazine, Sulfostin, Sulofenur, Sulphasalazine, Sulphostin, Sulpiride, Sulpiride [L-(−)], Sulprostone, Sultamicillin tosylate, Sultopride, Sulukast, Sumanirole maleate, Sumatriptan succinate, Sunflower trypsin inhibitor-1, Sunitinib malate, Super-Leu-Dox, Suplatast tosilate, Suprofenac 1, Suprofenac 2, Suprofenac 3, Suradista, Suramin sodium, Surfen, Surinabant, Suronacrine maleate, Susalimod, Symplostatin 1, Synguanol, Synthadotin, Synthetic human secretin, Synthetic neutrophil inhibitor peptide, Synthetic porcine secretin, Tabilautide, Tabimorelin, Tacapenem pivoxil, Tacedinaline, Tadalafil, Tafenoquine succinate, Tageflar, Talaglumetad hydrochloride, Talaporfin gold sodium, Talaporfin sodium, Talarozole, Talibegron, Talibegron hydrochloride, Tallimustine hydrochloride, Talnetant, Talniflumate, Talopterin, TaIotrexin, Taltirelin, Taltobulin, Taludipine hydrochloride, Talviraline, Tamandarin A, Tamandarin B, Tamatinib fosdium, Tamibarotene, Tamsulosin hydrochloride, Tanaproget, Tandutinib, Tanespimycin, Tanogitran, TAP-doxorubicin, Taranabant, Tarazepide, Targinine, Targinine hydrochloride, Tariquidar, Tasidotin hydrochloride, Tasimelteon, Tasosartan, Taurohyodeoxycholic acid, Tauroiodeoxycholic acid, Taurolidine, Tauropyrone, Taurosteine, Taxuyunnanine, Tazanolast, Tazofelone, Tazopsine, Tebanicline, Tecadenoson, Tecalcet hydrochloride, Tecastemizole, Technetium (99mTc) apcitide, Technetium (99mTc) bicisate, Technetium (99mTc) depreotide, Technetium Tc 99m depreotide, Technetium Tc99m bicisate, Tecovirimat, Tegafur, Tegaserod maleate, Teglicar, Teicoplanin-A2-1, Teicoplanin-A2-2, Teicoplanin-A2-3, Teicoplanin-A2-5, Telaprevir, Telatinib, Telavancin hydrochloride, Telbivudine, Telcagepant, Telinavir, Teludipine hydrochloride, Temacrazine mesilate, Temafloxacin hydrochloride, Temocapril hydrochloride, Temocillin sodium, Temoporfin, Temurtide, Tenatoprazole, Tenovin 6, Tenoxicam, Terbequinil, Terbogrel, Terbutaline sulfate, Terestigmine tartrate, Terguride, Teriflunomide, Teriparatide, Terlakiren, Terlipressin, Ternatin, Terodiline hydrochloride, Tertatolol hydrochloride, Tertomotide, Terutroban sodium, Tesetaxel, Tetrabromostyloguanidine, Tetracaine hydrochloride, Tetrahydrobiopterin, Tetrahydrodercitin 1, Tetrahydroechinocandin B, Tetrahydrolipstatin, Tetrazolast meglumine, Tetrindol, Tetrindole, Texenomycin A, Textilinin-1, Tezampanel, Tezosentan, TGP, Thalidomide, Thanatin, Theopederin D, Theoperidin E, Theophylline, Thiacymserine, Thiamet-G, Thiamphenicol, Thiamylal, Thiatolserine, Thiazinotrienomycin B, Thiazinotrienomycin F, Thiazinotrienomycin G, Thiazohalostatin, Thiocoraline, Thiocoraline A, Thiocoraline NF, Thiofedrine, Thiomarinol, Thiomarinol B, Thiomarinol C, Thiomarinol D, Thiomarinol E, Thiomarinol F, Thionisoxetine-(R), Thiopental sodium, Thiopentone sodium, Thioviridamide, Thioxamycin, Thr10-Contulakin G, Threitol ceramide, Thymalfasin, Thymallene, Thymectacin, Thymic humoral factor gamma-2, Thymoctonan, Thymodolic acid, Thymopentin, Thymosin alpha 1, Tiamdipine, Tiamenidine, Tianeptine sodium, Tiapafant, Tiapride hydrochloride, Tidembersat, Tienartan, Tienoxolol hydrochloride, Tifenazoxide, Tifuvirtide, Tigecycline, Tigilcycline, Tilarginine hydrochloride, Tilisolol hydrochloride, Timodepressin, Timodolic acid, Timogen, Timolol hemihydrate, Timolol maleate, Tinazoline hydrohloride, Tiobutarit, Tiocol 33, Tiocol 54, Tiplimotide, Tipranavir, Tiracizine hydrochloride, Tirofiban hydrochloride, Tiropramide, Tisartan, Tivirapine, Tizanidine hydrochloride, TNF-alpha protease enzyme inhibitor, Toborinone, Tocamide hydrochloride, Tokaramide A, Tolafentrine, Tolbutamide, Tolfenamic acid, Tolvaptan, Tomatine, Tomeglovir, Tomopenem, Tomoxetine hydrochloride, Tonabersat, Topixantrone hydrochloride, Topostatin, Topsentin, Topsentine B1, Torasemide, Torsemide, Tosedostat, Tozasertib, Trabectedin, Tramazoline, Trandolapril, Trandolaprilat, Tranilast, trans,trans-Ceratospongamide, Transdihydrolisuride, Trantinterol hydrochloride, Trapoxin A, Trapoxin B, Trecetilide fumarate, Treprostinil diethanolamine, Tresperimus triflutate, Trewiasine, Triacetyl dynemicin C, Trichostatin D, Triciferol, Trientine hydrochloride, Trifluproxim, Trifluridine, Trimetazidine, Trimetrexate glucuronate, Trimexautide, Triproamylin acetate, Troglitazone, Trombodipine, Tropisetron, Troquidazole, Trovirdine hydrochloride, Troxipide, Trunkamide A, Tryptamide, Tubastrine ((+)-enantiomer), Tubingensin B, Tubulysin A, Tubulysin B, Tubulysin C, Tuftsin, Tulathromycin A, Tulathromycin B, Tulobuterol hydrochloride, Tulobuterol-(R), Tulopafant, Tumor necrosis factor-alpha protease inhibitor, Turbostatin 1, Turbostatin 2, Turbostatin 3, Turbostatin 4, Turofexorate isopropyl, Turosteride ((−)-enantiomer), Tyropeptin A10, Tyropeptin A2, Tyropeptin A6, Tyropeptin A7, Tyropeptin A9, Tyroservaltide, Tyroservatide, Ubenimex, Ubenimex methyl ester, Ubestatin, Ubidine, Udenafil, Ufenamate, Ukrain, Ulicyclamide, Ulifloxacin, Ulithiacyclamide A, Ulvenzepine hydrochloride, Uncialamycin, Uniroyal JR, Unnarmicin A, Unnarmicin C, Upidosin, Upidosin hydrochloride hydrate, Urapidil, Uroguanylin, Urukthapelstatin A, Utibapril, Utibaprilat, V, Vabicaserin hydrochloride, Valaciclovir, Valacyclovir, Valganciclovir hydrochloride, Valnemulin, Valomaciclovir stearate, Valrocemide, Valrubicin, Valsartan, Valsartan axetil, Valsartan cilexetil, Valsartan pivoxil, Valspodar, Vancomycin hydrochloride, Vandetanib, Vanidipinedilol, Vaminolol, Vapitadine hydrochloride, Vardenafil, Vardenafil dihydrochloride, Vardenafil hydrochloride hydrate, Varenicline tartrate, Variapeptin, Varlitinib, Vasonatrin peptide, Vatalanib succinate, Vatanidipine, Vatanidipine hydrochloride, V-Echinocandin, Velneperit, Venorphin, Veralipride, Verongamine, Verticillatine, Vesiculin, Vesnarinone, Vestipitant mesylate, V-Glycopeptide, Vicenistatin, Vilazodone hydrochloride, Vildagliptin, Viloxazine hydrochloride, Vincristine sulfate, Vindesine, Vinflunine, Vinfosiltine sulfate, Vinleucinol, Vinorelbine, Vinxaltine sulfate, Vinylamycin, Virginamycin M2, Virginiamycin M1, Virgisin-1, Virgisin-2, Viscosin, Vistonuridine, Vitilevuamide, Voclosporin, Vofopitant hydrochloride, Voglibose, Volpristin, Voreloxin, Vorinostat, Voxergolide hydrochloride, W Peptide, Watanidipine, Watanidipine hydrochloride, Xamoterol fumarate, Xemilofiban, Xenomin 1, Xenomin 2, Xenoxin-1, Xenoxin-2, Xenoxin-3, Ximelagatran, Xipamide, Yatakemycin, Yohimbine, Yttrium-90 edotreotide, Zabicipril hydrochloride, Zabiciprilat hydrochloride, Zabofloxacin hydrochloride, Zafirlukast, Zampanolide, Zanamivir, Zanapezil fumarate, Zankiren, Zardaverine, Zatosetron, Zatosetron maleate, Zelandopam hydrochloride, Zibotentan, Ziconotide, Zidampidine, Zidovudine, Zilpaterol, Zinc acexamate, Ziprasidone hydrochloride, Ziprasidone mesilate, Zofenoprilat arginine, Zolasartan, Zolmitriptan, Zonampanel, Zorubicin hydrochloride, D may contain further functional groups besides at least one aliphatic amino group to which the promoiety is bound, such further functional group may be aliphatic or aromatic amines, amides, alcohols, carbonyls, carboxylic acids, thiols. The term "aliphatic" (aliphatic fragment) means any aliphatic fragment known to a person skilled in the art.

Preferably, the carrier group Z (PEG or hydrogel) is a polymer with a molecular weight ≥500 g/mol.

In one embodiment, the carrier Z may be a PEG moiety. Such PEG moiety may be attached to the biologically active agent through one or more linkages. In case of one linkage, the corresponding PEG in the PEG prodrug monoconjugate may be linear or branched. In case of more than one linkage, such as in a bisconjugate, the corresponding PEG in the PEG prodrug may be linear or branched. Bisconjugates may contain one or two transient linkages, and PEG may be linear or branched or may contain a mixture of one linear and one branched chain. In case the bisconjugate contains one transient linkage and one linear and one branched chain the transient linkage may be on either chain. In case a branched PEG chain is used, there may be one or more branching units.

A branched PEG is a PEG molecule consisting of a branching point connecting two or more PEG chains, to form a molecule with one anchoring point for attachment to the biologically active agent. This could be two 20 kDa PEG chains joined together to form one branched 40 kDa PEG molecule. In the case where the molecule contains two or three branching points, the molecule is referred to 3- and 4-armed PEG, respectively.

In summary and within the restrictions mentioned above, the PEG polymer is not limited to a particular structure and can be linear, branched, or multi-branched.

Preferably, Z is a hydrogel and more preferably a PEG-based hydrogel. Preferably, the covalent attachment formed between the linker and the hydrogel Z is a permanent bond. The term "PEG based" as understood herein means that the mass proportion of PEG chains in the hydrogel is at least 10% by weight, preferably at least 25%, based on the total weight of the hydrogel. The remainder can be made up of spacers and/or oligomers or polymers, such as oligo- or polylysines.

Moreover, the term "water-insoluble" refers to a swellable three-dimensionally crosslinked molecular network forming the hydrogel. If suspended in a large surplus of water or aqueous buffer of physiological osmolality the hydrogel may take up a substantial amount of water, e.g. up to 10-fold on a weight per weight basis, and is therefore swellable but after removing excess water still retains the physical stability of a gel and a shape. Such shape may be of any geometry and it is understood that such an individual hydrogel object is to be considered as a single molecule consisting of components wherein each component is connected to each other component through chemical bonds.

According to this invention, the hydrogel may be composed of backbone moieties interconnected by hydrolytically degradable bonds.

Preferably, the backbone moiety has a molecular weight in the range of from 1 kDa to 20 kDa, more preferably from 1 kDa to 15 kDa and even more preferably from 1 kDa to 10 kDa. The backbone moieties are preferably also PEG-based, comprising one or more PEG chains.

A preferred aspect of the present invention is a carrier-linked prodrug comprising a biodegradable hydrogel as carrier, wherein a number of permanent linkages of the backbone moieties exist with the linker L to which the biologically active moiety is covalently attached.

Ideally, the hydrogel-connected drug-linker conjugates are dispersed homogeneously throughout the hydrogel according to the invention, and may or may not be present on the surface of the hydrogel according to the invention.

The functional groups may be attached to a linear chain. In this case, the functional groups may be spaced regularly or irregularly across the chain, or alternatively, the chain may be terminated by two dendritic moieties, providing for the total of functional groups.

Remaining reactive functional groups which are not connected to a transient prodrug linker or to a spacer connected to a transient prodrug linker may be capped with suitable blocking reagents.

Preferably, the covalent attachment formed between the reactive functional groups provided by the backbone moieties and the prodrug linker are permanent bonds. Suitable functional groups for attachment of the prodrug linker to the hydrogel according to the invention include but are not limited to carboxylic acid and derivatives, carbonate and derivatives, hydroxyl, hydrazine, hydroxylamine, maleamic acid and derivatives, ketone, amino, aldehyde, thiol and disulfide.

Such biodegradable hydrogel may be composed of backbone moieties interconnected by hydrolytically degradable bonds. The backbone moiety is characterized by a number of functional groups, comprising interconnected biodegradable functional groups and hydrogel-connected drug-linker conjugates, and optionally capping groups. This means that a backbone moiety is characterized by a number of hydrogel-connected drug-linker conjugates; functional groups, comprising biodegradable interconnected functional groups; and optionally capping groups. Preferably, the sum of interconnected biodegradable functional groups and drug-linker conjugates and capping groups is 16-128, preferred 20-100, more preferred 24-80 and most preferred 30-60.

Preferably, the sum of interconnected functional groups and hydrogel-connected drug-linker conjugates and capping groups of a backbone moiety is equally divided by the number of PEG-based polymeric chains extending from the branching core. For instance, if there are 32 interconnected functional groups and hydrogel-connected drug-linker conjugates and capping groups, eight groups may be provided by each of the four PEG-based polymeric chains extending from the core, preferably by means of dendritic moieties attached to the terminus of each PEG-based polymeric chain. Alternatively, four groups may be provided by each of eight PEG-based polymeric chains extending from the core or two groups by each of sixteen PEG-based polymeric chains. If the number of PEG-based polymeric chains extending from the branching core does not allow for an equal distribution, it is preferred that the deviation from the mean number of the sum of interconnected functional groups and hydrogel-connected drug-linker conjugates and capping groups per PEG-based polymeric chain is kept to a minimum.

Preferably, a backbone moiety is further characterized by having a branching core, from which at least three PEG-based polymeric chains extend. Accordingly, in a preferred aspect the backbone reagent comprises a branching core, from which at least three PEG-based polymeric chains extend. Such branching cores may be comprised of poly- or oligoalcohols in bound form, preferably suitably substituted derivatives of pentaerythritol, tripentaerythritol, hexaglycerine, sucrose, sorbitol, fructose, mannitol, glucose, cellulose, amylases, starches, hydroxyalkyl starches, polyvinylalcohols, dextranes, hyaluronans, or branching cores may be comprised of poly- or oligoamines such as ornithine, diaminobutyric acid, trilysine, tetralysine, pentalysine, hexylysine, heptalysine or oligolysine, nonalysine, decalysine, undecalysine, dodecalysine, tridecalysine, tetradecalysine, pentadecalysine or oligolysines, low-molecular weight PEI, polyvinylamines, hexaglycerine, tripentaerythritol, in bound form.

Preferably, the branching core extends three to sixteen PEG-based polymeric chains, more preferably four to eight. Preferred branching cores may be comprised of pentaerythritol, ornithine, diaminobutyric acid, trilysine, tetralysine, pentalysine, hexylysine, heptalysine or oligolysine, low-molecular weight PEI, hexaglycerine, tripentaerythritol in bound form. Preferably, the branching core extends three to sixteen PEG-based polymeric chains, more preferably four to eight. Preferably, a PEG-based polymeric chain is a linear poly(ethylene glycol) chain, of which one end is connected to the branching core and the other to a hyperbranched dendritic moiety. It is understood that a polymeric PEG-based chain may be terminated or interrupted by alkyl or aryl groups optionally substituted with heteroatoms and chemical functional groups.

Preferentially, a backbone moiety is characterized by having a branching core, from which at least three chains extend. Such branching cores may be provided by suitably substituted derivatives of poly- or oligoalcohols, preferably pentaerythritol, tripentaerythritol, hexaglycerine, sucrose, sorbitol, fructose, mannitol, glucose, cellulose, amyloses, starches, hydroxyalkyl starches, polyvinylalcohols, dextranes, hyualuronans, or branching cores may be provided by suitably substituted derivatives of poly- or oligoamines such as trilysine, tetralysine, pentalysine, hexylysine, heptalysine, octalysine, nonalysine, decalysine, undecalysine, dedecalysine, tridecalysine, tetradecalysine, pentadecalysine or oligolysines, polyethyleneimines, polyvinylamines. Preferably, the branching core extends three to sixteen chains, more preferably four to eight. Preferably, such chain is a linear polyethylene glycol chain, of which one end is connected to the branching core and the other to a hyperbranched dendritic moiety.

Preferably, a PEG-based polymeric chain is a suitably substituted polyethylene glycol derivative (PEG based).

Preferred structures for corresponding PEG-based polymeric chains extending from a branching core contained in a backbone moiety are multi-arm PEG derivatives as, for instance, detailed in the products list of JenKem Technology, USA (accessed by download from www.jenkemusa.com on Jul. 28, 2009), 4ARM-PEG Derivatives (pentaerythritol core), 8ARM-PEG Derivatives (hexaglycerin core) and 8ARM-PEG Derivatives (tripentaerythritol core). Most preferred are 4arm PEG Amine (pentaerythritol core) and 4arm PEG Carboxyl (pentaerythritol core), 8arm PEG Amine (hexaglycerin core), 8arm PEG Carboxyl (hexaglycerin core), 8arm PEG Amine (tripentaerythritol core) and 8arm PEG Carboxyl (tripentaerythritol core). Preferred molecular weights for such multi-arm PEG-derivatives in a backbone moiety are 1 kDa to 20 kDa, more preferably 2.5 kDa to 15 kDa and even more preferably 5 kDa to 10 kDa. It is understood that the terminal amine groups of the above mentioned multi-arm molecules are present in bound form in the backbone moiety to provide further interconnected functional groups and reactive functional groups of a backbone moiety.

It is preferred that the sum of interconnected functional groups and reactive functional groups of a backbone moiety is equally divided by the number of PEG-based polymeric chains extending from the branching core. If the number of PEG-based polymeric chains extending from the branching core does not allow for an equal distribution, it is preferred that the deviation from the mean number of the sum of interconnected and reactive functional groups per PEG-based polymeric chain is kept to a minimum.

More preferably, the sum of interconnected and reactive functional groups of a backbone moiety is equally divided by the number of PEG-based polymeric chains extending from the branching core. For instance, if there are 32 interconnected functional groups and reactive functional groups, eight groups may be provided by each of the four PEG-based polymeric chains extending from the core, preferably by means of dendritic moieties attached to the terminus of each PEG-based polymeric chain. Alternatively, four groups may be provided by each of eight PEG-based polymeric chains extending from the core or two groups by each of sixteen PEG-based polymeric chains.

Such multi-arm PEG derivatives may be connected to dendritic moieties to obtain additional functional groups. Preferably, each dendritic moiety has a molecular weight in the range of from 0.4 kDa to 4 kDa, more preferably 0.4 kDa to 2 kDa. Preferably, each dendritic moiety has at least 3 branchings and at least 4 reactive functional groups, and at most 63 branchings and 64 reactive functional groups, preferred at least 7 branchings and at least 8 reactive functional groups and at most 31 branchings and 32 reactive functional groups.

Examples for such dendritic moieties are comprised of trilysine, tetralysine, pentalysine, hexylysine, heptalysine, octadecalysine, nonadecalysine in bound form. Examples for such preferred dendritic moieties are comprised of trilysine, tetralysine, pentalysine, hexylysine, heptalysine in bound form, most preferred trilysine, pentalysine or heptalysine, ornithine, diaminobutyric acid in bound form.

Preferably, such dendritic moieties are comprised of lysine, dilysine, trilysine, tetralysine, pentalysine, hexylysine, heptalysine, most preferred trilysine, pentalysine or heptalyine, in bound form.

Most preferably, the hydrogel of the prodrugs of the present invention is characterized in that the backbone moiety has a quarternary carbon of formula $C(A-Hyp)_4$, wherein each A is independently a poly(ethylene glycol) based polymeric chain terminally attached to the quarternary carbon by a permanent covalent bond and the distal end of the PEG-based polymeric chain is covalently bound to a dendritic moiety Hyp, each dendritic moiety Hyp having at least four groups representing the interconnected functional groups and biodegradable and permanent linkages.

sist of the same or different dendritic moieties Hyp and that each Hyp can be chosen independently. Each moiety Hyp consists of between 5 and 32 lysines, preferably of at least 7 lysines, i.e. each moiety Hyp is comprised of between 5 and 32 lysines in bound form, preferably of at least 7 lysines in bound form. Most preferably Hyp is comprised of heptalysinyl.

The reaction of polymerizable functional groups a backbone reagent, more specifically of Hyp with the polymerizable functional groups of PEG based crosslinker reagents results in a permanent amide bond.

One preferred backbone moiety is shown below, dashed lines indicate interconnecting biodegradable linkages to crosslinker moieties and n is an integer of from 5 to 50:

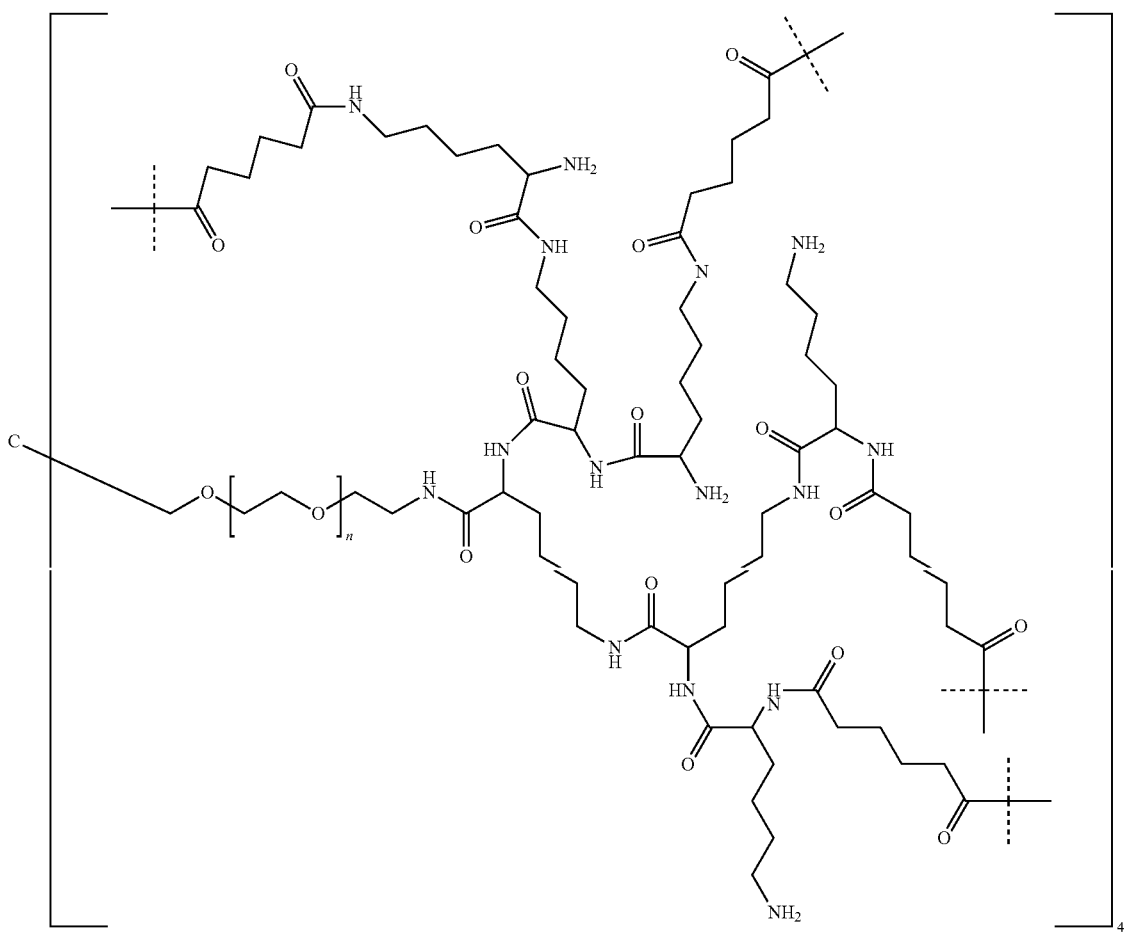

Preferably, each A is independently selected from the formula $-(CH2)_{n1}(OCH_2CH_2)_nX-$, wherein n1 is 1 or 2; n is an integer in the range of from 5 to 50; and X is a functional group covalently linking A and Hyp.

Preferably, A and Hyp are covalently linked by an amide functional group.

Preferably, the dendritic moiety Hyp is a hyperbranched polypeptide. Preferably, the hyperbranched polypeptide comprises lysine in bound form, most preferably Hyp is heptalysinyl in bound form. Preferably, each dendritic moiety Hyp has a molecular weight in the range of from 0.4 kDa to 4 kDa, more preferably in the range of from 0.4 kDa to 2 kDa. It is understood that a backbone moiety $C(A-Hyp)_4$ can con- Preferably, $C(A-Hyp)_4$ has a molecular weight in the range of from 1 kDa to kDa, more preferably from 1 kDa to 15 kDa, more preferably from 2.5 kDa to 15 kDa and even more preferably 5 kDa to 10 kDa.

Preferably, $L^2$ is attached to Z through a thiosuccinimide group which in turn is attached to the hydrogel's backbone moiety through a spacer, such as an oligoethylene glycol chain. Preferably, the linkage of this spacer chain to the backbone moiety is a permanent bond, preferably an amide bond.

Preferably, $L^2$ is a chemical bond.

Biodegradability of the hydrogels according to the present invention is achieved by introduction of hydrolytically degradable bonds.

The terms "hydrolytically degradable", "biodegradable" or "hydrolytically cleavable", "auto-cleavable", or "self-cleavage", "self-cleavable", "transient" or "temporary" refer within the context of the present invention to bonds and linkages which are non-enzymatically hydrolytically degradable under physiological conditions (aqueous buffer at pH 7.4, 37° C.) with half-lives ranging from one hour to three months, include, but are not limited to, aconityls, acetals, carboxylic anhydrides, esters, imines, hydrazones, maleamic acid amides, ortho esters, phosphamides, phosphoesters, phosphosilyl esters, silyl esters, sulfonic esters, aromatic carbamates, combinations thereof, and the like. Preferred biodegradable linkages are esters, carbonates, phosphoesters and sulfonic acid esters and most preferred are esters or carbonates. It is understood that for in vitro studies accelerated conditions like, for example, pH 9, 37° C., aqueous buffer, may be used for practical purposes.

Permanent linkages are non-enzymatically hydrolytically degradable under physiological conditions (aqueous buffer at pH 7.4, 37° C.) with half-lives of six months or longer, such as, for example, amides.

The degradation of the hydrogel is a multi-step reaction where a multitude of degradable bonds is cleaved resulting in degradation products which may be water-soluble or water-insoluble. However each water-insoluble degradation product further comprises degradable bonds so that it can be cleaved in that water-soluble degradation products are obtained. These water-soluble degradation products may comprise one or more backbone moieties. It is understood that released backbone moieties may, for instance, be permanently linked to spacer or blocking groups and/or prodrug-linker degradation products.

In such hydrogel-linked prodrugs according to the invention, it is desirable that almost all release of biologically active agent (>90%) has occurred before a significant amount of release of the backbone degradation products (<10%) has taken place. This can be achieved by adjusting the hydrogel-linked prodrug's half-life versus the hydrogel degradation kinetics.

To introduce the hydrolytically cleavable bonds into the hydrogel carrier of the invention, the backbone moieties can be directly linked to each other by means of biodegradable bonds.

In one embodiment, the backbone moieties of the biodegradable hydrogel carrier may be linked together directly, i.e. without crosslinker moieties. The hyperbranched dendritic moieties of two backbone moieties of such biodegradable hydrogel may either be directly linked through an interconnected functional group that connects the two hyperbranched dendritic moieties. Alternatively, two hyperbranched dendritic moieties of two different backbone moieties may be interconnected through two spacer moieties connected to a backbone moiety and on the other side connected to a crosslinking moiety separated by an interconnected functional groups.

Preferably, backbone moieties may be linked together through crosslinker moieties, each crosslinker moiety being terminated by at least two of the hydrolytically degradable bonds. In addition to the terminating degradable bonds, the crosslinker moieties may contain further biodegradable bonds. Thus, each end of the crosslinker moiety linked to a backbone moiety shows a hydrolytically degradable bond, and additional biodegradable bonds may optionally be present in the crosslinker moiety.

The hydrogel may contain one or more different types of crosslinker moieties, preferably one. The crosslinker moiety may be a linear or branched molecule and preferably is a linear molecule. In a preferred embodiment of the invention, the crosslinker moiety is connected to backbone moieties by at least two biodegradable bonds.

If present in a hydrogel used as carrier in the prodrugs according to the invention as degradable interconnected functional group, preferred biodegradable linkages are carboxylic esters, carboxylic anhydrides, carbonates, phosphoesters and sulfonic acid esters; more preferably carboxylic esters, carbonates, phosphoesters and sulfonic acid esters and most preferred are carboxylic esters or carbonates.

In one embodiment, a crosslinker moiety consists of a polymer. Preferably, crosslinker moieties have a molecular weight in the range of from 0.5 kDa to 5 kDa, more preferably, from 1 kDa to 4 kDa, even more preferably from 1 kDa to 3 kDa.

In addition to oligomeric or polymeric crosslinking moieties, low-molecular weight crosslinking moieties may be used, especially when hydrophilic high-molecular weight backbone moieties are used for the hydrogel formation.

Preferably, the polyethyleneglycol based crosslinker moieties are hydrocarbon chains comprising ethylene glycol units, optionally comprising further functional groups, wherein the poly(ethylene glycol) based crosslinker moieties comprise at least each methylene glycol units, wherein m is an integer in the range of from 3 to 100, preferably from 10 to 70. Preferably, the poly(ethylene glycol) based crosslinker moieties have a molecular weight in the range of from 0.5 kDa to 5 kDa.

If used in reference to a crosslinker moiety or a PEG-based polymeric chain connected to a branching core, the term "PEG-based" refers to a crosslinker moiety or PEG-based polymeric chain comprising at least 20 weight % ethylene glycol moieties.

In one embodiment, monomers constituting the polymeric crosslinker moieties are connected by biodegradable bonds. Such polymeric crosslinkers may contain up to 100 biodegradable bonds or more, depending on the molecular weight of the crosslinker moiety and the molecular weight of the monomer units. Examples for such crosslinkers are polylactic acid or polyglycolic acid based. It is understood that such poly(lactic acid) or poly(glycolic acid) chain may be terminated or interrupted by alkyl or aryl groups and that they may optionally be substituted with heteroatoms and chemical functional groups.

Preferably, the crosslinker moieties are PEG based, preferably represented by only one PEG based molecular chain. Preferably, the poly(ethylene glycol) based crosslinkers are hydrocarbon chains comprising ethylene glycol units, optionally comprising further functional groups, wherein the poly (ethylene glycol) based crosslinker moieties comprise at least each methylene glycol units, wherein m is an integer in the range of from 3 to 100, preferably from 10 to 70. Preferably, the poly(ethylene glycol) based crosslinkers have a molecular weight in the range of from 0.5 kDa to 5 kDa.

In a preferred embodiment of the present invention the crosslinker moiety consists of a PEG chain, which is symmetrically connected through ester bonds to two alpha, omega-aliphatic dicarboxylic spacers provided by backbone moieties through permanent amide bonds.

The dicarboxylic acids of the spacer moieties connected to the backbone moiety and on the other side connected to a crosslinking moiety consists of 3 to 12 carbon atoms, most preferably between 5 and 8 carbon atoms and may be substituted at one or more carbon atom. Preferred substituents are alkyl groups, hydroxy groups or amido groups or substituted amino groups. One or more of the aliphatic dicarboxylic acid's methylene groups may optionally be substituted by O or NH or alkyl-substituted N. Preferred alkyl is linear or branched alkyl with 1 to 6 carbon atoms.

Preferably, there is a permanent amide bond between the hyperbranched dendritic moiety and the spacer moiety connected to a backbone moiety and on the other side is connected to a crosslinking moiety.

One preferred crosslinker moiety is shown below; dashed lines indicate interconnecting biodegradable linkages to backbone moieties:

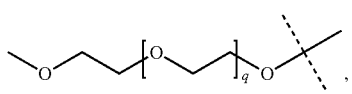

wherein q is an integer of from 5 to 50.

Preferably, the hydrogel carrier is composed of backbone moieties interconnected by hydrolytically degradable bonds.

More preferably, the backbone moieties comprise a branching core of the following formula:

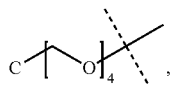

wherein the dashed line indicates attachment to the remainder of the backbone moiety.

More preferably, the backbone moieties comprise a structure of the following formula:

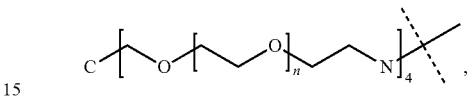

wherein n is an integer of from 5 to 50 and the dashed line indicates attachment to the remainder of the backbone moiety.

Preferably, backbone moiety comprises a hyperbranched moiety Hyp.

More preferably, the backbone moiety comprises a hyperbranched moiety Hyp of the following formula:

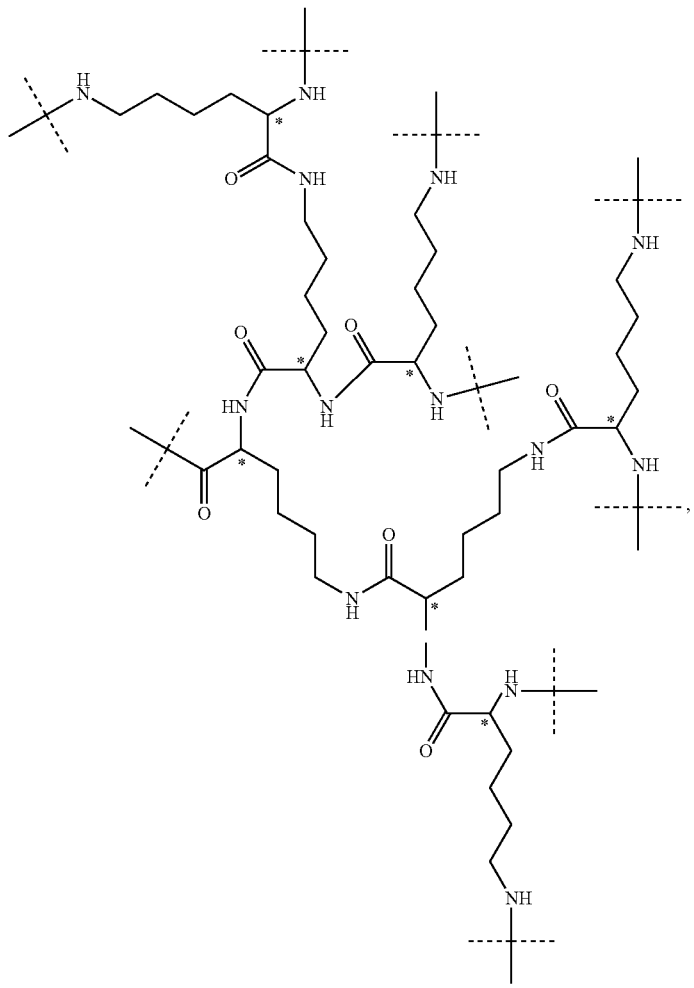

wherein the dashed lines indicate attachment to the rest of the molecule and carbon atoms marked with asterisks indicate in a preferred embodiment S-configuration. However, it is understood that hyperbranched moieties Hyp as shown above may also be in R-confirmation or may be racemic.

Preferably, the backbone moieties are attached to at least one spacer of the following formula:

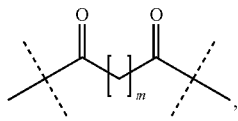

wherein one of the dashed lines indicates attachment to the hyperbranched moiety Hyp and the second dashed line indicates attachment to the rest of the molecule; and wherein m is an integer of from 2 to 4.

Preferably, the backbone moieties are linked together through crosslinker moieties having the following structure

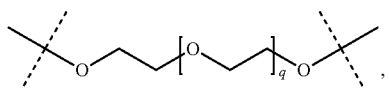

wherein q is an integer from 3 to 100.

More preferably, the backbone moieties of the hydrogel are linked together through moieties of the following formula:

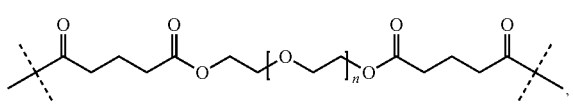

wherein the dashed lines indicate attachment to a backbone moiety, respectively, and wherein n is 45.

In an alternative preferred embodiment, the backbone moieties of the hydrogel are linked together through moieties of the following formula:

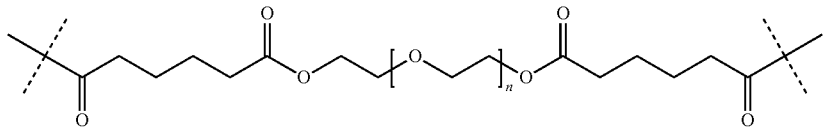

wherein the dashed lines indicate attachment to a backbone moiety, respectively, and wherein n is 22.

The hydrolysis rate of the biodegradable bonds between backbone and crosslinker moieties is influenced or determined by the number and type of connected atoms adjacent to the PEG-ester carboxy group. For instance, by selecting from succinic, adipic or glutaric acid for PEG ester formation it is possible to vary the degradation half-lives of the biodegradable hydrogel carrier.

The hydrogel-linked prodrug of the present invention can be prepared starting from the hydrogel of the present invention by convenient methods known in the art. It is clear to a practitioner in the art that several routes exist. For example, the prodrug linker mentioned above to which the biologically active moiety is covalently attached can be reacted with the reactive functional groups of the hydrogel of the present invention with or with the prodrug linker already bearing the active moiety in part or as whole.

In a preferable method of preparation, the hydrogel is generated through chemical ligation reactions. The hydrogel may be formed from two macromolecular educts with complementary functionalities which undergo a reaction such as a condensation or addition. One of these starting materials is a crosslinker reagent with at least two identical functional groups and the other starting material is a homomultifunctional backbone reagent. Suitable functional groups present on the crosslinker reagent include terminal amino, carboxylic acid and derivatives, maleimide and other alpha,beta unsaturated Michael acceptors like vinylsulfone, thiol, hydroxyl groups. Suitable functional groups present in the backbone reagent include but are not limited to amino, carboxylic acid and derivatives, maleimide and other alpha,beta unsaturated Michael acceptors like vinylsulfone, thiol, hydroxyl groups.

If the crosslinker reagent's reactive functional groups are used substoichiometrically with respect to backbone reactive functional groups, the resulting hydrogel will be a reactive hydrogel with free reactive functional groups attached to the backbone structure.

Optionally, the prodrug linker may be first conjugated to the biologically active agent and the resulting prodrug linker conjugate may then react with the hydrogel's reactive functional groups. Alternatively, after activation of one of the functional groups of the prodrug linker, the linker-hydrogel conjugate may be contacted with biologically active agent in the second reaction step and excess biologically active agent may be removed by filtration after conjugation of the biologically active agent to the hydrogel-bound prodrug linker.

A preferred process for the preparation of a prodrug according to the present invention is as follows:

A preferred starting material for the backbone reagent synthesis is a 4-arm PEG tetra amine or 8-arm PEG octa amine, with the PEG reagent having a molecular weight ranging from 2000 to 10000 Dalton, most preferably from 2000 to 5000 Da. To such multi-arm PEG-derivatives, lysine residues are coupled sequentially to form the hyperbranched backbone reagent. It is understood that the lysines can be partially or fully protected by protective groups during the coupling steps and that also the final backbone reagent may contain protective groups. A preferred building block is bis-boc lysine. Alternatively, instead of sequential additions of lysine residues, a dendritic poly-lysine moiety may be assembled first and subsequently coupled to the 4-arm PEG tetra amine or 8-arm PEG octa amine. It is desirable to obtain backbone reagent carrying 32 amino groups, consequently seven lysines would be attached to each arm of a 4-arm PEG, or three lysines would be attached to each arm of a 8-arm PEG. In another embodiment, the multi-arm PEG derivative is a tetra- or octa carboxy PEG. In this case, the dendritic moieties may be generated from glutaric or aspartic acid, and the resulting backbone reagent would carry 32 carboxy groups. It is understood that all or a fraction of the backbone reagent's functional groups may be present in a free form, as salts or conjugated to protecting groups. It is understood that due to practical reasons the backbone reagent's number of lysines per PEG-arm will be between six and seven, more preferably approximately seven.

A preferred backbone reagent is shown below:

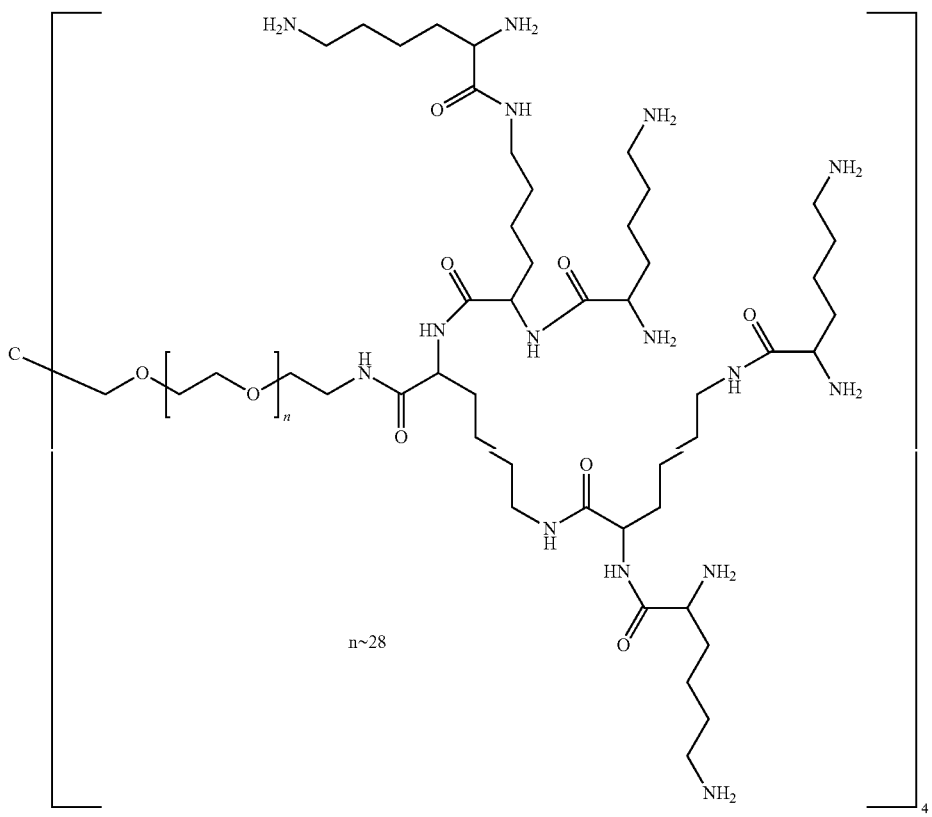

Synthesis of the crosslinker reagent starts from a linear PEG chain with a molecular weight ranging from 0.2 to 5 kDa, more preferably from 0.6 to 2 kDa, which is esterified with a half ester of a dicarboxylic acid, preferably adipic acid or glutaric acid. A preferred protecting group for half ester formation is the benzylic group. The resulting bis dicarboxylic acid PEG half esters are converted into more reactive carboxy compounds, such as acyl chlorides or active esters, eg pentafluorophenyl or N-hydroxysuccinimide esters, most preferred N-hydroxysuccinimde esters, of which a preferred selected structure is shown below.

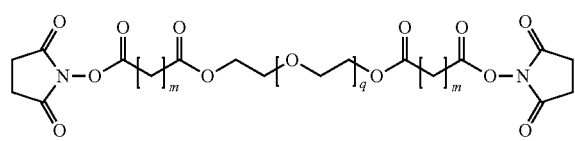

wherein each m independently is an integer ranging from 2 to 4, and q is an integer of from 3 to 100.

More preferred is the following structure:

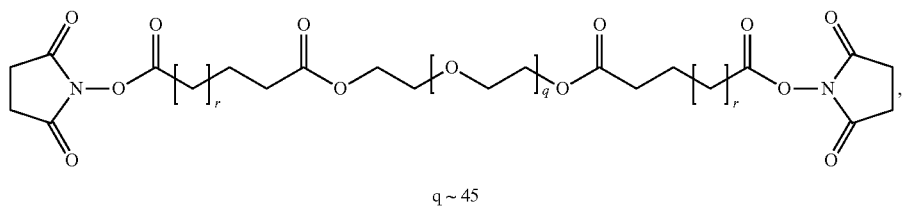

wherein r is either 1 or 2, preferably 1.

Alternatively, the bis-dicarboxylic acid PEG half esters may be activated in the presence of a coupling agent such as DCC or HOBt or PyBOP.

In an alternative embodiment, the backbone reagent carries carboxy groups and the corresponding crosslinker reagent would be selected from ester-containing amino-terminated PEG-chains.

Backbone reagent and crosslinker reagent may be polymerized to form the hydrogel according to the invention using inverse emulsion polymerization. After selecting the desired stoichiometry between backbone and crosslinker functional groups, backbone and crosslinker are dissolved in DMSO and a suitable emulgator with an appropriately selected HLB value, preferably Arlacel P135, is employed to form an inverse emulsion using a mechanical stirrer and controlling the stirring speed. Polymerization is initiated by the addition of a suitable base, preferably by N,N,N',N'-tetramethylene diamine. After stirring for an appropriate amount of time, the reaction is quenched by the addition of an acid, such as acetic acid and water. The beads are harvested, washed, and fractionated according to particle size by mechanical sieving. Optionally, protecting groups may be removed at this stage.

In an alternative embodiment of this invention, multi-functional moieties are coupled to the reactive functional groups of the polymerized reactive hydrogel to increase the number of functional groups which allows increasing the drug load of the hydrogel. Such multi-functional moieties may be provided by suitably substituted derivatives of lysine, dilysine, trilysine, tetralysine, pentalysine, hexylysine, heptalysine, or oligolysine, low-molecular weight PEI. Preferably, the multi-functional moiety is lysine.

Further, such hydrogel according to the invention may be functionalized with a spacer carrying a different reactive functional group than provided by the hydrogel. For instance maleimide reactive functional groups may be introduced into the hydrogel by coupling a suitable heterobifunctional spacer such as Mal-PEG6-NHS to the hydrogel. Such functionalized hydrogel can be further conjugated to drug-linker reagents, carrying a reactive thiol group on the linker moiety to form hydrogel-linked prodrugs according to the present invention.

After loading the drug-linker conjugate to the functionalized maleimido group-containing hydrogel, all remaining functional groups are capped with a suitable blocking reagent, such as mercaptoethanol, to prevent undesired side-reactions.

A particularly preferred method for the preparation of a prodrug of the present invention comprises the steps of
  (a) reacting a compound of formula $C(A'-X1)_4$, wherein A'-X1 represents A before its binding to Hyp or a precursor of Hyp and X1 is a suitable functional group, with a compound of formula Hyp'-X2, wherein Hyp'-X2 represents Hyp before its binding to A or a precursor of Hyp and X2 is a suitable functional group to react with X1;
  (b) optionally reacting the resulting compound from step (a) in one or more further steps to yield a compound of formula $C(A-Hyp)_4$ having at least four functional groups;
  (c) reacting the at least four functional groups of the resulting compound from step (b) with a polyethyleneglycol based crosslinker precursor, wherein the crosslinker precursor is used in a sub-stoichiometric amount compared to the total number of functional groups of $C(A-Hyp)_4$ to yield a hydrogel;
  (d) reacting remaining un-reacted functional groups (representing the reactive functional groups of the backbone comprised in the hydrogel) in the hydrogel backbone of step (c) with a covalent conjugate of biologically active moiety and transient prodrug linker or first reacting the un-reacted functional groups with the transient prodrug linker and subsequently with the biologically active moiety;
  (e) optionally capping remaining un-reacted functional groups to yield a prodrug of the present invention.

Such hydrogel is preferably comminuted by mechanical processes such as stirring, crushing, cutting pressing, or milling, and optionally sieving. For emulsion polymerization, the reaction mixture is comprised of the dispersed phase and the continuous phase.

For the dispersed phase, backbone reagent and crosslinker reagent are mixed in a ratio amine/active ester of 5:1 to 1.05:1, preferably of 2:1 to 1.05:1 and are dissolved in DMSO to give a to give a solution with a concentration of 5 to 50 g per 100 mL, preferably 7 to 30 g per 100 ml, more preferably 7.5 to 20 g per 100 ml and most preferably 10 to 20 g per 100 ml.

The continuous phase is any solvent, that is not miscible with DMSO, not basic, aprotic and shows a viscosity lower than 10 Pa*s. Preferably, the solvent is not miscible with DMSO, not basic, aprotic, shows a viscosity lower than 2 Pa*s and is non-toxic. More preferably, the solvent is a saturated linear or branched hydrocarbon with 5 to 10 carbon atoms. Most preferably, the solvent is n-heptane.

To form an emulsion of the dispersed phase in the continuous phase, an emulsifier is added to the continuous phase before adding the dispersed phase. The amount of emulsifier is 2 to 50 mg per mL dispersed phase, more preferably 5 to 20 mg per mL dispersed phase, most preferably 10 mg per mL dispersed phase.

The emulsifier has an HLB-value of 3 to 8. Preferably, the emulsifier is a triester of sorbitol and a fatty acid or an poly(hydroxyl fatty acid)-poly(ethylene glycol) conjugate. More preferably, the emulsifier is an poly(hydroxy-fatty acid)-polyethylene glycol conjugate, with a linear poly(ethylene glycol) of a molecular weight in the range of from 0.5 kDa to 5 kDa and poly(hydroxy-fatty acid) units of a molecular weight in the range of from 0.5 kDa to 3 kDa on each end of the chain. Most preferably, the emulsifier is poly(ethylene glycol) dipolyhydroxy stearate, Cithrol DPHS (Cithrol DPHS, former Arlacel P135, Croda International Plc).

Droplets of the dispersed phase are generated by stirring with an axial flow impeller with a geometry similar to stirrers such as Isojet, Intermig, Propeller (EKATO Rühr-und Mischtechnik GmbH, Germany), most preferably similar to Isojet or Propeller with a diameter of 50 to 90% of the reactor diameter. Preferably, stirring is initiated before addition of the dispersed phase. Stirrer speed is set to 0.6 to 2.4 m/s, such as 0.8 to 2.3 m/s, preferably to 0.6 to 1.7 m/s. The dispersed phase is added at room temperature, and the concentration of the disperse phase is 2% to 70%, preferably 5 to 50%, more preferably 10 to 40%, and most preferably 20 to 35% of the total reaction volume. The mixture of dispersed phase, emulsifier and continuous phase is stirred for 5 to 60 min before adding the base to the effect polymerization.

5 to 10 equivalents (referred to each amide bond to be formed) of a base are added to the mixture of dispersed and continuous phase. The base is aprotic, non nucleophilic and soluble in the disperse phase. Preferably, the base is aprotic, non nucleophilic, well soluble in both disperse phase and DMSO. More preferably, the base is aprotic, non nucleophilic, well soluble in both disperse phase and DMSO, an amine base and non-toxic. Most preferably, the base is N,N,N',N'-tertramethylethylene diamine (TMEDA). Stirring in the presence of base is continued for 1 to 16 h.

During stirring, droplets of dispersed phase are hardened to become crosslinked hydrogel beads according to the invention which can be collected and fractionation according to size is performed on a vibrational continuous sieving machine with a 75 µm and a 32 µm deck to give hydrogel microparticles according to the invention.

The hydrogel for the prodrug of the present invention can be obtained from the preparation methods in form of microparticles. In a preferred embodiment of the invention, the reactive hydrogel is a shaped article such as a mesh or a stent. Most preferably, the hydrogel is formed into microparticulate beads which can be administered as subcutaneous or intramuscular injectably by means of a standard syringe. Such soft beads may have a diameter of between 1 and 500 micrometer.

Preferably, such beaded carrier-linked hydrogel prodrugs have a diameter of between 10 and 100 micrometer if suspended in an isotonic aqueous formulation buffer, most preferably a diameter of between 20 and 100 micrometer, most preferably a diameter of between 25 and 80 micrometer.

Preferably, such beaded carrier-linked hydrogel prodrugs can be administered by injection through a needle smaller than 0.6 mm inner diameter, preferably through a needle smaller than 0.3 mm inner diameter, more preferably through a needle small than 0.25 mm inner diameter, even more preferably through a needle smaller than 0.2 mm inner diameter, and most preferably through a needle small than 0.16 mm inner diameter.

It is understood that the terms "can be administered by injection", "injectable" or "injectability" refer to a combination of factors such as a certain force applied to a plunger of a syringe containing the carrier-linked hydrogel prodrugs according to the invention swollen in a liquid at a certain concentration (w/v) and at a certain temperature, a needle of a given inner diameter connected to the outlet of such syringe, and the time required to extrude a certain volume of the carrier-linked hydrogel prodrugs according to the invention from the syringe through the needle.

In order to provide for injectability, a volume of 1 mL of the carrier-linked hydrogel prodrugs swollen in water to a concentration of at least 5% (w/v) and contained in a syringe holding a plunger of a diameter of 4.7 mm can be extruded at room temperature within 10 seconds by applying a force of less than 60 Newton, such as less than 50 Newton, preferably by applying a force of less than 40 Newton.

Preferably injectability measurement is carried out for the carrier-linked hydrogel prodrugs of the present invention swollen in water to a concentration of ca. 15% (w/v).

By consequence, the prodrugs according to the present invention show the beneficial effect of a controlled release rate in respect of the released drug D-H. Preferably, a sustained release rate is obtained. Sustained release means that the administration intervals of the respective prodrug are expanded. For example, prodrugs according to the present invention which are based on drugs commonly applied once or several times a day provide therapeutically effective levels for at least three days, more preferably for at least one week and even more preferably for at least one month.

The prodrug according to the present invention show excellent in vivo/in vitro correlation of linker cleavage, a high degree of enzyme independence and show a higher stability at lower pH, resulting in a pH dependent cleavage.

A strong in vivo/in vitro correlation is observed, if the release kinetics exhibited by a carrier-linked prodrug conjugate according to the invention in vivo has a half-life that is not smaller than half the value exhibited by the same carrier-linked prodrug conjugate in aqueous buffer of pH 7.4 at 37° C., wherein the release kinetics in vivo is measured as plasma levels of free drug. It is understood that in the case of soluble carriers, release kinetics may be recorded as hydrolysis kinetics.

Another aspect of the present invention are pharmaceutical compositions of the carrier-linked prodrugs described before. Such pharmaceutical compositions contain one or more excipients, selected from the groups consisting of:

(i) Buffering agents: physiologically tolerated buffers to maintain pH in a desired range, such as sodium phosphate, bicarbonate, succinate, histidine, citrate and acetate, sulphate, nitrate, chloride, pyruvate. Antacids such as $Mg(OH)_2$ or $ZnCO_3$ may be also used. Buffering capacity may be adjusted to match the conditions most sensitive to pH stability.

(ii) Isotonicity modifiers: to minimize pain that can result from cell damage due to osmotic pressure differences at the injection depot. Glycerin and sodium chloride are examples. Effective concentrations can be determined by osmometry using an assumed osmolality of 285-315 mOsmol/kg for serum.

(iii) Preservatives and/or antimicrobials: multidose parenteral preparations may require the addition of preservatives at a sufficient concentration to minimize the risk of patients becoming infected upon injection and corresponding regulatory requirements have been established. Typical preservatives include m-cresol, phenol, methylparaben, ethylparaben, propylparaben, butylparaben, chlorobutanol, benzyl alcohol, phenylmercuric nitrate, thimerosol, sorbic acid, potassium sorbate, benzoic acid, chlorocresol, and benzalkonium chloride.

(iv) Stabilizers: Stabilisation is achieved by strengthening of the protein-stabilising forces, by destabilisation of the denatured stater, or by direct binding of excipients to the protein. Stabilizers may be amino acids such as alanine, arginine, aspartic acid, glycine, histidine, lysine, proline, sugars such as glucose, sucrose, trehalose, polyols such as glycerol, mannitol, sorbitol, salts such as potassium phosphate, sodium sulphate, chelating agents such as EDTA, hexaphosphate, ligands such as divalent metal ions (zinc, calcium, etc.), other salts or organic molecules such as phenolic derivatives. In addition, oligomers or polymers such as cyclodextrins, dextran, dendrimers, PEG or PVP or protamine or HSA may be used.

(v) Anti-adsorption agents: Mainly ionic or inon-ionic surfactants or other proteins or soluble polymers are used to coat or adsorb competitively to the inner surface of the composition's container, e.g. poloxamer (Pluronic F-68), PEG dodecyl ether (Brij 35), polysorbate 20 and 80, dextran, polyethylene glycol, PEG-polyhistidine, BSA and HSA and gelatines. Chosen concentration and type of excipient depends on the effect to be avoided but typically a monolayer of surfactant is formed at the interface just above the CMC value.

(vi) Lyo- and/or cryoprotectants: During freeze- or spray drying, excipients may counteract the destabilising effects caused by hydrogen bond breaking and water removal. For this purpose, sugars and polyols may be used, but corresponding positive effects have also been observed for surfactants, amino acids, non-aqueous solvents, and other peptides. Trehalose is particularly efficient at reducing moisture-induced aggregation and also improves thermal stability potentially caused by exposure of protein hydrophobic groups to water. Mannitol and sucrose may also be used, either as sole lyo/cryoprotectant or in combination with each other where higher ratios of mannitol:sucrose are known to enhance physical stability of a lyophilized cake. Mannitol may also be combined with trehalose. Trehalose may also be combined with sorbitol or sorbitol may be used as the sole protectant. Starch or starch derivatives may also be used.

(vii) Oxidation protection agents: antioxidants such as ascorbic acid, ectoine, methionine, glutathione, monothioglycerol, morin, polyethylenimine (PEI), propyl gallate, vitamin E, chelating agents such aus citric acid, EDTA, hexaphosphate, thioglycolic acid.

(viii) Viscosifiers or viscosity enhancers: retard settling of the particles in the vial and syringe and are used in order to facilitate mixing and resuspension of the particles and to make the suspension easier to inject (i.e., low force on the syringe plunger). Suitable viscosifiers or viscosity enhancers are, for example, carbomer viscosifiers like Carbopol 940, Carbopol Ultrez 10, cellulose derivatives like hydroxypropylmethylcellulose (hypromellose, HPMC) or diethylaminoethyl cellulose (DEAE or DEAE-C), colloidal magnesium silicate (Veegum) or sodium silicate, hydroxyapatite gel, tricalcium phosphate gel, xanthans, carrageenans like Satia gum UTC 30, aliphatic poly(hydroxy acids), such as poly(D, L- or L-lactic acid) (PLA) and poly(glycolic acid) (PGA) and their copolymers (PLGA), terpolymers of D,L-lactide, glycolide and caprolactone, poloxamers, hydrophilic poly(oxyethylene) blocks and hydrophobic poly(oxypropylene) blocks to make up a triblock of poly(oxyethylene)-poly(oxypropylene)-poly(oxyethylene) (e.g. Pluronic®), polyether-ester copolymer, such as a polyethylene glycol terephthalate/polybutylene terephthalate copolymer, sucrose acetate isobutyrate (SAIB), dextran or derivatives thereof, combinations of dextrans and PEG, polydimethylsiloxane, collagen, chitosan, polyvinyl alcohol (PVA) and derivatives, polyalkylimides, poly (acrylamide-co-diallyldimethyl ammonium (DADMA)), polyvinylpyrrolidone (PVP), glycosaminoglycans (GAGs) such as dermatan sulfate, chondroitin sulfate, keratan sulfate, heparin, heparan sulfate, hyaluronan, ABA triblock or AB block copolymers composed of hydrophobic A-blocks, such as polylactide (PLA) or poly(lactide-co-glycolide) (PLGA), and hydrophilic B-blocks, such as polyethylene glycol (PEG) or polyvinyl pyrrolidone. Such block copolymers as well as the abovementioned poloxamers may exhibit reverse thermal gelation behavior (fluid state at room temperature to facilitate administration and gel state above sol-gel transition temperature at body temperature after injection).

(ix) Spreading or diffusing agent: modifies the permeability of connective tissue through the hydrolysis of components of the extracellular matrix in the intrastitial space such as, but not limited to, hyaluronic acid, a polysaccharide found in the intercellular space of connective tissue. A spreading agent such as, but not limited to, hyaluronidase temporarily decreases the viscosity of the extracellular matrix and promotes diffusion of injected drugs.

(x) Other auxiliary agents: such as wetting agents, viscosity modifiers, antibiotics, hyaluronidase. Acids and bases such as hydrochloric acid and sodium hydroxide are auxiliary agents necessary for pH adjustment during manufacture.

The composition of a prodrug according to the invention may be provided as a liquid composition, a suspension composition or as a dry composition.

In one embodiment, the pharmaceutical composition of a prodrug according to the invention is a dry composition. Suitable methods of drying are, for example, spray-drying and lyophilization (freeze-drying). Preferably, the pharmaceutical composition of prodrug is dried by lyophilization.

Preferably, the prodrug is sufficiently dosed in the composition to provide therapeutically effective amounts of biologically active agent for at least 12 hours in one application. More preferably, one application of prodrug is sufficient for at least one day, more preferably for at least 3 days, more preferably for at least 1 week and most preferably for at least 4 weeks.

In one embodiment of the present invention, the composition of prodrug is provided as a single dose, meaning that the container in which it is supplied contains one pharmaceutical dose.

In another embodiment, the composition is provided as a multiple dose composition, meaning that it contains more than one therapeutic dose. Preferably, a multiple dose composition contains at least 2 doses. Such multiple dose composition of prodrug can either be used for different patients in need thereof or is intendend for use in one patient, wherein the remaining doses are stored after the application of the first dose until needed.

In another aspect of the present invention the prodrug composition is comprised in a container. For liquid or suspension compositions, the container is preferably a single chamber syringe. For dry compositions, preferably the container is a dual-chamber syringe. The dry composition according to the present invention is provided in a first chamber of the dual-chamber syringe and reconstitution solution is provided in a second chamber of the dual-chamber syringe.

Prior to applying the dry composition of prodrug to a patient in need thereof, the dry composition is reconstituted. Reconstitution can take place in the container in which the dry composition of prodrug is provided, such as in a vial, syringe, dual-chamber syringe, ampoule, and cartridge. Reconstitution is done by adding a predefined amount of reconstitution solution to the dry composition. Reconstitution solutions are sterile liquids, such as water or buffer, which may contain further additives, such as preservatives and/or antimicrobials, such as, for example, benzylalcohol and cresol. Preferably, the reconstitution solution is sterile water.

A further aspect is a method of preparing a reconstituted composition comprising a therapeutically effective amount of prodrug, and optionally one or more pharmaceutically acceptable excipients, the method comprising the step of contacting the composition of the present invention with a reconstitution solution.

Another aspect is a reconstituted composition comprising a therapeutically effective amount of a prodrug according to the invention, and optionally one or more pharmaceutically acceptable excipients.

Another aspect of the present invention is the method of manufacturing a liquid or suspension composition of carrier-linked prodrug. In one embodiment, such composition is made by
  (i) admixing the carrier-linked prodrug with one or more excipients,
  (ii) transfering amounts of the liquid or suspension composition equivalent to single or multiple doses into suitable containers, and
  (iii) sealing the containers.

Another aspect of the present invention is the method of manufacturing a dry composition of carrier-linked prodrug. In one embodiment, such composition is made by
  (i) admixing the carrier-linked prodrug with one or more excipients,
  (ii) transferring amounts equivalent to single or multiple doses into suitable containers,
  (iii) drying the composition in said containers, and
  (iv) sealing the containers.

Suitable containers are vials, syringes, dual-chamber syringes, ampoules, and cartridges.

Another aspect is a kit of parts. For liquid and suspension compositions, and when the administration device is simply a hypodermic syringe, the kit may comprise the syringe, a needle and a container comprising the carrier-linked prodrug composition for use with the syringe. In case of a dry composition, the container may have one chamber containing the dry carrier-linked prodrug composition, and a second chamber comprising a reconstitution solution. In more preferred embodiments, the injection device is other than a simple hypodermic syringe and so the separate container with carrier-linked prodrug composition is adapted to engage with the injection device such that in use the liquid or suspension or reconstituted dry composition in the container is in fluid connection with the outlet of the injection device. Examples of administration devices include but are not limited to hypodermic syringes and pen injector devices. Particularly preferred injection devices are the pen injectors, in which case the container is a cartridge, preferably a disposable cartridge.

A preferred kit of parts comprises a needle and a container containing the dry carrier-linked prodrug composition according to the present invention and optionally further containing a reconstitution solution, the container being adapted for use with the needle. Preferably, the container is a dual-chamber syringe.

In another aspect, the invention provides a cartridge containing a composition of carrier-linked prodrug as hereinbefore described for use with a pen injector device. The cartridge may contain a single dose or multiplicity of doses of carrier-linked prodrug.

In one embodiment of the present invention the suspension composition of carrier-linked prodrug does not only comprise a carrier-linked prodrug and one or more excipients, but also other biologically active agents, either in their free form or as prodrugs or carrier-linked prodrugs such as PEG prodrugs or hydrogel prodrugs. Preferably, such additional one or more biologically active agent is a prodrug, more preferably a PEG or hydrogel prodrug.

In an alternative embodiment, the carrier-linked prodrug composition according to the present invention is combined with a second biologically active compound in such way that the carrier-linked prodrug composition according to the invention is administered to a patient in need thereof first, followed by the administration of the second compound. Alternatively, the carrier-linked prodrug composition is administered to a patient in need thereof after another compound has been administered to the same patient.

Yet another aspect of the present invention is a carrier-linked prodrug of the present invention or a pharmaceutical composition of the present invention for use as a medicament.

Yet another aspect of the present invention is a carrier-linked prodrug of the present invention or a pharmaceutical composition of the present invention for use in a method of treating or preventing diseases or disorders which can be treated by the biologically active moiety released from the carrier-linked prodrug according to the present invention.

Another subject of the present invention is a method for the synthesis of a carrier-linked prodrug or a pharmaceutically acceptable salt thereof as defined above. Carrier-linked prodrugs or precursors of carrier-linked prodrugs according to the present invention may be prepared by known methods or in accordance with the reaction sequences described below. The starting materials used in the preparation (synthesis) of prodrugs of the invention or precursors thereof are known or commercially available, or can be prepared by known methods or as described below.

All reactions for the synthesis of the carrier-linked prodrugs according to the present invention including precursors such as the moiety $L^1$ according to the formula (I) are per se well-known to the skilled person and can be carried out under standard conditions according to or analogously to procedures described in the literature, for example in Houben-Weyl, Methoden der Organischen Chemie (Methods of Organic Chemistry), Thieme-Verlag, Stuttgart, or Organic Reactions, John Wiley & Sons, New York. Depending on the circumstances of the individual case, in order to avoid side reactions during the synthesis of a carrier-linked prodrug or a precursor thereof, it can be necessary or advantageous to temporarily block functional groups by introducing protective groups and to deprotect them in a later stage of the synthesis, or introduce functional groups in the form of precursor groups which in a later reaction step are converted into the desired functional groups. Such synthesis strategies and protective groups and precursor groups which are suitable in an individual case are known to the skilled person. If desired, the carrier-linked prodrugs or precursors can be purified by customary purification procedures, for example by recrystallization or chromatography.

The carrier-linked prodrugs according to the present invention or a pharmaceutically acceptable salt thereof may be prepared by a method comprising the step of reacting a prodrug precursor L-Y with a biologically active drug D-H to obtain the drug linker conjugate D-L by forming an amide bond, wherein Y is a leaving group.

In respect of the prodrug precursor L-Y, L has the same meaning as indicated above in connection with the drug linker conjugate D-L. The same holds true for the analogous employment of the prodrug precursor $L^1$-Y in respect of the moiety $L^1$ represented by formula (I).

Y is a leaving group. Such leaving groups are known to a person skilled in the art. Preferably, Y is chloride, bromide, fluoride, nitrophenoxy, imidazolyl, N-hydroxysuccinimidyl, N-hydroxybenzotriazolyl, N-hydroxyazobenzotriazolyl, pentafluorophenoxy, 2-thiooxo-thiazolidinyl, or N-hydroxysulfosuccinimidyl.

In case the synthesis of a carrier-linked prodrug according to the present invention is carried out by employing a precursor $L^1$-Y, a drug linker intermediate ($L^1$-D) is obtained by reacting $L^1$-Y with the biologically active drug D-H by forming an amide bond. In such case, said drug linker intermediate $L^1$-D is reacted further to obtain the drug linker conjugate D-L by adding the moiety $L^2$ and the carrier group Z to said drug linker intermediate $L^1$-D. It has to be indicated that the addition of $L^2$ and/or Z to $L^1$-D may be performed in several steps by preparing further intermediate compounds prior to obtaining the drug linker conjugate D-L.

Alternatively, a prodrug precursor L*-Y may be employed instead of $L^1$-Y, wherein L* is selected from a fragment of $L^1$, $L^1$ containing at least one protecting group or $L^1$ additionally containing precursors of $L^2$ and/or Z.

Another subject of the present invention is the use of prodrugs or a pharmaceutically acceptable salt thereof comprising a drug linker conjugate D-L as pharmaceuticals or medicaments, respectively. With respect of the definitions of the drug linker conjugate D-L as well as further substituents such as $L^1$ the same explanations as laid out above in the context of the prodrug as such apply.

EXAMPLES

Example 1

Synthesis of Linker Reagent Intermediate (1)

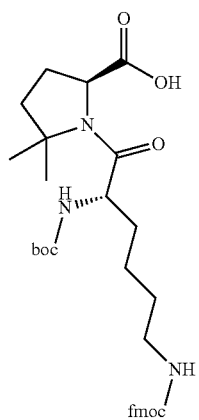

Fmoc-5,5-dimethyl-L-proline (0.9 mmol) is loaded onto 2-chlorotrityl resin (0.6 mmol) according to manufacturer's instructions. After fmoc removal, a solution of boc-Lys (fmoc)-OH (3 mmol), HATU (3 mmol), and collidine (6 mmol) is added to the resin and incubated for 30 min. This procedure is repeated once. Intermediate 1 is cleaved from resin according to the following procedure:

The resin is washed with DCM, dried in vacuo and treated two times for 30 minutes with 6/4 (v/v) DCM/HFIP Eluates are combined, volatiles are removed under a nitrogen stream and product 1 is purified by RP-HPLC and analyzed by RP-HPLC-MS.

Example 2

Synthesis of Exendin-4 Linker Intermediate (2)

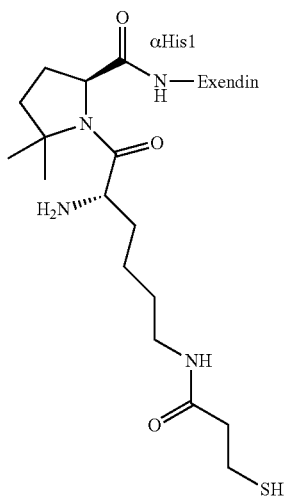

2

1 (0.10 mmol), PyBOP (0.10 mmol), and DIEA (0.20 mmol) are dissolved in 2 ml of dry DME Mixture is added to 250 mg side-chain protected Exendin-4 (J. Eng et al., J. Biol. Chem. 1992, 267, 11, 7402-7405) on-resin (25 µmol; synthesized by Fmoc-strategy on Rink amide resin) and agitated for 30 min at room temperature. Resin is washed with DMF (10 times) and DCM (10 times). Fmoc-group is removed by agitating the resin with 2/2/96 (v/v/v) piperidine/DBU/DMF (two times, 10 min each) and washing with DMF (ten times). Trt-mercaptopropionic acid (0.1 mmol), PyBOB (0.1 mol), and DIEA (0.2 mmol) in DMF are added to the resin and agitated for 30 min at room temperature. 2 is cleaved from resin according to the following procedure:

The resin is washed with DCM, dried in vacuo and treated with 2 ml of TFA cleavage cocktail (TFA/TES/Water/DTT 95/2/2/1) per 100 mg resin for 60 min at room temperature. Volatiles are removed under a nitrogen stream. Nonpolar side products and protecting groups are removed by precipitating peptide from diethyl ether. Precipitate is dried in vacuo.

Crude 2 is dissolved in acetonitrile/water 1/1 and purified by RP-HPLC.

Example 3

Synthesis of PEG-Linker-Exendin-4 Conjugate (3)

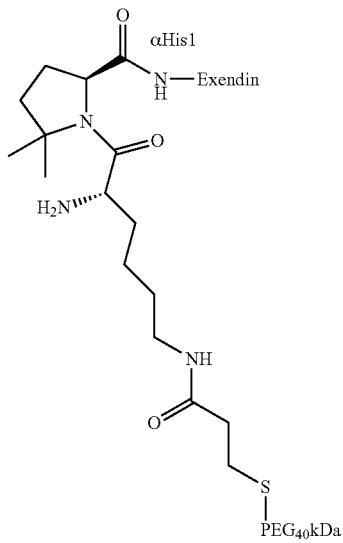

3

2 (12 mg) is dissolved in 500 µl of 1/1 acetonitrile/water and 120 mg 40 kDa methoxy poly(ethylene glycol) maleimido-propionamide in 1 ml of 1/1 acetonitrile/water are added. 300 µl of 0.25 M sodium phosphate buffer pH 7.0 are added and solution is acidified after 10 min with 300 µl acetic acid. 3 is purified by cation exchange chromatography, desalted, and then lyophilized.

Example 4

Exendin-4 Release In Vitro

Release of exendin from 3 is effected by hydrolysis in 50 mM sodium phosphate buffer at pH 7.4 and 37° C. Unmodified native exendin-4 is released as assessed by RP-HPLC/MS.

Example 5

Synthesis of Linker Reagent Intermediate (4)

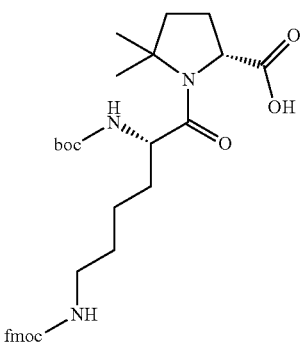

4

Fmoc-5,5-dimethyl-D-proline (0.9 mmol) was loaded onto 2-chlorotrityl resin (0.6 mmol) according to manufacturer's instructions. After fmoc removal, a solution of boc-Lys (fmoc)-OH (3 mmol), HATU (3 mmol), and collidine (6 mmol) was added to the resin and incubated for 30 min. This procedure was repeated once. Intermediate 4 was cleaved from resin according to the following procedure:

The resin was washed with DCM, dried in vacuo and treated two times for minutes with 6/4 (v/v) DCM/HFIP. Eluates were combined, volatiles were removed under a nitrogen stream and product 4 was purified by RP-HPLC and analyzed by RP-HPLC-MS.

Example 6

Synthesis of Amoxapine Linker Intermediate (5)

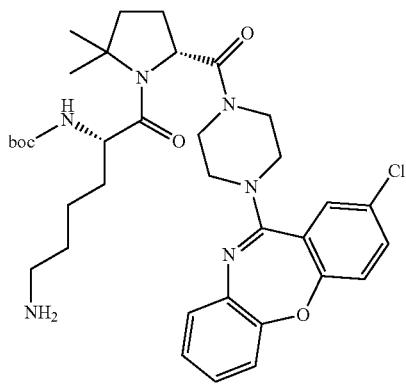

5

5 (26 µmol), PyBOP (32 µmol), and DIEA (63 µmol) were dissolved in 250 L of anhydrous DME Amoxapine (36 µmol) was added, and the mixture was stirred at room temperature for 50 min. Piperidine (63 µL) was added and stirring was continued for 20 minutes. The crude product was purified by RP-HPLC. Yield 83%.

Example 7

Synthesis of PEG-Linker-Amoxapine Conjugate (6)

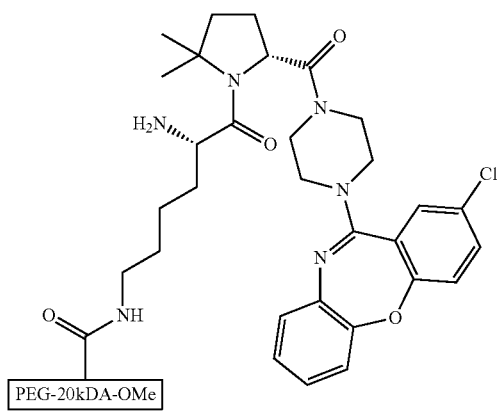

6

To a solution of 5 (1.4 mg) in 50 µL of DMSO were added a solution of 63 mg 20 kDa methoxy poly(ethylene glycol) NHS ester in 500 µL ml of DMSO and 7 µL of DIPEA. After incubation at 22° C. for 30 min, the reaction mixture was frozen and lyophilized.

Dry samples were treated with TFA/DCM 1:1(v/v) for 20 min, diluted with MeCN and purified by RP-HPLC.

Example 8

Amoxapine Release In Vitro

Release of amoxapine from 6 was effected by hydrolysis in 50 mM sodium phosphate buffer at pH 7.4 and 37° C. Unmodified amoxapine is released as assessed by RP-HPLC/MS.

$t_{1/2} = 1.75h$.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

Abbreviations:

Boc t-butyloxycarbonyl

DBU 1,3-diazabicyclo[5.4.0]undecene

DCM dichloromethane

DIEA diisopropylethylamine

DMF N,N-dimethylformamide

DMSO dimethylsulfoxide

DTT dithiothreitol

Fmoc 9-fluorenylmethoxycarbonyl

HATU O-(7-Azabenzotriazol-1-yl)-N,N,N',N'-tetramethyluronium hexafluorophosphate HFIP hexafluoroisopropanol MeCN acetonitrile MS mass spectrometry PEG poly(ethylene glycol)

PyBOP benzotriazole-1-yl-oxy-tris-pyrrolidino-phosphonium hexafluorophosphate

RP-HPLC reversed-phase high performance liquid chromatography

TES triethylsilane

TFA trifluoroacetic acid

The invention claimed is:

1. A prodrug or a pharmaceutically acceptable salt thereof comprising:

a drug linker conjugate D-L;

wherein D is a biologically active moiety containing an aliphatic amine containing group; and wherein L is a non-biologically active linker containing:
i) a moiety $L^1$ represented by formula (I):

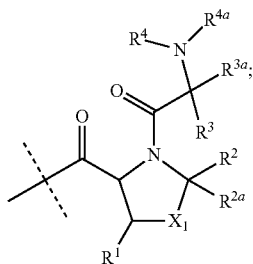

wherein the dashed line indicates the attachment of $L^1$ to the aliphatic amine group of D by forming an amide bond;
wherein $X_1$ is selected from O, S, and CH—$R^{1a}$;
wherein $R^1$ and $R^{1a}$ are independently selected from H, OH, and $CH_3$;
wherein $R^2$, $R^{2a}$, $R^4$, and $R^{4a}$ are independently selected from H and $C_{1-4}$ alkyl;
wherein $R^3$ and $R^{3a}$ are independently selected from H, $C_{1-4}$ alkyl, and $R^5$; and
wherein $R^5$ is selected from:

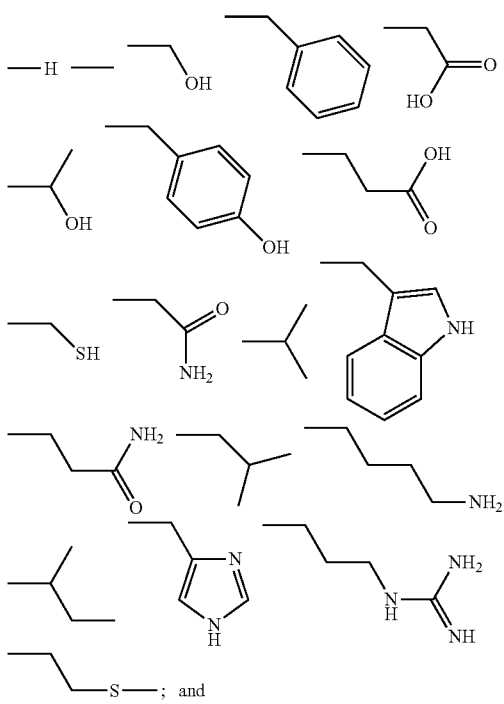

wherein, optionally, one or more of the pairs $R^3/R^{3a}$, $R^4/R^{4a}$, and $R^3/R^4$ may independently form one or more cyclic fragments selected from $C_{3-7}$ cycloalkyl, 4 to 7 membered heterocyclyl, and 9 to 11 membered heterobicyclyl; and wherein, optionally, $R^3$, $R^{3a}$, $R^4$ and $R^{4a}$ are further substituted; and
ii) a moiety $L^2$, which is a chemical bond or a spacer, and $L^2$ is bound to a carrier group Z;
wherein $L^1$ is substituted with one to four $L^2$ moieties;
wherein Z is a hydrogel; and
wherein, optionally, L is further substituted.

2. The prodrug according to claim 1;
wherein $L^2$ is a chemical bond.

3. The prodrug of claim 1;
wherein the hydrogel is composed of backbone moieties interconnected by hydrolytically degradable bonds.

4. The prodrug of claim 3;
wherein the backbone moieties have a molecular weight in the range of from 1 kDa to 20 kDa.

5. The prodrug of claim 3;
wherein backbone moieties are linked together through crosslinker moieties, each crosslinker moiety being terminated by at least two of the hydrolytically degradable bonds.

6. The prodrug of claim 5;
wherein the crosslinker moieties have a molecular weight in the range of from 0.5 kDa to 5 kDa.

7. A pharmaceutical composition comprising:
a prodrug of claim 1 or a pharmaceutically acceptable salt thereof; and
a pharmaceutically acceptable excipient.

8. The pharmaceutical composition according to claim 7;
wherein the pharmaceutical composition is dry.

9. The pharmaceutical composition according to claim 7;
wherein the prodrug is sufficiently dosed in the composition to provide a therapeutically effective amount of biologically active agent for at least 12 hours in one application.

10. A kit of parts comprising.
a needle; and
a container containing;
reconstitution solution; and
the dry composition according to claim 9 configured for use with the needle.

11. The kit of parts according to claim 10;
wherein the container is a dual-chamber syringe; and
wherein one of the two-chambers of the dual-chamber syringe contains the dry pharmaceutical composition and the second chamber of said dual-chamber syringe contains the reconstitution solution.

12. The pharmaceutical comprising: the prodrug according to claim 1;

13. A method for the synthesis of a prodrug or a pharmaceutically acceptable salt thereof according to claim 1, comprising:
a step of reacting a prodrug precursor L-Y or $L^1$-Y with a biologically active drug D-H, to obtain the drug linker conjugate D-L or a drug linker intermediate D-$L^1$ by forming an amide bond;
wherein Y is a leaving group.

14. The prodrug according to claim 1;
wherein the carrier group Z is a PEG based hydrogel.

15. The prodrug according to claim 1;
wherein the carrier group Z is a biodegradable polyethylene glycol based water-insoluble hydrogel.

* * * * *